United States Patent
Sullivan

(10) Patent No.: US 12,428,399 B2
(45) Date of Patent: Sep. 30, 2025

(54) NON-HYGROSCOPIC CRYSTALLINE SALTS OF A PYRAZOLE COMPOUND, AND PHARMACEUTICAL COMPOSITIONS AND USE THEREOF

(71) Applicant: Yissum Research Development Company of the Hebrew University of Jerusalem Ltd., Jerusalem (IL)

(72) Inventor: Robert W. Sullivan, Vista, CA (US)

(73) Assignee: Yissum Research Development Company of the Hebrew University of Jerusalem Ltd, Jerusalem (IL)

( * ) Notice: Subject to any disclaimer, the term of this patent is extended or adjusted under 35 U.S.C. 154(b) by 895 days.

(21) Appl. No.: 17/596,023

(22) PCT Filed: Jun. 2, 2020

(86) PCT No.: PCT/US2020/035654
§ 371 (c)(1),
(2) Date: Dec. 2, 2021

(87) PCT Pub. No.: WO2020/247345
PCT Pub. Date: Dec. 10, 2020

(65) Prior Publication Data
US 2022/0332702 A1    Oct. 20, 2022

Related U.S. Application Data

(60) Provisional application No. 62/856,605, filed on Jun. 3, 2019.

(51) Int. Cl.
| | | |
|---|---|---|
| *C07D 403/04* | (2006.01) |
| *A61K 31/506* | (2006.01) |
| *A61K 45/06* | (2006.01) |
| *A61P 35/00* | (2006.01) |
| *A61P 35/02* | (2006.01) |

(52) U.S. Cl.
CPC .......... *C07D 403/04* (2013.01); *A61K 31/506* (2013.01); *A61K 45/06* (2013.01); *A61P 35/00* (2018.01); *A61P 35/02* (2018.01); *C07B 2200/13* (2013.01)

(58) Field of Classification Search
CPC ........ C07D 403/04; A61P 35/02; A61P 35/00; A61K 31/506; A61K 45/06; C07B 2200/13
See application file for complete search history.

(56) References Cited

FOREIGN PATENT DOCUMENTS

| WO | WO-2017021969 A1 * | 2/2017 | ........... A61K 31/506 |
| WO | WO-2019155468 A1 * | 8/2019 | ........... A61K 31/437 |

OTHER PUBLICATIONS

Bastin et al., Salt Selection and Optimization Procedures for New Chemical Entities, Organic Process Research & Development, vol. 4, Issue 5, Sep. 2000, pp. 427-435 (Year: 2000).*
Berege et al., Pharmaceutical Salts, J. Pharm Sci, vol. 66, No. 1, Jan. 1977 (Year: 1977).*
Saal et al., Pharmaceutical Salts: A Summary on Doses of Salt Formers from the Orange Book, European Journal of Pharmaceutical Sciences, 49 (2013) 614-623 (Year: 2013).*

* cited by examiner

*Primary Examiner* — Andrew D Kosar
*Assistant Examiner* — Phillip Matthew Rzeczycki
(74) *Attorney, Agent, or Firm* — Giordano Law LLC; David A. Giordano

(57) ABSTRACT

Provided herein are non-hygroscopic crystalline salts of (1r,4r)-$N^1$-(5-chloro-4-(5-(cyclopropylmethyl)-1-methyl-1H-pyrazol-4-yl)pyrimidin-2-yl)cyclohexane-1,4-diamine and pharmaceutical compositions thereof. Also provided are methods of their use for treating, preventing, or ameliorating one or more symptoms of a proliferative disease.

18 Claims, 39 Drawing Sheets

NON-HYGROSCOPIC CRYSTALLINE SALTS OF A PYRAZOLE COMPOUND, AND PHARMACEUTICAL COMPOSITIONS AND USE THEREOF

CROSS REFERENCE TO RELATED APPLICATION

This application is a National Stage of International Application No. PCT/US2020/035654, filed Jun. 2, 2020; which claims the benefit of U.S. Provisional Application No. 62/856,605, filed Jun. 3, 2019; the disclosure of each of which is incorporated herein by reference in its entirety.

FIELD

Provided herein are non-hygroscopic crystalline salts of (1r,4r)-$N^1$-(5-chloro-4-(5-(cyclopropylmethyl)-1-methyl-1H-pyrazol-4-yl)pyrimidin-2-yl)cyclohexane-1,4-diamine and pharmaceutical compositions thereof. Also provided are methods of their use for treating, preventing, or ameliorating one or more symptoms of a proliferative disease.

BACKGROUND

Casein kinases are serine/threonine kinases that phosphorylate proteins to mediate normal biological functions and malignant transformation. Schittek and Sinnberg, *Mol. Cancer* 2014, 13, 231-245. Casein kinase 1 alpha (CK1α) functions as a tumor inducer through negative regulation of Wnt/β-catenin signaling and p53. Ebert and Kronke, *N. Engl. J. Med.* 2018, 379, 1873-1874. CK1α phosphorylates 0-catenin at Ser 45, leading to ubiquitination and degradation of the signaling protein. Schittek and Sinnberg, *Mol. Cancer* 2014, 13, 231-245; Elyada et al., *Nature* 2011, 470, 409-413. CK1α also phosphorylates murine double minute X (MDMX) at Ser 289, resulting in enhanced binding of MDMX to p53. Wu et al., *Mol. Cell. Biol.* 2012, 32, 4821-4832. Moreover, a complex of CK1α and MDM2 also inhibits p53. Elyada et al., *Nature* 2011, 470, 409-413. Thus, inhibition of CK1α with subsequent p53 activation has the potential to be effective in treating a wide array of cancers.

$N^1$-(5-Chloro-4-(5-(cyclopropylmethyl)-1-methyl-1H-pyrazol-4-yl)pyrimidin-2-yl)cyclohexane-1,4-diamine ("the Compound") is a CK1α inhibitor as well as an inhibitor of transcriptional kinases CDK7 and CDK9. Minzel et al., *Cell* 2018, 175, 171-185. The Compound reduces Ser 45 β-catenin phosphorylation and increases p53 and β-catenin protein expression. Id. The Compound also significantly reduces expression of key cancer initiating genes, including Myc, MDM2, and MCL1. Id. The Compound as a hydrochloride salt is effective in treating acute myeloid leukemia (AML) in AML mouse models and human-patient-derived xenograph mouse models. Id. However, the hydrochloride salt of the Compound is highly hygroscopic and not suitable for pharmaceutical applications. Therefore, there is a need for a non-hygroscopic salt of $N^1$-(5-chloro-4-(5-(cyclopropyl-methyl)-1-methyl-1H-pyrazol-4-yl)pyrimidin-2-yl)cyclohexane-1,4-diamine.

SUMMARY OF THE DISCLOSURE

Provided herein is a non-hygroscopic crystalline salt of (1r,4r)-$N^1$-(5-chloro-4-(5-(cyclopropylmethyl)-1-methyl-1H-pyrazol-4-yl)pyrimidin-2-yl)cyclohexane-1,4-diamine or an isotopic variant thereof with an acid; or a pharmaceutically acceptable solvate thereof. In one embodiment, the acid is acetic acid, adipic acid, benzoic acid, fumaric acid, glycolic acid, hippuric acid, lactic acid, maleic acid, malic acid, methanesulfonic acid, succinic acid, sulfuric acid, tartaric acid, thiocyanic acid, or p-toluenesulfonic acid.

Also provided herein is a crystalline acetate salt of (1r,4r)-$N^1$-(5-chloro-4-(5-(cyclopropylmethyl)-1-methyl-1H-pyrazol-4-yl)pyrimidin-2-yl)cyclohexane-1,4-diamine or an isotopic variant thereof, or a pharmaceutically acceptable solvate thereof.

Additionally provided herein is a crystalline adipate salt of (1r,4r)-$N^1$-(5-chloro-4-(5-(cyclopropylmethyl)-1-methyl-1H-pyrazol-4-yl)pyrimidin-2-yl)cyclohexane-1,4-diamine or an isotopic variant thereof, or a pharmaceutically acceptable solvate thereof.

Further provided herein is a crystalline benzoate salt of (1r,4r)-$N^1$-(5-chloro-4-(5-(cyclopropylmethyl)-1-methyl-1H-pyrazol-4-yl)pyrimidin-2-yl)cyclohexane-1,4-diamine or an isotopic variant thereof; or a pharmaceutically acceptable solvate thereof.

Provided herein is a crystalline fumarate salt of (1r,4r)-$N^1$-(5-chloro-4-(5-(cyclopropylmethyl)-1-methyl-1H-pyrazol-4-yl)pyrimidin-2-yl)cyclohexane-1,4-diamine or an isotopic variant thereof, or a pharmaceutically acceptable solvate thereof.

Provided herein is a crystalline glycolate salt of (1r,4r)-$N^1$-(5-chloro-4-(5-(cyclopropylmethyl)-1-methyl-1H-pyrazol-4-yl)pyrimidin-2-yl)cyclohexane-1,4-diamine or an isotopic variant thereof, or a pharmaceutically acceptable solvate thereof.

Provided herein is a crystalline hippurate salt of (1r,4r)-$N^1$-(5-chloro-4-(5-(cyclopropylmethyl)-1-methyl-1H-pyrazol-4-yl)pyrimidin-2-yl)cyclohexane-1,4-diamine or an isotopic variant thereof, or a pharmaceutically acceptable solvate thereof.

Provided herein is a crystalline lactate salt of (1r,4r)-$N^1$-(5-chloro-4-(5-(cyclopropylmethyl)-1-methyl-1H-pyrazol-4-yl)pyrimidin-2-yl)cyclohexane-1,4-diamine or an isotopic variant thereof, or a pharmaceutically acceptable solvate thereof.

Provided herein is a crystalline maleate salt of (1r,4r)-$N^1$-(5-chloro-4-(5-(cyclopropylmethyl)-1-methyl-1H-pyrazol-4-yl)pyrimidin-2-yl)cyclohexane-1,4-diamine or an isotopic variant thereof, or a pharmaceutically acceptable solvate thereof.

Provided herein is a crystalline malate salt of (1r,4r)-$N^1$-(5-chloro-4-(5-(cyclopropylmethyl)-1-methyl-1H-pyrazol-4-yl)pyrimidin-2-yl)cyclohexane-1,4-diamine or an isotopic variant thereof, or a pharmaceutically acceptable solvate thereof.

Provided herein is a crystalline mesylate salt of (1r,4r)-$N^1$-(5-chloro-4-(5-(cyclopropylmethyl)-1-methyl-1H-pyrazol-4-yl)pyrimidin-2-yl)cyclohexane-1,4-diamine or an isotopic variant thereof, or a pharmaceutically acceptable solvate thereof.

Provided herein is a crystalline succinate salt of (1r,4r)-$N^1$-(5-chloro-4-(5-(cyclopropylmethyl)-1-methyl-1H-pyrazol-4-yl)pyrimidin-2-yl)cyclohexane-1,4-diamine or an isotopic variant thereof, or a pharmaceutically acceptable solvate thereof.

Provided herein is a crystalline sulfate salt of (1r,4r)-$N^1$-(5-chloro-4-(5-(cyclopropylmethyl)-1-methyl-1H-pyrazol-4-yl)pyrimidin-2-yl)cyclohexane-1,4-diamine or an isotopic variant thereof, or a pharmaceutically acceptable solvate thereof.

Provided herein is a crystalline tartrate salt of (1r,4r)-$N^1$-(5-chloro-4-(5-(cyclopropylmethyl)-1-methyl-1H-pyrazol- 4-yl)pyrimidin-2-yl)cyclohexane-1,4-diamine or an isotopic variant thereof, or a pharmaceutically acceptable solvate thereof.

Provided herein is a crystalline thiocyanate salt of (1r,4r)-N[1]-(5-chloro-4-(5-(cyclopropylmethyl)-1-methyl-1H-pyrazol-4-yl)pyrimidin-2-yl)cyclohexane-1,4-diamine or an isotopic variant thereof, or a pharmaceutically acceptable solvate thereof.

Provided herein is a crystalline p-toluenesulfonate salt of (1r,4r)-N[1]-(5-chloro-4-(5-(cyclopropylmethyl)-1-methyl-1H-pyrazol-4-yl)pyrimidin-2-yl)cyclohexane-1,4-diamine or an isotopic variant thereof, or a pharmaceutically acceptable solvate thereof.

Provided herein is a pharmaceutical composition comprising a non-hygroscopic crystalline salt of (1r,4r)-N[1]-(5-chloro-4-(5-(cyclopropylmethyl)-1-methyl-1H-pyrazol-4-yl)pyrimidin-2-yl)cyclohexane-1,4-diamine or an isotopic variant thereof with an acid; or a pharmaceutically acceptable solvate thereof; and a pharmaceutically acceptable excipient.

Provided herein is a method of treating, preventing, or ameliorating one or more symptoms of a proliferative disease in a subject, comprising administering to the subject a non-hygroscopic crystalline salt of (1r,4r)-N[1]-(5-chloro-4-(5-(cyclopropylmethyl)-1-methyl-1H-pyrazol-4-yl)pyrimidin-2-yl)cyclohexane-1,4-diamine or an isotopic variant thereof with an acid; or a pharmaceutically acceptable solvate thereof.

Provided herein is a method of treating, preventing, or ameliorating one or more symptoms of a disorder, disease, or condition mediated by a casein kinase 1 (CK1) in a subject, comprising administering to the subject a therapeutically effective amount of a non-hygroscopic crystalline salt of (1r,4r)-N[1]-(5-chloro-4-(5-(cyclopropylmethyl)-1-methyl-1H-pyrazol-4-yl)pyrimidin-2-yl)cyclohexane-1,4-diamine or an isotopic variant thereof with an acid; or a pharmaceutically acceptable solvate thereof.

DETAILED DESCRIPTION

Figure 1:
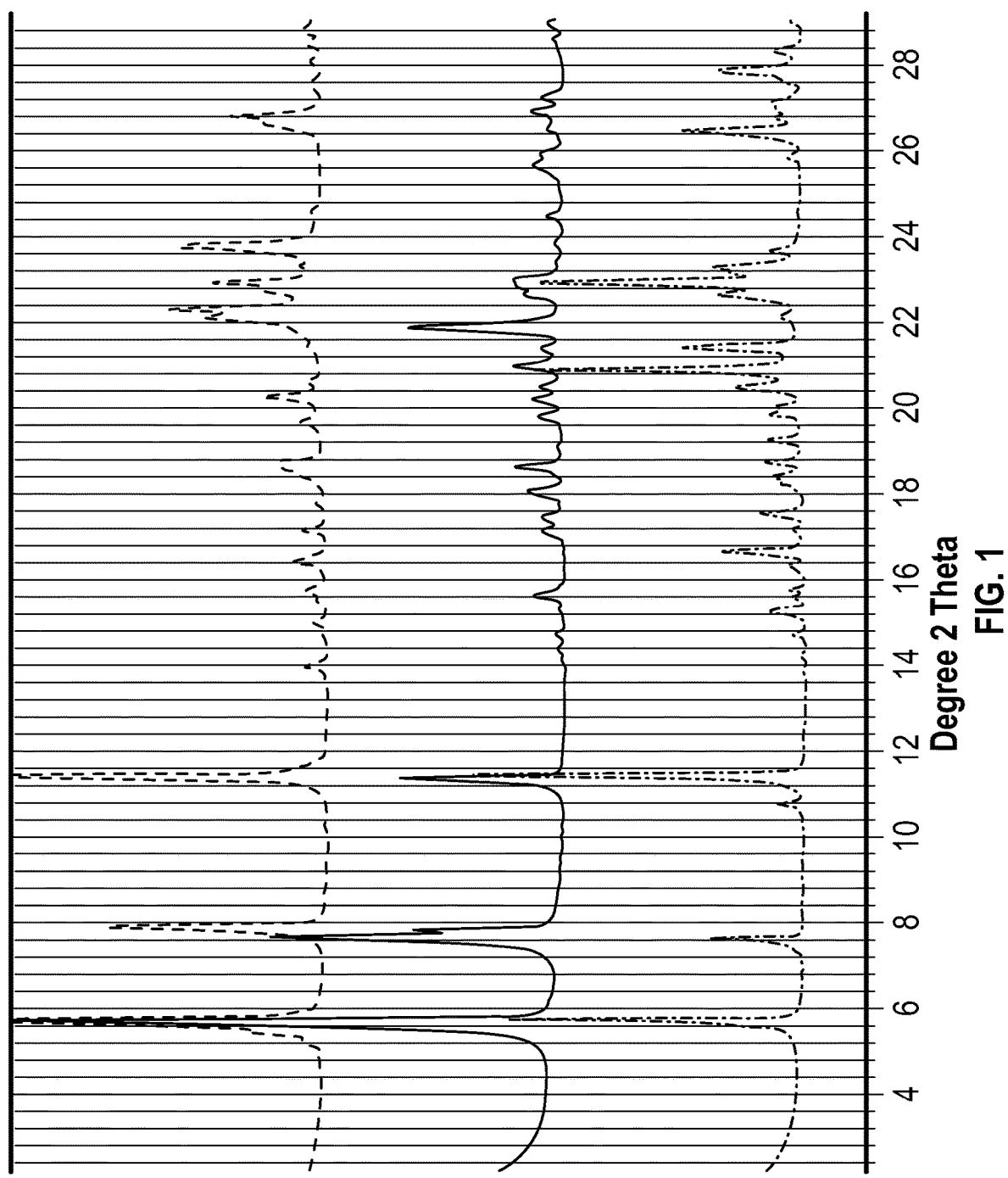
FIG. 1 depicts X-ray powder diffractograms of two crystalline acetate salts (the top and middle diffractograms) and one crystalline adipate salt (the bottom diffractogram) of (1r,4r)-N[1]-(5-chloro-4-(5-(cyclopropylmethyl)-1-methyl-1H-pyrazol-4-yl)pyrimidin-2-yl)cyclohexane-1,4-diamine ("the Compound").

To facilitate understanding of the disclosure set forth herein, a number of terms are defined below.

Generally, the nomenclature used herein and the laboratory procedures in organic chemistry, medicinal chemistry, physical chemistry, biochemistry, biology, pharmacology, and others described herein are those well known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject. In one embodiment, the subject is a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The terms "alleviate" and "alleviating" refer to easing or reducing one or more symptoms (e.g., pain) of a disorder, disease, or condition. The terms can also refer to reducing adverse effects associated with an active ingredient. Sometimes, the beneficial effects that a subject derives from a prophylactic or therapeutic agent do not result in a cure of the disorder, disease, or condition.

The term "therapeutically effective amount" or "effective amount" is meant to include the amount of a compound that, when administered, is sufficient to prevent development of, or alleviate to some extent, one or more of the symptoms of the disorder, disease, or condition being treated. The term "therapeutically effective amount" or "effective amount" also refers to the amount of a compound that is sufficient to elicit a biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of a subject (e.g., a human or an animal) without excessive toxicity, irritation, allergic response, immunogenicity, or other problems or complications, commensurate with a reasonable benefit/risk ratio. See, *Remington: The Science and Practice of Pharmacy*, 22nd ed.; Allen Ed.: Philadelphia, PA, 2012; 8th ed.; Sheskey et al., Eds.; The Pharmaceutical Press and the American Pharmacists Association: 2017; *Handbook of Pharmaceutical Additives*, 3rd ed.; Ash and Ash Eds.; Gower Publishing Company: 2007; *Pharmaceutical Preformulation and Formulation*, 2nd ed.; Gibson Ed.; CRC Press LLC: Boca Raton, FL, 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The term "isotopically enriched" refers to a compound that contains an unnatural proportion of an isotope at one or more of the atoms that constitute such a compound. In certain embodiments, an isotopically enriched compound contains unnatural proportions of one or more isotopes, including, but not limited to, hydrogen (H), deuterium ($^2$H), tritium (H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I), iodine-125 ($^{125}$I) iodine-127 ($^{127}$I), iodine-129 ($^{129}$I), and iodine-131 ($^{131}$I). In certain embodiments, an isotopically enriched compound is in a stable form, that is, non-radioactive. In certain embodiments, an isotopically enriched compound contains unnatural proportions of one or more isotopes, including, but not limited to, hydrogen ($^1$H), deuterium (2H), carbon-12 ($^{12}$C), carbon-13 ($^{13}$C), nitrogen-14 ($^{14}$N), nitrogen-15 ($^{15}$N), oxygen-16 ($^{16}$O), oxygen-17 ($^{17}$O), oxygen-18 ($^{18}$O), fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S), chlorine-35 ($^{35}$Cl), chlorine-37 ($^{37}$Cl), bromine-79 ($^{79}$Br), bromine-81 ($^{81}$Br), and iodine-127 ($^{127}$I). In certain embodiments, an isotopically enriched compound is in an unstable form, that is, radioactive. In certain embodiments, an isotopically enriched compound contains unnatural proportions of one or more isotopes, including, but not limited to, tritium (H), carbon-11 ($^{11}$C), carbon-14 ($^{14}$C), nitrogen-13 ($^{13}$N), oxygen-14 ($^{14}$O), oxygen-15 ($^{15}$O), fluorine-18 ($^{18}$F), phosphorus-32 ($^{32}$P), phosphorus-33 ($^{33}$P), sulfur-35 ($^{35}$S), chlorine-36 ($^{36}$Cl), iodine-123 ($^{123}$I), iodine-125 ($^{125}$I), iodine-129 ($^{129}$I), and iodine-131 ($^{131}$I). It will be understood that, in a compound as provided herein, any hydrogen can be $^2$H, as example, or any carbon can be $^{13}$C, as example, or any nitrogen can be $^{15}$N, as example, or any oxygen can be $^{18}$O, as example, where feasible according to the judgment of one of ordinary skill in the art.

The term "isotopic enrichment" refers to the percentage of incorporation of a less prevalent isotope (e.g., D for deuterium or hydrogen-2) of an element at a given position in a molecule in the place of a more prevalent isotope (e.g., $^1$H for protium or hydrogen-1) of the element. As used herein, when an atom at a particular position in a molecule is designated as a particular less prevalent isotope, it is understood that the abundance of that isotope at that position is substantially greater than its natural abundance.

The term "isotopic enrichment factor" refers the ratio between the isotopic abundance in an isotopically enriched compound and the natural abundance of a specific isotope.

The term "hydrogen" or the symbol "H" refers to the composition of naturally occurring hydrogen isotopes, which include protium ($^1$H), deuterium (2H or D), and tritium (3H), in their natural abundances. Protium is the most common hydrogen isotope having a natural abundance of more than 99.98%. Deuterium is a less prevalent hydrogen isotope having a natural abundance of about 0.0156%.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156% on average, deuterium enrichment at any position in a compound synthesized using non-enriched starting materials is about 0.0156% on average. As used herein, when a particular position in an isotopically enriched compound is designated as having deuterium, it is understood that the abundance of deuterium at that position in the compound is substantially greater than its natural abundance (0.0156%).

The term "carbon" or the symbol "C" refers to the composition of naturally occurring carbon isotopes, which include carbon-12 ($^{12}$C) and carbon-13 ($^{13}$C) in their natural abundances. Carbon-12 is the most common carbon isotope having a natural abundance of more than 98.89%. Carbon-13 is a less prevalent carbon isotope having a natural abundance of about 1.11%.

The term "carbon-13 enrichment" or "$^{13}$C enrichment" refers to the percentage of incorporation of carbon-13 at a given position in a molecule in the place of carbon. For example, carbon-13 enrichment of 10% at a given position means that 10% of molecules in a given sample contain carbon-13 at the specified position. Because the naturally occurring distribution of carbon-13 is about 1.11% on average, carbon-13 enrichment at any position in a compound synthesized using non-enriched starting materials is about 1.11% on average. As used herein, when a particular position in an isotopically enriched compound is designated as having carbon-13, it is understood that the abundance of carbon-13 at that position in the compound is substantially greater than its natural abundance (1.11%).

The terms "substantially pure" and "substantially homogeneous" mean sufficiently homogeneous to appear free of readily detectable impurities as determined by standard analytical methods used by one of ordinary skill in the art, including, but not limited to, thin layer chromatography (TLC), gel electrophoresis, high performance liquid chromatography (HPLC), gas chromatography (GC), nuclear magnetic resonance (NMR), and mass spectrometry (MS); or sufficiently pure such that further purification would not detectably alter the physical, chemical, biological, and/or pharmacological properties, such as enzymatic and biological activities, of the substance. In certain embodiments, "substantially pure" or "substantially homogeneous" refers to a collection of molecules, wherein at least about 50%, at least about 70%, at least about 80%, at least about 90%, at least about 95%, at least about 98%, at least about 99%, or at least about 99.5% by weight of the molecules are a single compound, including a single enantiomer, a racemic mixture, or a mixture of enantiomers, as determined by standard analytical methods. As used herein, when an atom at a particular position in an isotopically enriched molecule is designated as a particular less prevalent isotope, a molecule that contains other than the designated isotope at the specified position is an impurity with respect to the isotopically enriched compound. Thus, for a deuterated compound that has an atom at a particular position designated as deuterium, a compound that contains a protium at the same position is an impurity.

The term "solvate" refers to a complex or aggregate formed by one or more molecules of a solute, e.g., a compound provided herein, and one or more molecules of a solvent, which present in stoichiometric or non-stoichiometric amount. Suitable solvents include, but are not limited to, water, methanol, ethanol, n-propanol, isopropanol, acetone, acetic acid, and hexane. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The phrase "a non-hygroscopic crystalline salt of the Compound or an isotopic variant thereof with an acid; or a pharmaceutically acceptable solvate thereof" has the same meaning as the phrase "(i) a non-hygroscopic crystalline salt of the Compound with an acid; (ii) a non-hygroscopic crystalline salt of a pharmaceutically acceptable solvate of the Compound with an acid; or (iii) a non-hygroscopic crystalline salt of an acid with an isotopic variant of the Compound; or (iv) a non-hygroscopic crystalline salt of a pharmaceutically acceptable solvate of an acid with an isotopic variant of the Compound."

Non-Hygroscopic Crystalline Salts of the Compound

The Compound, (1r,4r)-N$^1$-(5-chloro-4-(5-(cyclopropylmethyl)-1-methyl-1H-pyrazol-4-yl)pyrimidin-2-yl)cyclohexane-1,4-diamine, has the structure of:

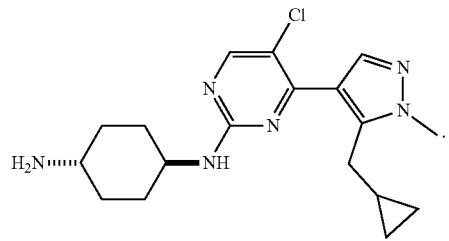 [SMILES: Cn1ncc(-c2nc(N[C@H]3CC[C@H](N)CC3)ncc2Cl)c1CC1CC1]

The Compound is a CK1α, CDK7, and CDK9 inhibitor. Minzel et al., Cell 2018, 175, 1-15. The Compound can be prepared according to the procedures described in Minzel et al., Cell 2018, 175, 1-15; or U.S. Pat. Appl. Publ. No. 2018/0214447 A1; the disclosure of each of which is incorporated herein by reference in its entirety.

In one embodiment, provided herein is a non-hygroscopic crystalline salt of (1r,4r)-N$^1$-(5-chloro-4-(5-(cyclopropylmethyl)-1-methyl-1H-pyrazol-4-yl)pyrimidin-2-yl)cyclohexane-1,4-diamine or an isotopic variant thereof with an acid; or a pharmaceutically acceptable solvate thereof.

In certain embodiments, the molar ratio of the Compound versus the acid in the crystalline salt provided herein is ranging from about 0.5 to about 3 or from about 0.5 to about 2.5. In certain embodiments, the molar ratio of the Compound versus the acid in the crystalline salt provided herein is about 0.5, about 0.6, about 0.7, about 0.8, about 0.9, about 1, about 1.1, about 1.2, about 1.4, about 1.5, about 1.6, about 1.8, about 2, about 2.2, about 2.4, about 2.6, about 2.8, or about 3. In certain embodiments, the molar ratio of the Compound versus the acid in the crystalline salt provided herein is about 1. In certain embodiments, the molar ratio of the Compound versus the acid in the crystalline salt provided herein is about 2.

In certain embodiments, the acid is acetic acid, adipic acid, benzoic acid, fumaric acid, glycolic acid, hippuric acid, lactic acid, maleic acid, malic acid, methanesulfonic acid, succinic acid, sulfuric acid, tartaric acid, thiocyanic acid, or p-toluenesulfonic acid. In certain embodiments, the acid is adipic acid, benzoic acid, or p-toluenesulfonic acid. In certain embodiments, the acid is adipic acid. In certain embodiments, the acid is benzoic acid. In certain embodiments, the acid is p-toluenesulfonic acid.

In certain embodiments, the non-hygroscopic crystalline salt provided herein has a solubility of no greater than 10 mg/mL, no greater than 5 mg/mL, or no greater than 2 mg/mL in water at 25° C.

In certain embodiments, the non-hygroscopic crystalline salt provided herein has no greater than 5%, no greater than 4%, no greater than 3%, no greater than 2%, or no greater than 1% weight gain from 5 to 95% relative humidity (RH) at 25° C. In certain embodiments, the non-hygroscopic crystalline salt provided herein has no greater than 5% weight gain from 5 to 95% RH at 25° C. In certain embodiments, the non-hygroscopic crystalline salt provided herein has no greater than 4% weight gain from 5 to 95% RH at 25° C. In certain embodiments, the non-hygroscopic crystalline salt provided herein has no greater than 3% weight gain from 5 to 95% RH at 25° C. In certain embodiments, the non-hygroscopic crystalline salt provided herein has no greater than 2% weight gain from 5 to 95% RH at 25° C. In certain embodiments, the non-hygroscopic crystalline salt provided herein has no greater than 1% weight gain from 5 to 95% RH at 25° C. weight gain from 5 to 95% RH at 25° C.

In another embodiment, provided herein is a crystalline acetate salt of (1r,4r)-N$^1$-(5-chloro-4-(5-(cyclopropylmethyl)-1-methyl-1H-pyrazol-4-yl)pyrimidin-2-yl)cyclohexane-1,4-diamine or an isotopic variant thereof; or a pharmaceutically acceptable solvate thereof.

In certain embodiments, the molar ratio of the Compound versus acetic acid in the crystalline acetate salt provided herein is ranging from about 0.5 to about 3 or from about 0.5 to about 2.5. In certain embodiments, the molar ratio of the Compound versus acetic acid in the crystalline acetate salt provided herein is about 0.5, about 0.6, about 0.7, about 0.8, about 0.9, about 1, about 1.1, about 1.2, about 1.4, about 1.5, about 1.6, about 1.8, about 2, about 2.2, about 2.4, about 2.6, about 2.8, or about 3. In certain embodiments, the molar ratio of the Compound versus acetic acid in the crystalline acetate salt provided herein is about 1. In certain embodiments, the molar ratio of the Compound versus acetic acid in the crystalline acetate salt provided herein is about 2.

In one embodiment, the crystalline acetate salt provided herein comprises about one molar equivalent of the Compound and about one molar equivalent of acetic acid. In another embodiment, the crystalline acetate salt provided herein comprises about one molar equivalent of the Compound and about two molar equivalents of acetic acid. In certain embodiments, the molar ratio of the Compound versus acetic acid in the crystalline acetate salt provided herein is determined by $^1$H NMR spectroscopy. In certain embodiments, the molar ratio of the Compound versus acetic acid in the crystalline acetate salt provided herein is determined by an elemental analysis.

In certain embodiments, the crystalline acetate salt provided herein has an X-ray powder diffractogram substantially as shown in FIG. 1 (the top diffractogram). In certain embodiments, the crystalline acetate salt provided herein has an X-ray powder diffractogram substantially as shown in FIG. 1 (the middle diffractogram).

Figure 2:
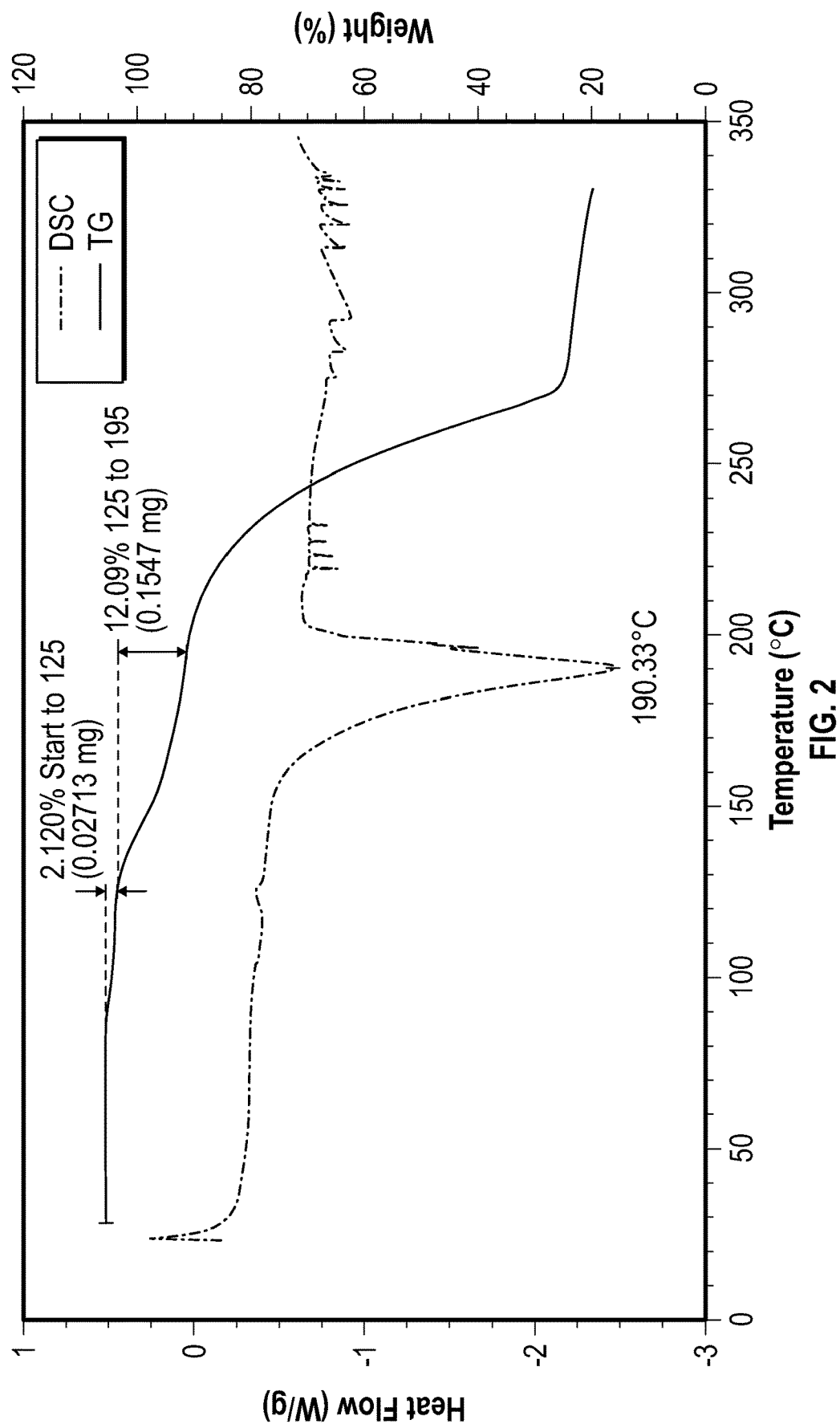
FIG. 2 depicts differential scanning calorimetry (DSC)/thermogravimetry (TGA) thermograms of a crystalline acetate salt of the Compound.
Figure 3:
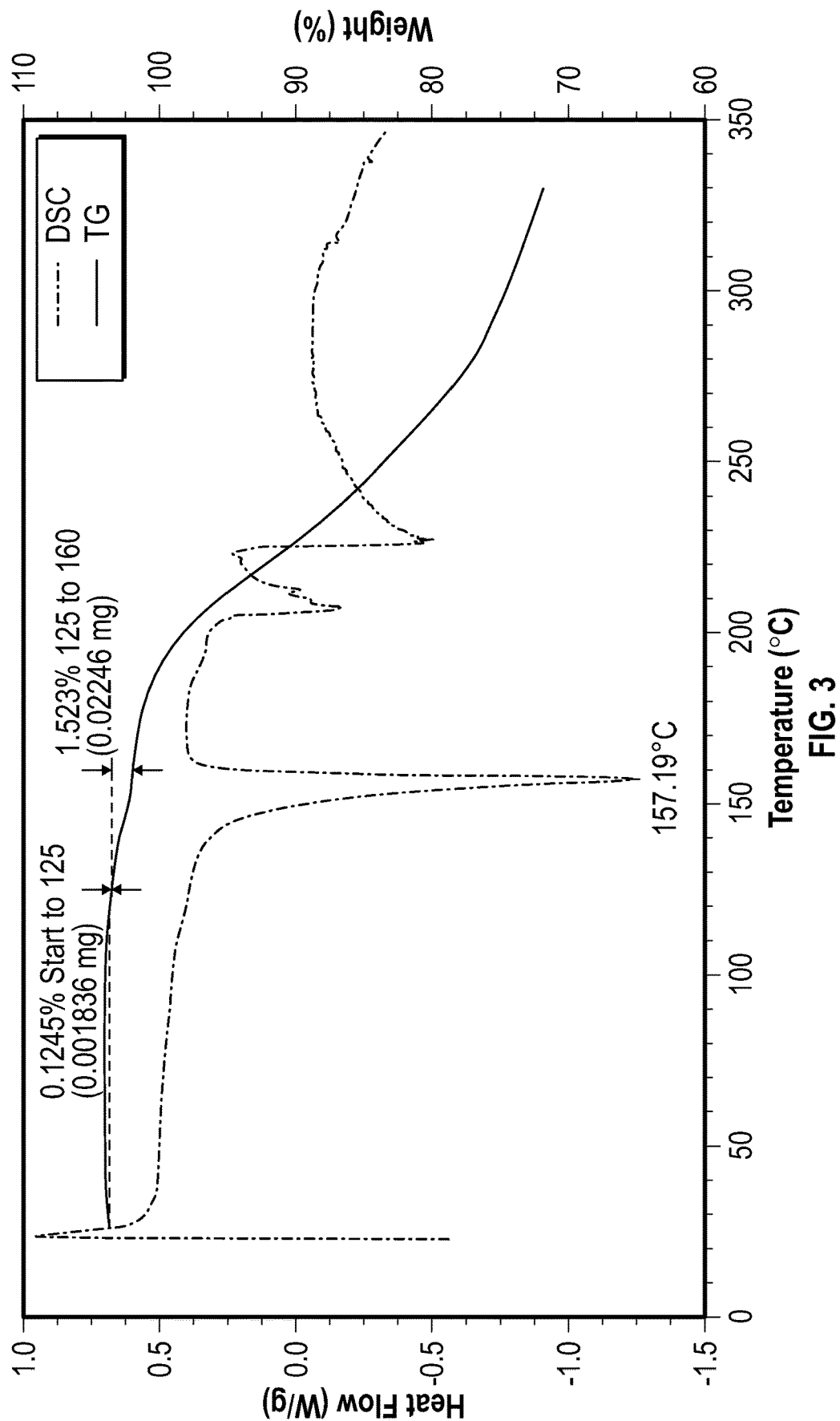
FIG. 3 depicts DSC/TGA thermograms of a crystalline adipate salt of the Compound.

In certain embodiments, the crystalline acetate salt provided herein has a DSC thermogram comprising an endothermic peak at about 190° C. In certain embodiments, the crystalline acetate salt provided herein has a DSC thermogram comprising an endothermic peak at 190±3° C. In certain embodiments, the crystalline acetate salt provided herein has a DSC thermogram substantially as shown in FIG. 2. In certain embodiments, the crystalline acetate salt provided herein has a melting point of about 190° C.

In certain embodiments, the crystalline acetate salt provided herein has a thermogravimetric (TGA) thermogram showing a weight loss of about 2% from room temperature to 125° C. In certain embodiments, the crystalline acetate salt provided herein has a TGA thermogram showing a weight loss of about 12% from room 125° C. to 195° C. In certain embodiments, the crystalline acetate salt provided herein has a TGA thermogram substantially as shown in FIG. 2.

In certain embodiments, the crystalline acetate salt provided herein is solvated. In certain embodiments, the crystalline acetate salt provided herein is an acetone solvate. In certain embodiments, the crystalline acetate salt provided herein is a hydrate.

In yet another embodiment, provided herein is a crystalline adipate salt of (1r,4r)-N$^1$-(5-chloro-4-(5-(cyclopropylmethyl)-1-methyl-1H-pyrazol-4-yl)pyrimidin-2-yl)cyclohexane-1,4-diamine or an isotopic variant thereof; or a pharmaceutically acceptable solvate thereof.

In certain embodiments, the molar ratio of the Compound versus adipic acid in the crystalline adipate salt provided herein is ranging from about 0.25 to about 1.5 or from about 0.5 to about 1. In certain embodiments, the molar ratio of the Compound versus adipic acid in the crystalline adipate salt provided herein is about 0.25, about 0.3, about 0.4, about 0.5, about 0.6, about 0.7, about 0.8, about 0.9, about 1, about 1.1, about 1.2, about 1.3, about 1.4, or about 1.5. In certain embodiments, the molar ratio of the Compound versus adipic acid in the crystalline adipate salt provided herein is about 0.5. In certain embodiments, the molar ratio of the Compound versus adipic acid in the crystalline adipate salt provided herein is about 1.

In one embodiment, the crystalline adipate salt provided herein comprises about two molar equivalents of the Compound and about one molar equivalent of adipic acid. In one embodiment, the crystalline adipate salt provided herein comprises about one molar equivalent of the Compound and about one molar equivalent of adipic acid. In certain embodiments, the molar ratio of the Compound versus adipic acid in the crystalline adipate salt provided herein is determined by $^1$H NMR spectroscopy. In certain embodiments, the molar ratio of the Compound versus adipic acid in the crystalline adipate salt provided herein is determined by an elemental analysis.

Figure 24:
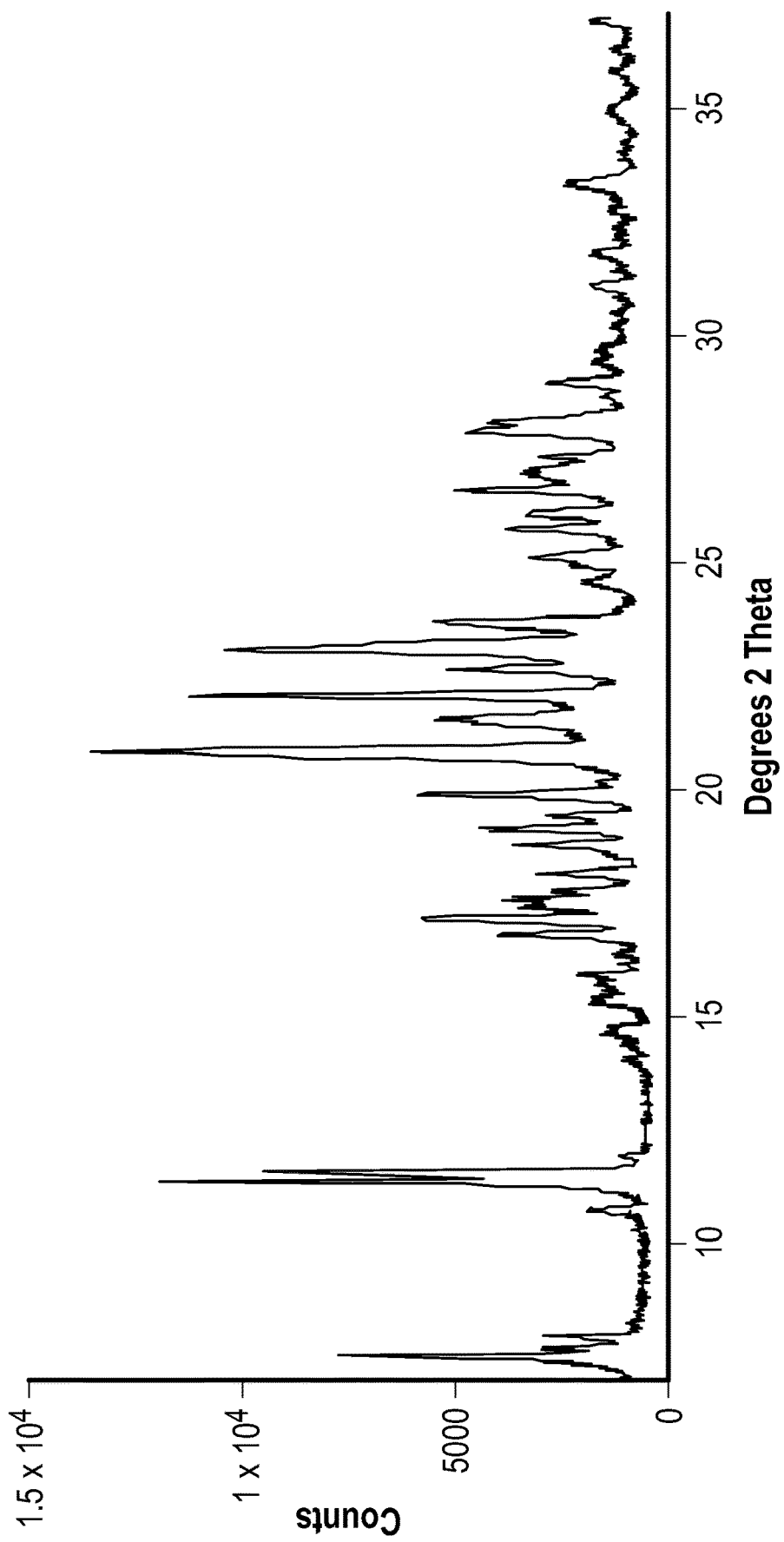
FIG. 24 depicts an X-ray powder diffractogram of a non-hygroscopic crystalline adipate salt of the Compound.

In certain embodiments, the crystalline adipate salt provided herein has an X-ray powder diffractogram substantially as shown in FIG. 24.

Figure 25:
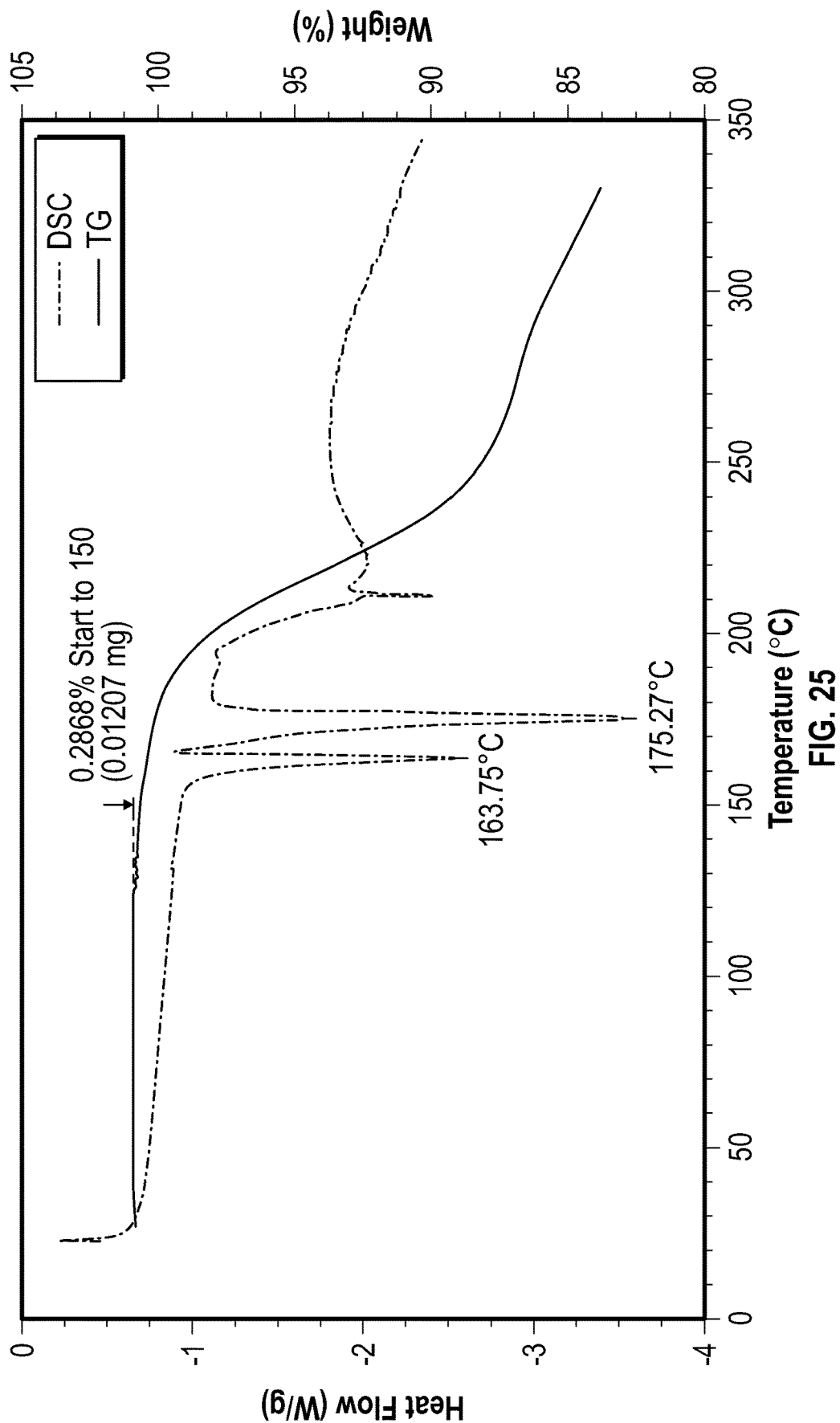
FIG. 25 depicts DSC/TGA thermograms of a non-hygroscopic crystalline adipate salt of the Compound.

In certain embodiments, the crystalline adipate salt provided herein has a DSC thermogram comprising an endothermic peak at about 164° C. In certain embodiments, the crystalline adipate salt provided herein has a DSC thermogram comprising an endothermic peak at 164±3° C. In certain embodiments, the crystalline adipate salt provided herein has a DSC thermogram comprising an endothermic peak at about 175° C. In certain embodiments, the crystalline adipate salt provided herein has a DSC thermogram comprising an endothermic peak at 175±3° C. In certain embodiments, the crystalline adipate salt provided herein has a DSC thermogram substantially as shown in FIG. 25. In certain embodiments, the crystalline adipate salt provided herein has a melting point of about 164° C.

In certain embodiments, the crystalline adipate salt provided herein has a TGA thermogram showing a weight loss of about 0.3% from room temperature to 150° C. In certain embodiments, the crystalline adipate salt provided herein has a TGA thermogram substantially as shown in FIG. 25.

Figure 26:
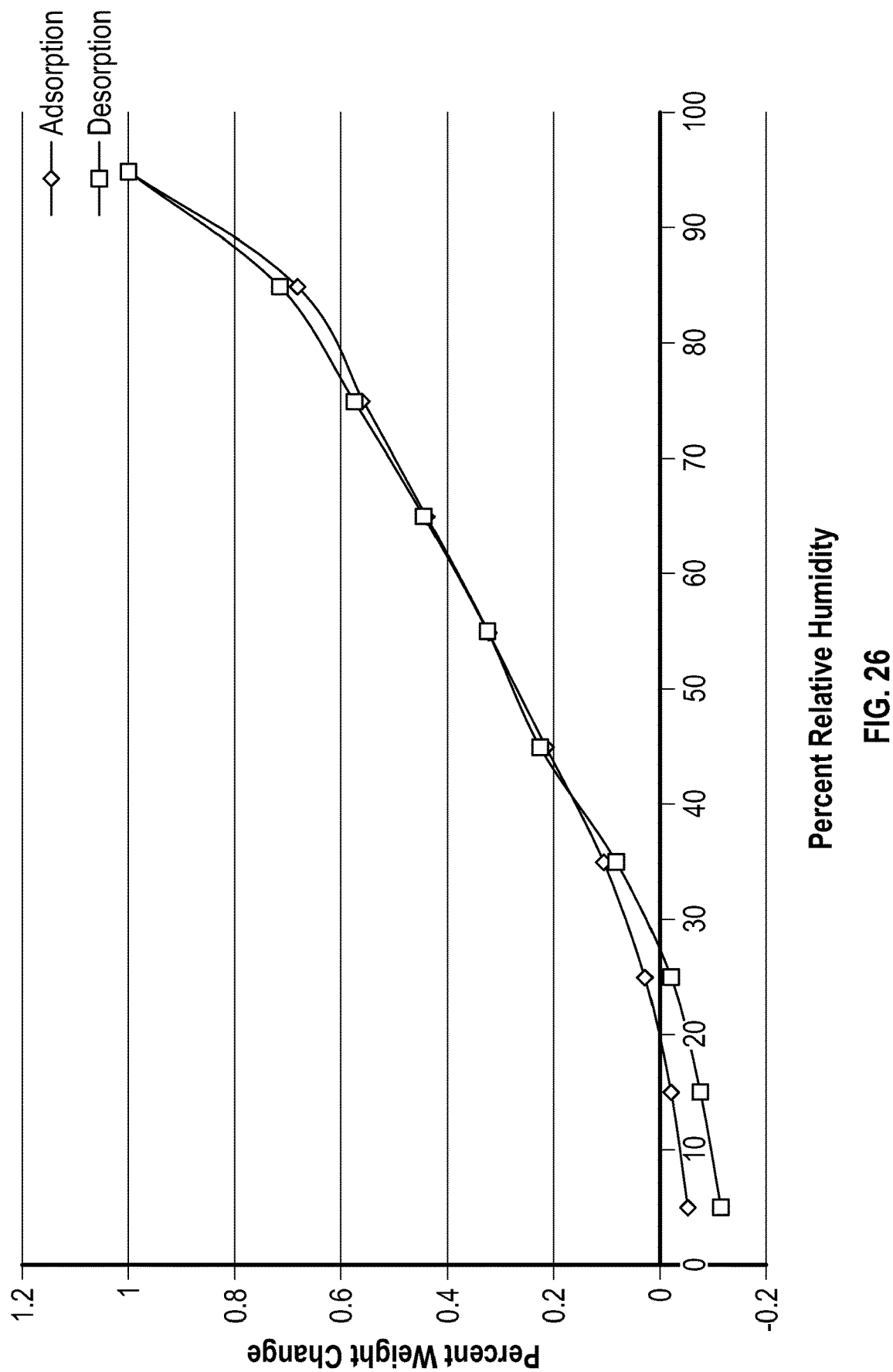
FIG. 26 depicts a dynamic vapor sorption (DVS) isotherm graph of a non-hygroscopic crystalline adipate salt of the Compound.

In certain embodiments, the crystalline adipate salt provided herein has a dynamic vapor sorption (DVS) isotherm graph showing a weight loss of about 0.05% upon drying at 5% RH. In certain embodiments, the crystalline adipate salt provided herein has a DVS isotherm graph showing a weight gain of about 1% from 5 to 95% RH. In certain embodiments, the crystalline adipate salt provided herein has a DVS isotherm graph showing a weight loss of about 1% from 95 to 5% RH. In certain embodiments, the crystalline adipate salt provided herein has a DVS isotherm graph substantially as shown in FIG. 26.

In certain embodiments, the crystalline adipate salt provided herein has no greater than 5%, no greater than 4%, no greater than 3%, no greater than 2%, or no greater than 1% weight gain from 5 to 95% relative humidity (RH) at 25° C. In certain embodiments, the crystalline adipate salt provided herein has no greater than 5% weight gain from 5 to 95% RH at 25° C. In certain embodiments, the crystalline adipate salt provided herein has no greater than 4% weight gain from 5 to 95% RH at 25° C. In certain embodiments, the crystalline adipate salt provided herein has no greater than 3% weight gain from 5 to 95% RH at 25° C. In certain embodiments, the crystalline adipate salt provided herein has no greater than 2% weight gain from 5 to 95% RH at 25° C. In certain embodiments, the crystalline adipate salt provided herein has no greater than 1% weight gain from 5 to 95% RH at 25° C. weight gain from 5 to 95% RH at 25° C.

In certain embodiments, the crystalline adipate salt provided herein is unsolvated. In certain embodiments, the crystalline adipate salt has a solubility of about 15 mg/mL in water at 25° C.

In yet another embodiment, provided herein is a crystalline benzoate salt of (1r,4r)-N$^1$-(5-chloro-4-(5-(cyclopropylmethyl)-1-methyl-1H-pyrazol-4-yl)pyrimidin-2-yl)cyclohexane-1,4-diamine or an isotopic variant thereof; or a pharmaceutically acceptable solvate thereof.

In certain embodiments, the molar ratio of the Compound versus benzoic acid in the crystalline benzoate salt provided herein is ranging from about 0.5 to about 3 or from about 0.5 to about 2.5. In certain embodiments, the molar ratio of the Compound versus benzoic acid in the crystalline benzoate salt provided herein is about 0.5, about 0.6, about 0.7, about 0.8, about 0.9, about 1, about 1.1, about 1.2, about 1.4, about 1.5, about 1.6, about 1.8, about 2, about 2.2, about 2.4, about 2.6, about 2.8, or about 3. In certain embodiments, the molar ratio of the Compound versus benzoic acid in the crystalline benzoate salt provided herein is about 1. In certain embodiments, the molar ratio of the Compound versus benzoic acid in the crystalline benzoate salt provided herein is about 2.

In one embodiment, the crystalline benzoate salt provided herein comprises about one molar equivalent of the Compound and about one molar equivalent of benzoic acid. In another embodiment, the crystalline benzoate salt provided herein comprises about one molar equivalent of the Compound and about two molar equivalents of benzoic acid. In certain embodiments, the molar ratio of the Compound versus benzoic acid in the crystalline benzoate salt provided herein is determined by $^1$H NMR spectroscopy. In certain embodiments, the molar ratio of the Compound versus benzoic acid in the crystalline benzoate salt provided herein is determined by an elemental analysis.

Figure 29:
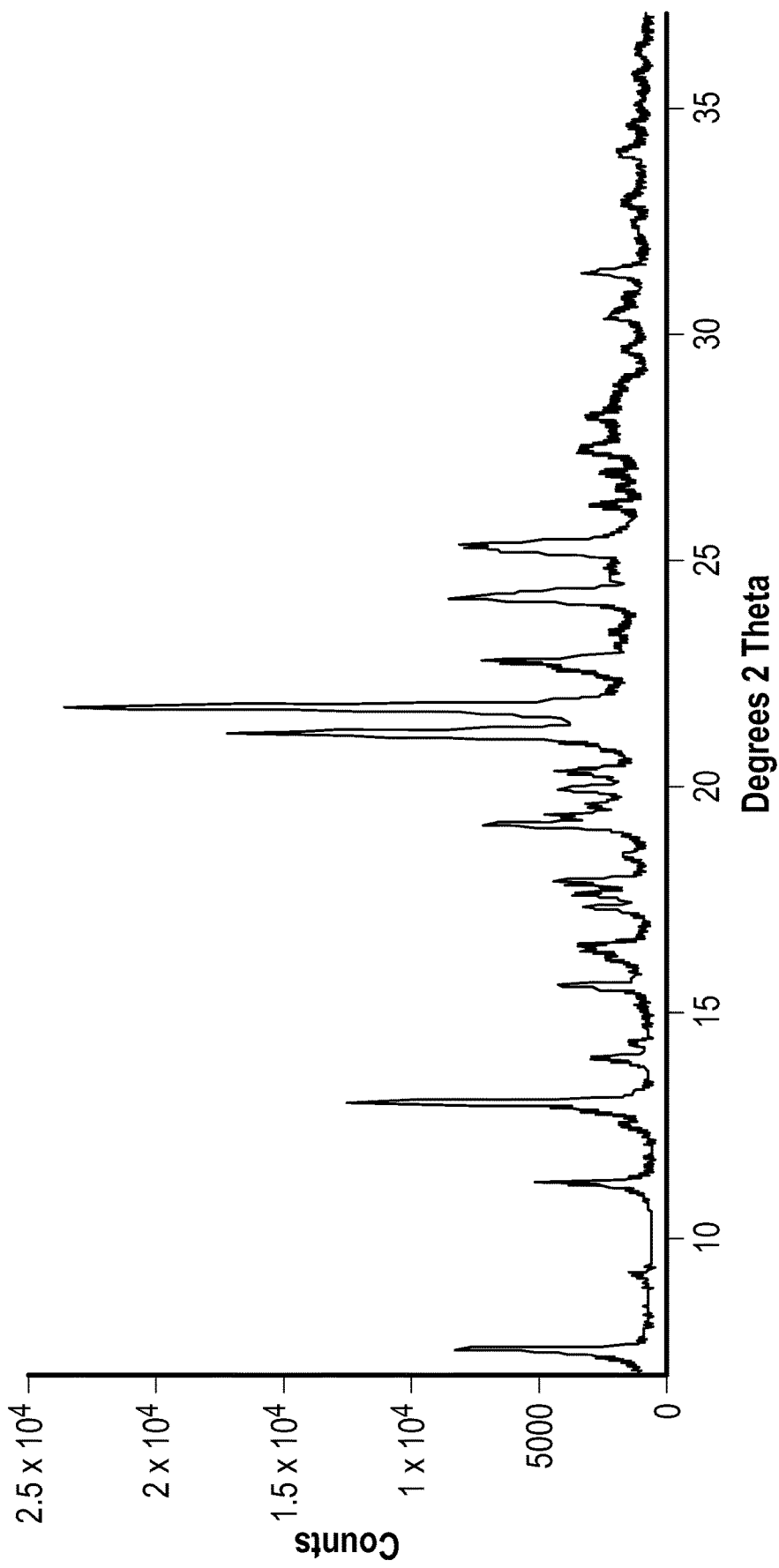
FIG. 29 depicts an X-ray powder diffractogram of a crystalline benzoate salt of the Compound.

In certain embodiments, the crystalline benzoate salt provided herein has an X-ray powder diffractogram substantially as shown in FIG. 29.

Figure 30:
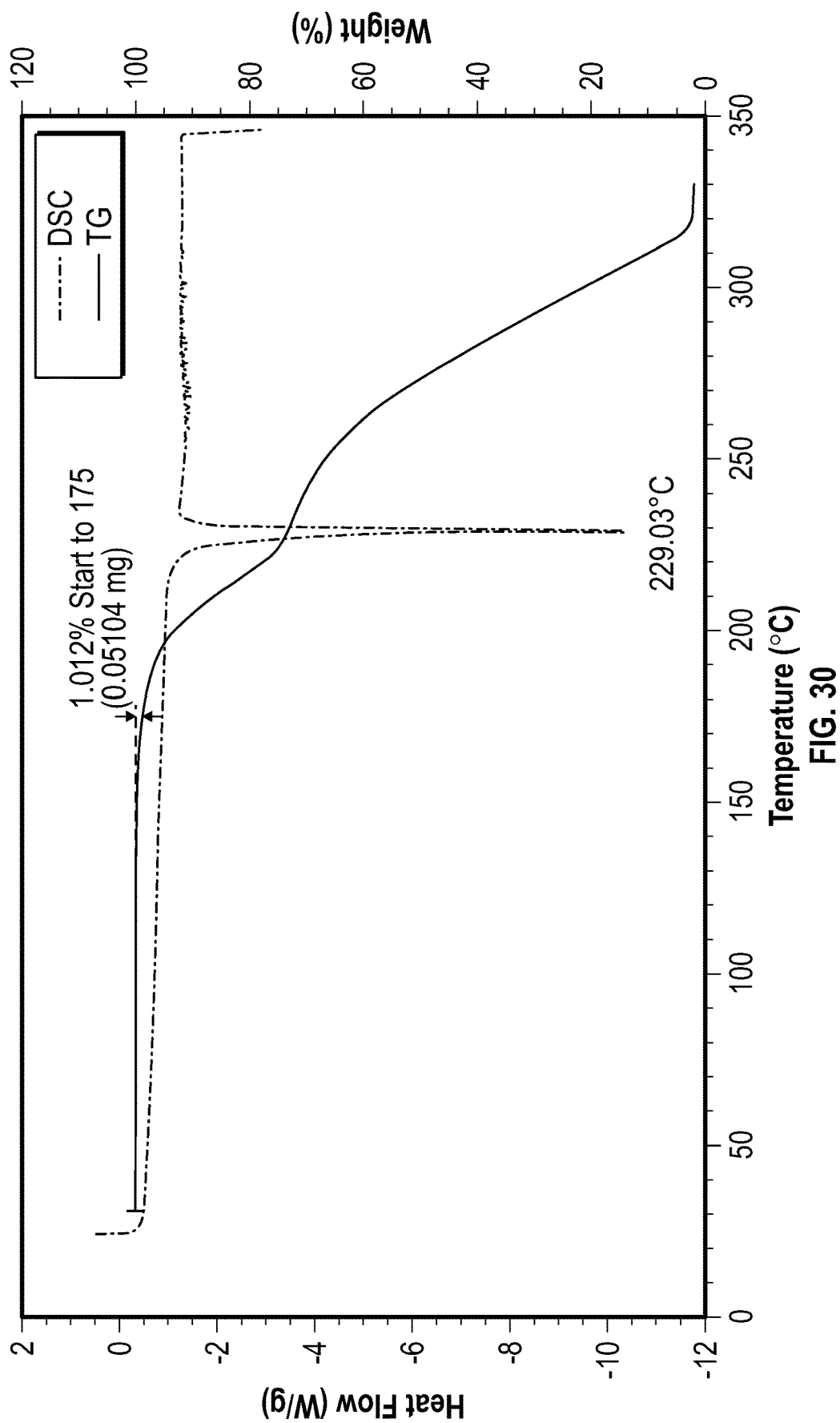
FIG. 30 depicts DSC/TGA thermograms of a crystalline benzoate salt of the Compound.

In certain embodiments, the crystalline benzoate salt provided herein has a DSC thermogram comprising an endothermic peak at about 229° C. In certain embodiments, the crystalline benzoate salt provided herein has a DSC thermogram comprising an endothermic peak at 229±3° C. In certain embodiments, the crystalline benzoate salt provided herein has a DSC thermogram substantially as shown in FIG. 30.

In certain embodiments, the crystalline benzoate salt provided herein has a TGA thermogram showing a weight loss of about 1% from room temperature to 175° C. In certain embodiments, the crystalline benzoate salt provided herein has a TGA thermogram substantially as shown in FIG. 30.

Figure 31:
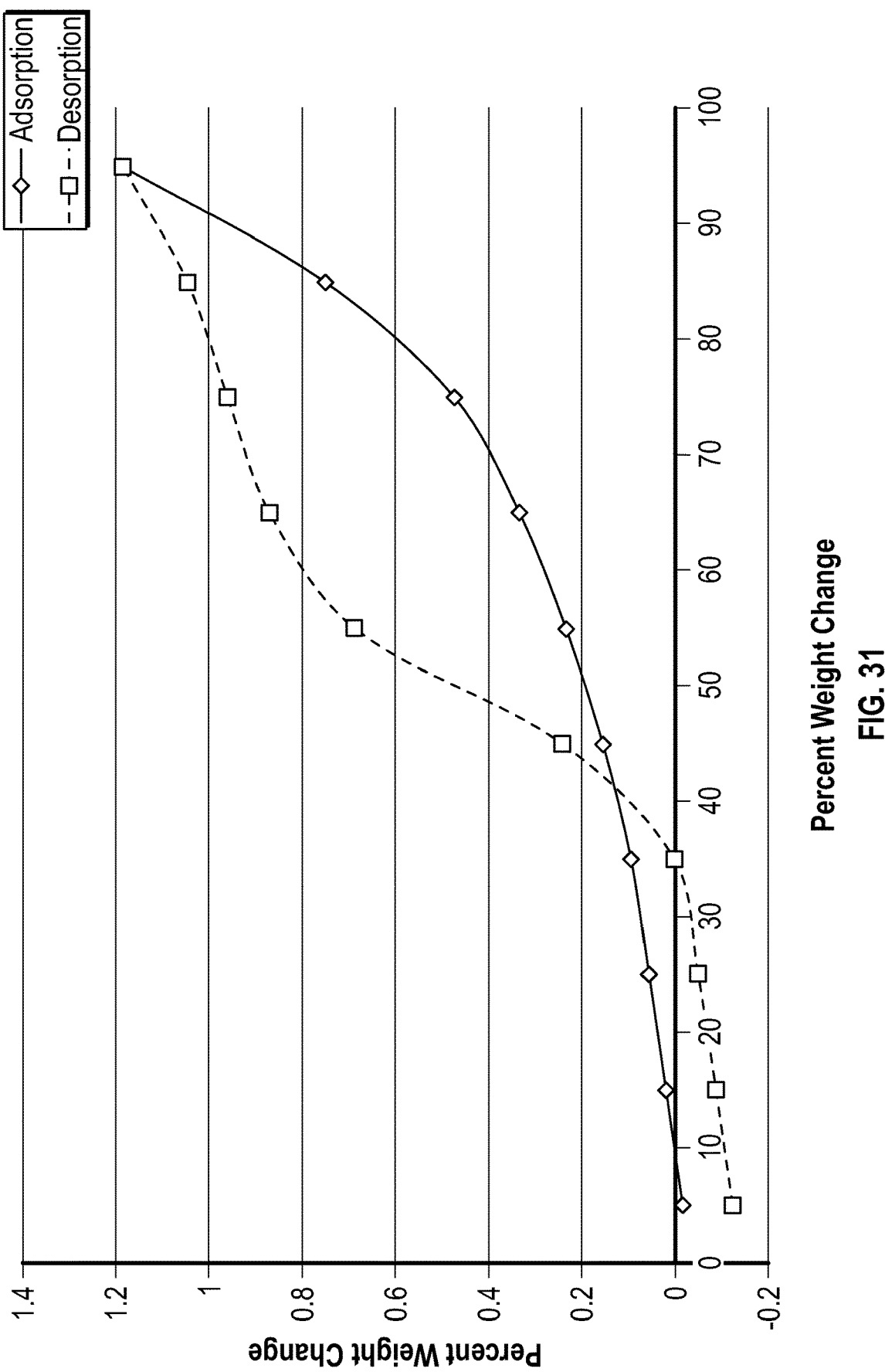
FIG. 31 depicts a DVS isotherm graph of a crystalline benzoate salt of the Compound.

In certain embodiments, the crystalline benzoate salt provided herein has a DVS isotherm graph showing a weight loss of about 0.02% upon drying at 5% RH. In certain embodiments, the crystalline benzoate salt provided herein has a DVS isotherm graph showing a weight gain of about 1.2% from 5 to 95% RH. In certain embodiments, the crystalline benzoate salt provided herein has a DVS isotherm graph showing a weight loss of about 1.3% from 95 to 5% RH. In certain embodiments, the crystalline benzoate salt provided herein has a DVS isotherm graph substantially as shown in FIG. 31.

In certain embodiments, the crystalline benzoate salt provided herein has no greater than 5%, no greater than 4%, no greater than 3%, no greater than 2%, or no greater than 1% weight gain from 5 to 95% relative humidity (RH) at 25° C. In certain embodiments, the crystalline benzoate salt provided herein has no greater than 5% weight gain from 5 to 95% RH at 25° C. In certain embodiments, the crystalline benzoate salt provided herein has no greater than 4% weight gain from 5 to 95% RH at 25° C. In certain embodiments, the crystalline benzoate salt provided herein has no greater than 3% weight gain from 5 to 95% RH at 25° C. In certain embodiments, the crystalline benzoate salt provided herein has no greater than 2% weight gain from 5 to 95% RH at 25° C. In certain embodiments, the crystalline benzoate salt provided herein has no greater than 1% weight gain from 5 to 95% RH at 25° C. weight gain from 5 to 95% RH at 25° C.

In certain embodiments, the crystalline benzoate salt provided herein is unsolvated. In certain embodiments, the crystalline benzoate salt has a solubility of no greater than 1 mg/mL in water at 25° C.

In yet another embodiment, provided herein is a crystalline fumarate salt of (1r,4r)-N$^1$-(5-chloro-4-(5-(cyclopropylmethyl)-1-methyl-1H-pyrazol-4-yl)pyrimidin-2-yl)cyclohexane-1,4-diamine or an isotopic variant thereof; or a pharmaceutically acceptable solvate thereof.

In certain embodiments, the molar ratio of the Compound versus fumaric acid in the crystalline fumarate salt provided herein is ranging from about 0.25 to about 1.5 or from about 0.5 to about 1. In certain embodiments, the molar ratio of the Compound versus fumaric acid in the crystalline fumarate salt provided herein is about 0.25, about 0.3, about 0.4, about 0.5, about 0.6, about 0.7, about 0.8, about 0.9, about 1, about 1.1, about 1.2, about 1.3, about 1.4, or about 1.5. In certain embodiments, the molar ratio of the Compound versus fumaric acid in the crystalline fumarate salt provided herein is about 0.5. In certain embodiments, the molar ratio of the Compound versus fumaric acid in the crystalline fumarate salt provided herein is about 1.

In one embodiment, the crystalline fumarate salt provided herein comprises about two molar equivalents of the Compound and about one molar equivalent of fumaric acid. In another embodiment, the crystalline fumarate salt provided herein comprises about one molar equivalent of the Compound and about one molar equivalent of fumaric acid. In certain embodiments, the molar ratio of the Compound versus fumaric acid in the crystalline fumarate salt provided herein is determined by $^1$H NMR spectroscopy. In certain embodiments, the molar ratio of the Compound versus fumaric acid in the crystalline fumarate salt provided herein is determined by an elemental analysis.

Figure 4:
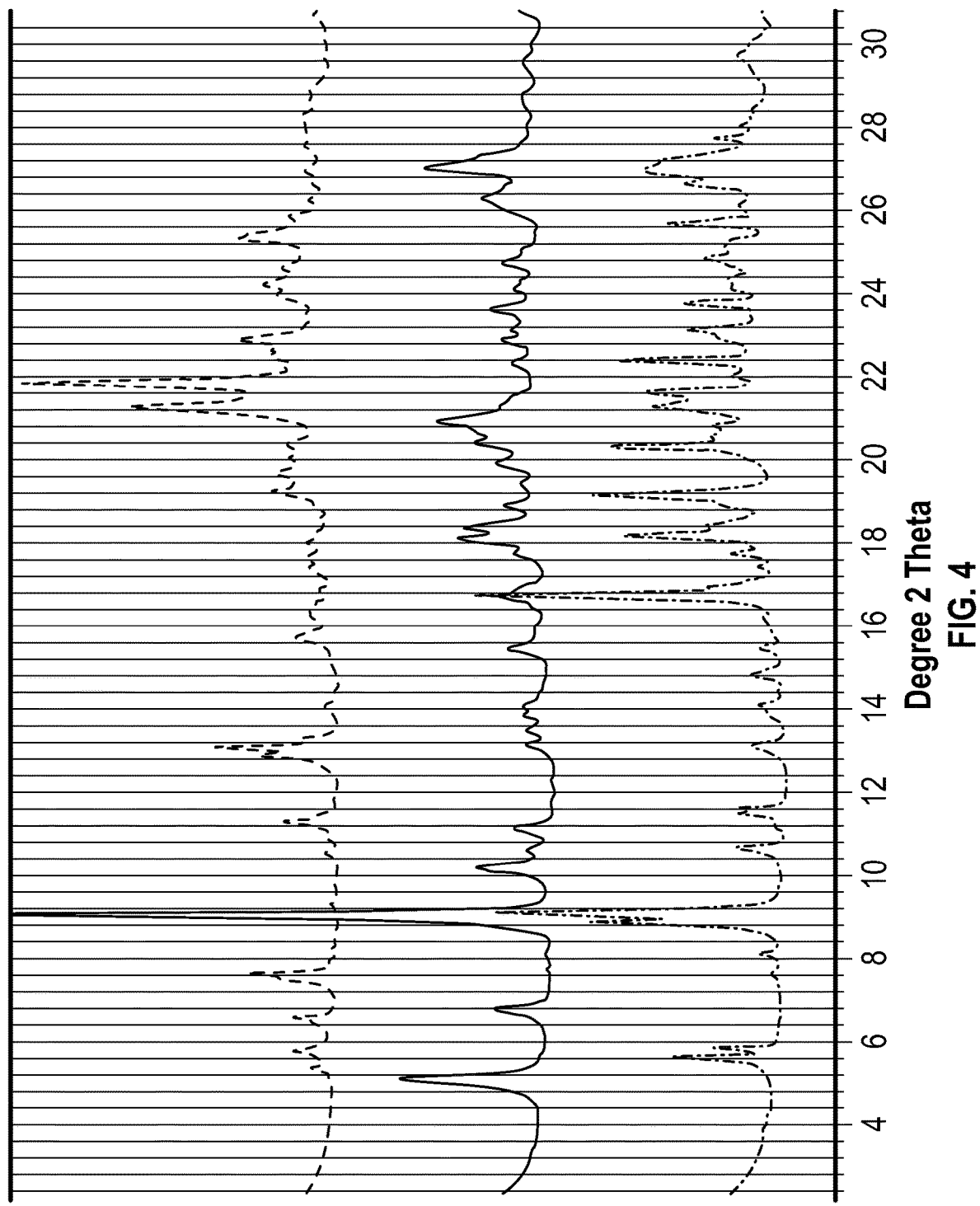
FIG. 4 depicts X-ray powder diffractograms of one crystalline benzoate salt (the top diffractogram) and two crystalline fumarate salts (the middle and bottom diffractograms) of the Compound.
Figure 5:
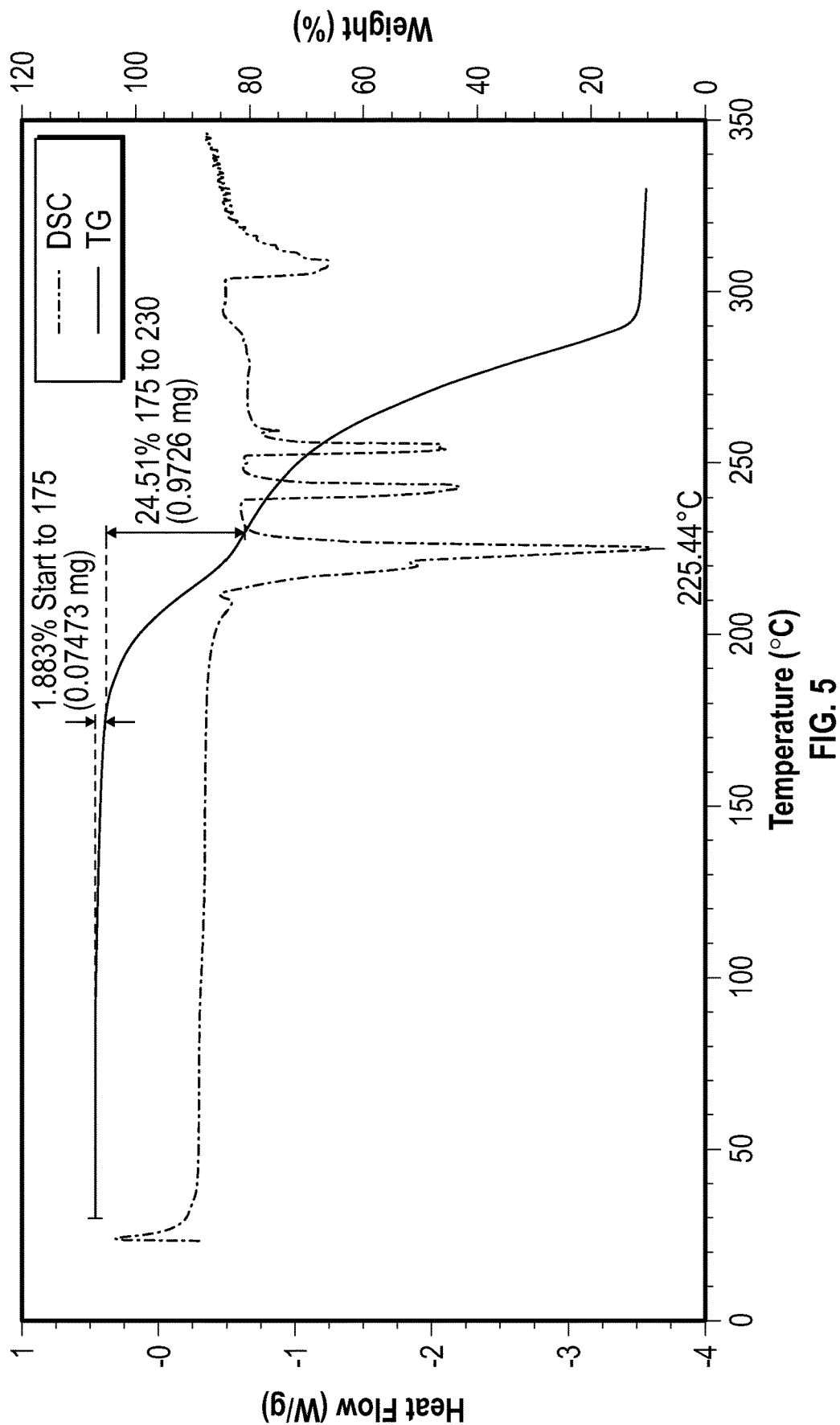
FIG. 5 depicts DSC/TGA thermograms of a crystalline benzoate salt of the Compound.

In certain embodiments, the crystalline fumarate salt provided herein has an X-ray powder diffractogram substantially as shown in FIG. 4 (the middle diffractogram). In certain embodiments, the crystalline fumarate salt provided herein has an X-ray powder diffractogram substantially as shown in FIG. 4 (the bottom diffractogram).

Figure 6:
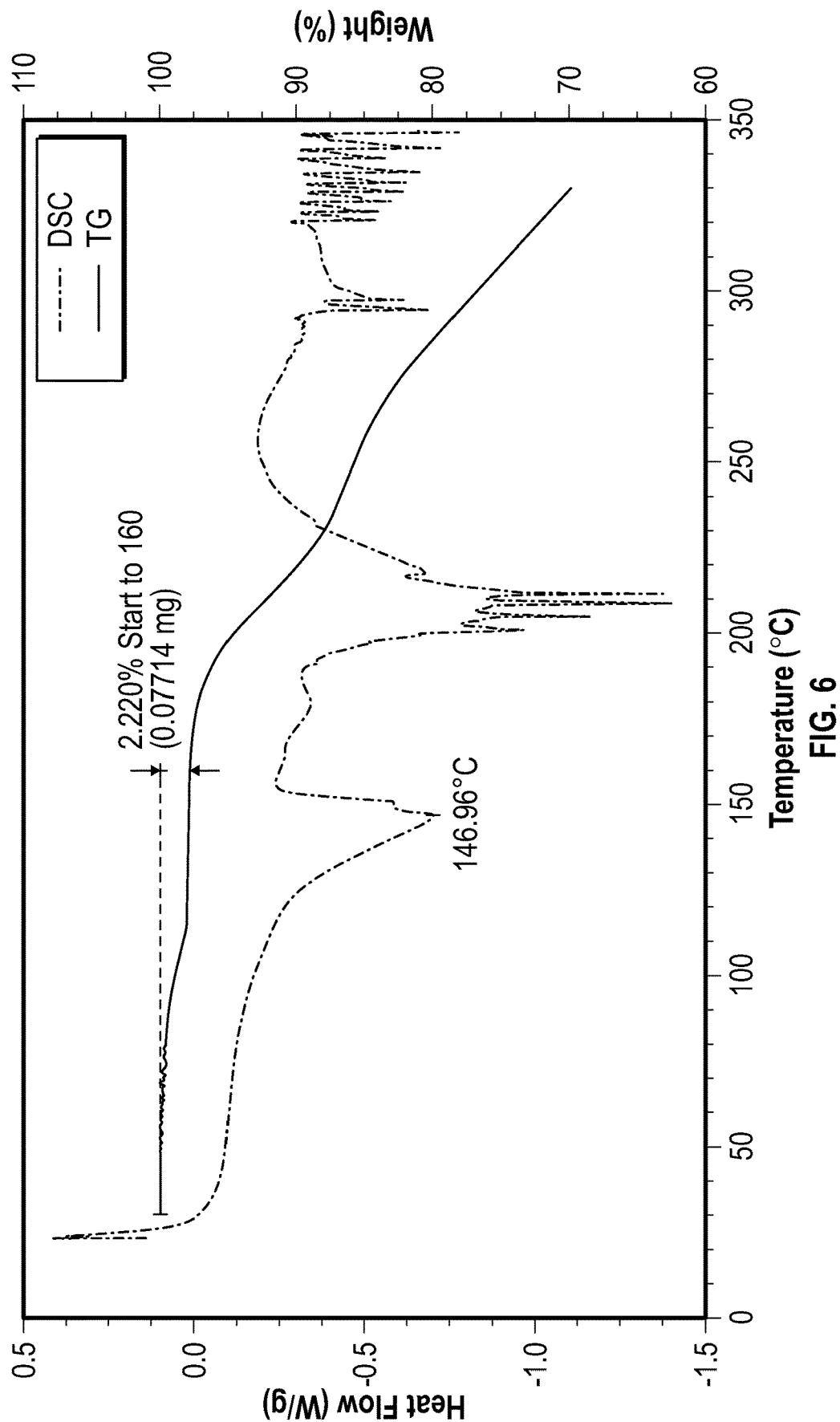
FIG. 6 depicts DSC/TGA thermograms of a crystalline fumerate salt of the Compound.

In certain embodiments, the crystalline fumarate salt provided herein has a DSC thermogram comprising an endothermic peak at about 147° C. In certain embodiments, the crystalline fumarate salt provided herein has a DSC thermogram comprising an endothermic peak at 147±3° C. In certain embodiments, the crystalline fumarate salt provided herein has a DSC thermogram substantially as shown in FIG. 6.

In certain embodiments, the crystalline fumarate salt provided herein has a TGA thermogram showing a weight loss of about 2% from room temperature to 160° C. In certain embodiments, the crystalline fumarate salt provided herein has a TGA thermogram substantially as shown in FIG. 6.

In certain embodiments, the crystalline fumarate salt provided herein is solvated. In certain embodiments, the crystalline fumarate salt provided herein is an acetone solvate. In certain embodiments, the crystalline fumarate salt provided herein is a hydrate.

In yet another embodiment, provided herein is a crystalline glycolate salt of (1r,4r)-N$^1$-(5-chloro-4-(5-(cyclopropylmethyl)-1-methyl-1H-pyrazol-4-yl)pyrimidin-2-yl)cyclohexane-1,4-diamine or an isotopic variant thereof; or a pharmaceutically acceptable solvate thereof.

In certain embodiments, the molar ratio of the Compound versus glycolic acid in the crystalline glycolate salt provided herein is ranging from about 0.5 to about 3 or from about 0.5 to about 2.5. In certain embodiments, the molar ratio of the Compound versus glycolic acid in the crystalline glycolate salt provided herein is about 0.5, about 0.6, about 0.7, about 0.8, about 0.9, about 1, about 1.1, about 1.2, about 1.4, about 1.5, about 1.6, about 1.8, about 2, about 2.2, about 2.4, about 2.6, about 2.8, or about 3. In certain embodiments, the molar ratio of the Compound versus glycolic acid in the crystalline glycolate salt provided herein is about 1. In certain embodiments, the molar ratio of the Compound versus glycolic acid in the crystalline glycolate salt provided herein is about 2.

In one embodiment, the crystalline glycolate salt provided herein comprises about one molar equivalent of the Compound and about one molar equivalent of glycolic acid. In another embodiment, the crystalline glycolate salt provided herein comprises about one molar equivalent of the Compound and about two molar equivalents of glycolic acid. In certain embodiments, the molar ratio of the Compound versus glycolic acid in the crystalline glycolate salt provided herein is determined by $^1$H NMR spectroscopy. In certain embodiments, the molar ratio of the Compound versus glycolic acid in the crystalline glycolate salt provided herein is determined by an elemental analysis.

Figure 7:
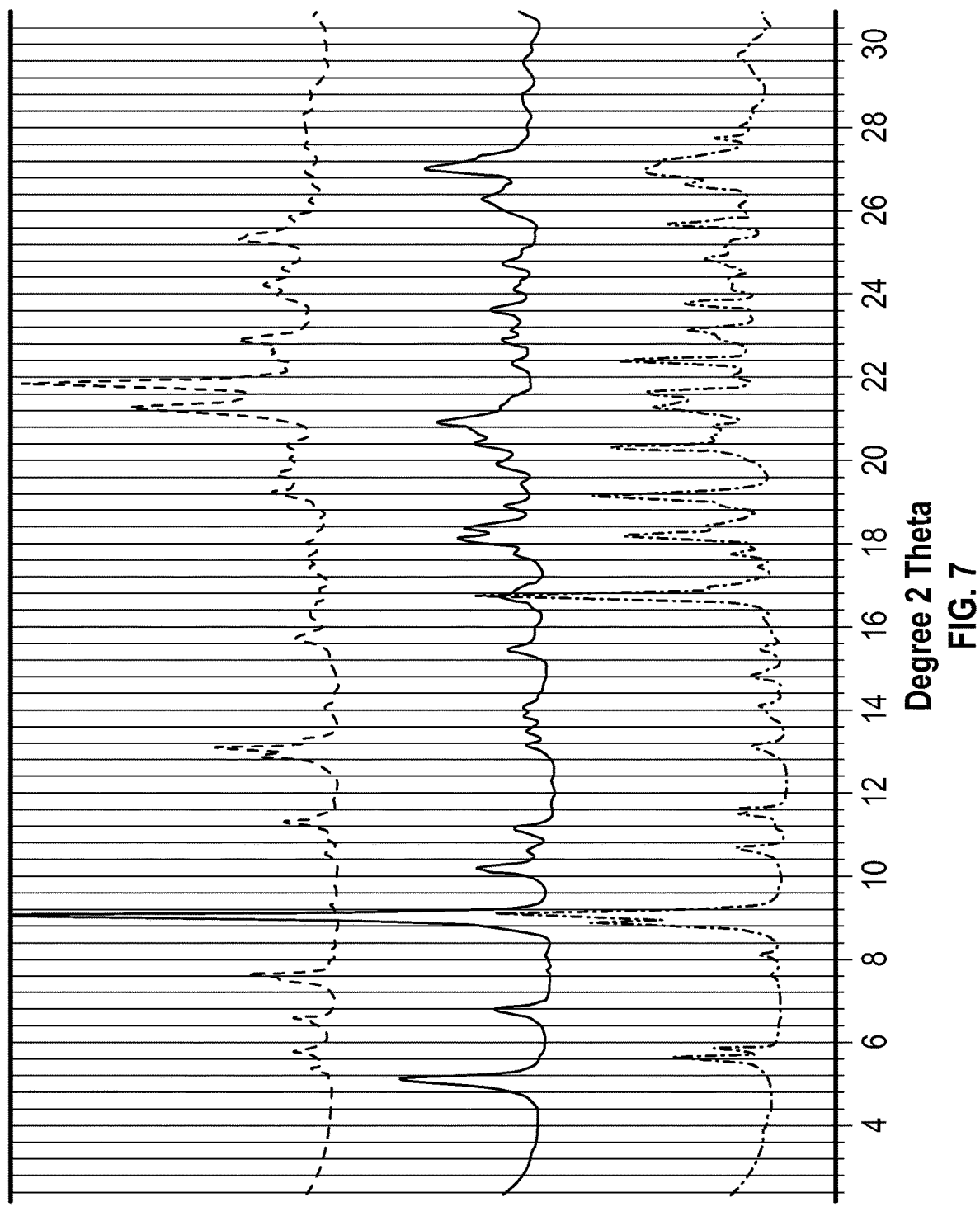
FIG. 7 depicts X-ray powder diffractograms of two crystalline glycolate salts (the top and middle diffractograms) and one crystalline lactate salt (the bottom diffractogram) of the Compound.

In certain embodiments, the crystalline glycolate salt provided herein has an X-ray powder diffractogram substantially as shown in FIG. 7 (the top diffractogram). In certain embodiments, the crystalline glycolate salt provided herein has an X-ray powder diffractogram substantially as shown in FIG. 7 (the middle diffractogram).

Figure 8:
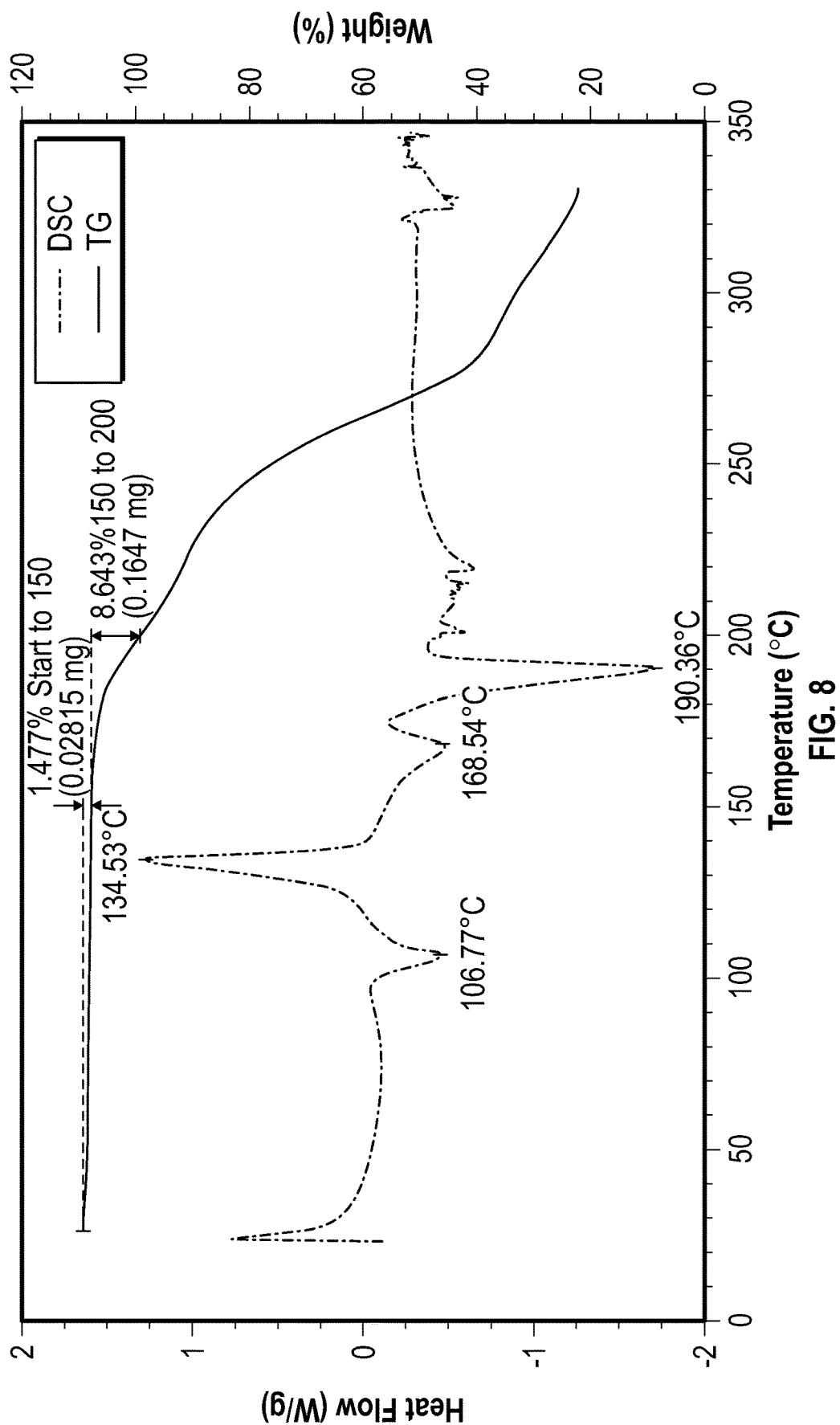
FIG. 8 depicts DSC/TGA thermograms of a crystalline glycolate salt of the Compound.

In certain embodiments, the crystalline glycolate salt provided herein has a DSC thermogram comprising an endothermic peak at about 107° C. In certain embodiments, the crystalline glycolate salt provided herein has a DSC thermogram comprising an endothermic peak at 107±3° C. In certain embodiments, the crystalline glycolate salt provided herein has a DSC thermogram comprising an endothermic peak at about 168° C. In certain embodiments, the crystalline glycolate salt provided herein has a DSC thermogram comprising an endothermic peak at 168±3° C. In certain embodiments, the crystalline glycolate salt provided herein has a DSC thermogram comprising an endothermic peak at about 190° C. In certain embodiments, the crystalline glycolate salt provided herein has a DSC thermogram comprising an endothermic peak at 190±3° C. In certain embodiments, the crystalline glycolate salt provided herein has a DSC thermogram comprising an exothermic peak at about 134° C. In certain embodiments, the crystalline glycolate salt provided herein has a DSC thermogram comprising an exothermic peak at 134±3° C. In certain embodiments, the crystalline glycolate salt provided herein has a DSC thermogram substantially as shown in FIG. 8. In certain embodiments, the crystalline glycolate salt provided herein has a melting point of about 190° C.

In certain embodiments, the crystalline glycolate salt provided herein has a TGA thermogram showing a weight loss of about 1.5% from room temperature to 150° C. In certain embodiments, the crystalline glycolate salt provided herein has a TGA thermogram showing a weight loss of about 9% from 150° C. to 200° C. In certain embodiments, the crystalline glycolate salt provided herein has a TGA thermogram substantially as shown in FIG. 8.

In certain embodiments, the crystalline glycolate salt provided herein is solvated. In certain embodiments, the crystalline glycolate salt provided herein is an acetone solvate. In certain embodiments, the crystalline glycolate salt provided herein is a hydrate.

In yet another embodiment, provided herein is a crystalline lactate salt of (1r,4r)-N$^1$-(5-chloro-4-(5-(cyclopropylmethyl)-1-methyl-1H-pyrazol-4-yl)pyrimidin-2-yl)cyclohexane-1,4-diamine or an isotopic variant thereof; or a pharmaceutically acceptable solvate thereof.

In certain embodiments, the molar ratio of the Compound versus lactic acid in the crystalline lactate salt provided herein is ranging from about 0.5 to about 3 or from about 0.5 to about 2.5. In certain embodiments, the molar ratio of the Compound versus lactic acid in the crystalline lactate salt provided herein is about 0.5, about 0.6, about 0.7, about 0.8, about 0.9, about 1, about 1.1, about 1.2, about 1.4, about 1.5, about 1.6, about 1.8, about 2, about 2.2, about 2.4, about 2.6, about 2.8, or about 3. In certain embodiments, the molar ratio of the Compound versus lactic acid in the crystalline lactate salt provided herein is about 1. In certain embodiments, the molar ratio of the Compound versus lactic acid in the crystalline lactate salt provided herein is about 2.

In one embodiment, the crystalline lactate salt provided herein comprises about one molar equivalent of the Compound and about one molar equivalent of lactic acid. In another embodiment, the crystalline lactate salt provided herein comprises about one molar equivalent of the Compound and about two molar equivalents of lactic acid. In certain embodiments, the molar ratio of the Compound versus lactic acid in the crystalline lactate salt provided herein is determined by $^1$H NMR spectroscopy. In certain embodiments, the molar ratio of the Compound versus lactic acid in the crystalline lactate salt provided herein is determined by an elemental analysis.

In certain embodiments, the crystalline lactate salt provided herein has an X-ray powder diffractogram substantially as shown in FIG. 7 (the bottom diffractogram).

Figure 9:
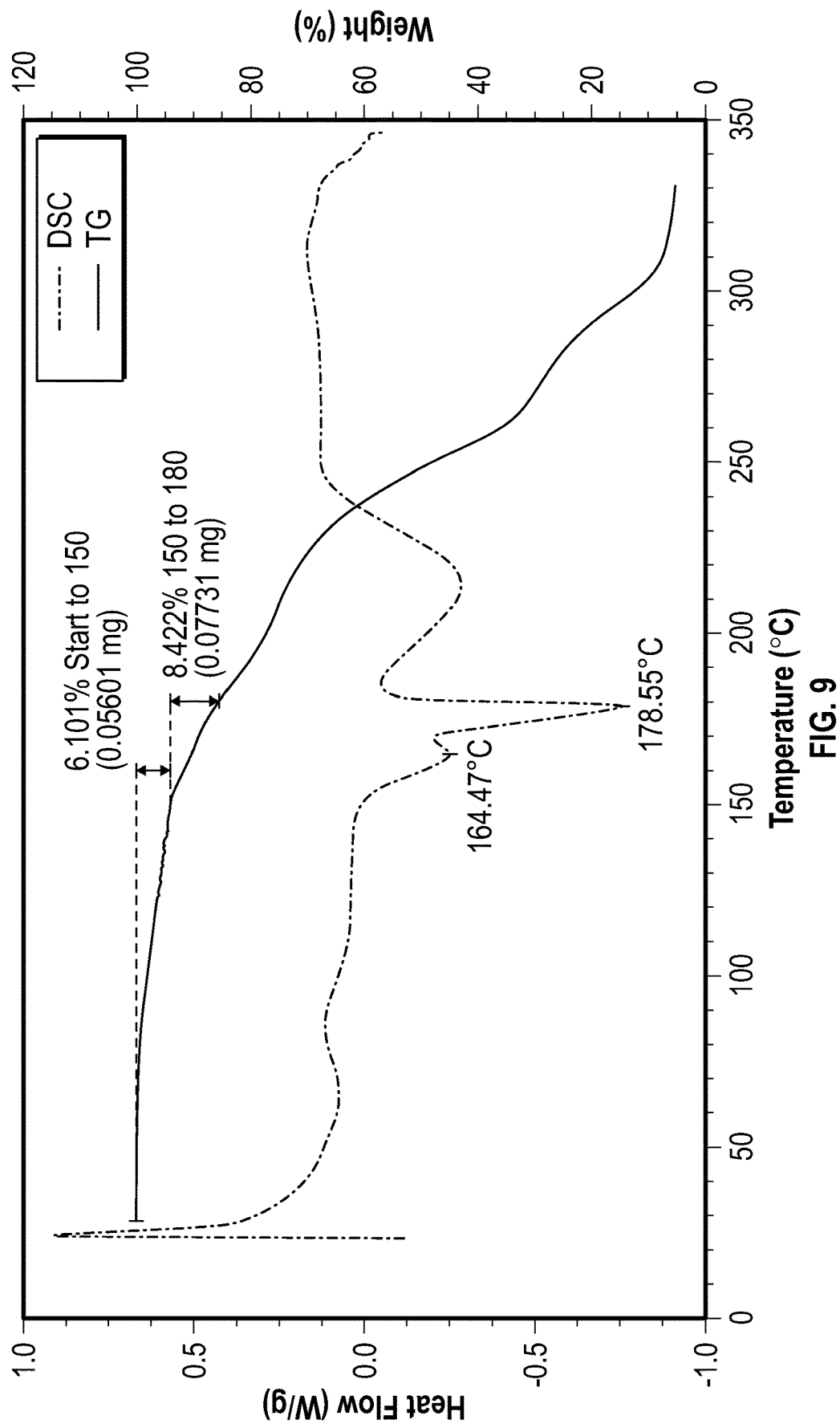
FIG. 9 depicts DSC/TGA thermograms of a crystalline lactate salt of the Compound.

In certain embodiments, the crystalline lactate salt provided herein has a DSC thermogram comprising an endothermic peak at about 165° C. In certain embodiments, the crystalline lactate salt provided herein has a DSC thermogram comprising an endothermic peak at 165±3° C. In certain embodiments, the crystalline lactate salt provided herein has a DSC thermogram comprising an endothermic peak at about 179° C. In certain embodiments, the crystalline lactate salt provided herein has a DSC thermogram comprising an endothermic peak at 179±3° C. In certain embodiments, the crystalline lactate salt provided herein has a DSC thermogram substantially as shown in FIG. 9. In certain embodiments, the crystalline lactate salt provided herein has a melting point of about 179° C.

In certain embodiments, the crystalline lactate salt provided herein has a TGA thermogram showing a weight loss of about 6% from room temperature to 150° C. In certain embodiments, the crystalline lactate salt provided herein has a TGA thermogram showing a weight loss of about 8.5% from 150° C. to 180° C. In certain embodiments, the crystalline lactate salt provided herein has a TGA thermogram substantially as shown in FIG. 9.

In certain embodiments, the crystalline lactate salt provided herein is solvated. In certain embodiments, the crystalline lactate salt provided herein is an ethanol solvate. In certain embodiments, the crystalline lactate salt provided herein is a hexane solvate. In certain embodiments, the crystalline lactate salt provided herein is a hydrate.

In yet another embodiment, provided herein is a crystalline hippurate salt of (1r,4r)-N$^1$-(5-chloro-4-(5-(cyclopropylmethyl)-1-methyl-1H-pyrazol-4-yl)pyrimidin-2-yl)cyclohexane-1,4-diamine or an isotopic variant thereof; or a pharmaceutically acceptable solvate thereof.

In certain embodiments, the molar ratio of the Compound versus hippuric acid in the crystalline hippurate salt provided herein is ranging from about 0.5 to about 3 or from about 0.5 to about 2.5. In certain embodiments, the molar ratio of the Compound versus hippuric acid in the crystalline hippurate salt provided herein is about 0.5, about 0.6, about 0.7, about 0.8, about 0.9, about 1, about 1.1, about 1.2, about 1.4, about 1.5, about 1.6, about 1.8, about 2, about 2.2, about 2.4, about 2.6, about 2.8, or about 3. In certain embodiments, the molar ratio of the Compound versus hippuric acid in the crystalline hippurate salt provided herein is about 1. In certain embodiments, the molar ratio of the Compound versus hippuric acid in the crystalline hippurate salt provided herein is about 2.

In one embodiment, the crystalline hippurate salt provided herein comprises about one molar equivalent of the Compound and about one molar equivalent of hippuric acid. In another embodiment, the crystalline hippurate salt provided herein comprises about one molar equivalent of the Compound and about two molar equivalents of hippuric acid. In certain embodiments, the molar ratio of the Compound versus hippuric acid in the crystalline hippurate salt provided herein is determined by $^1$H NMR spectroscopy. In certain embodiments, the molar ratio of the Compound versus hippuric acid in the crystalline hippurate salt provided herein is determined by an elemental analysis.

Figure 10:
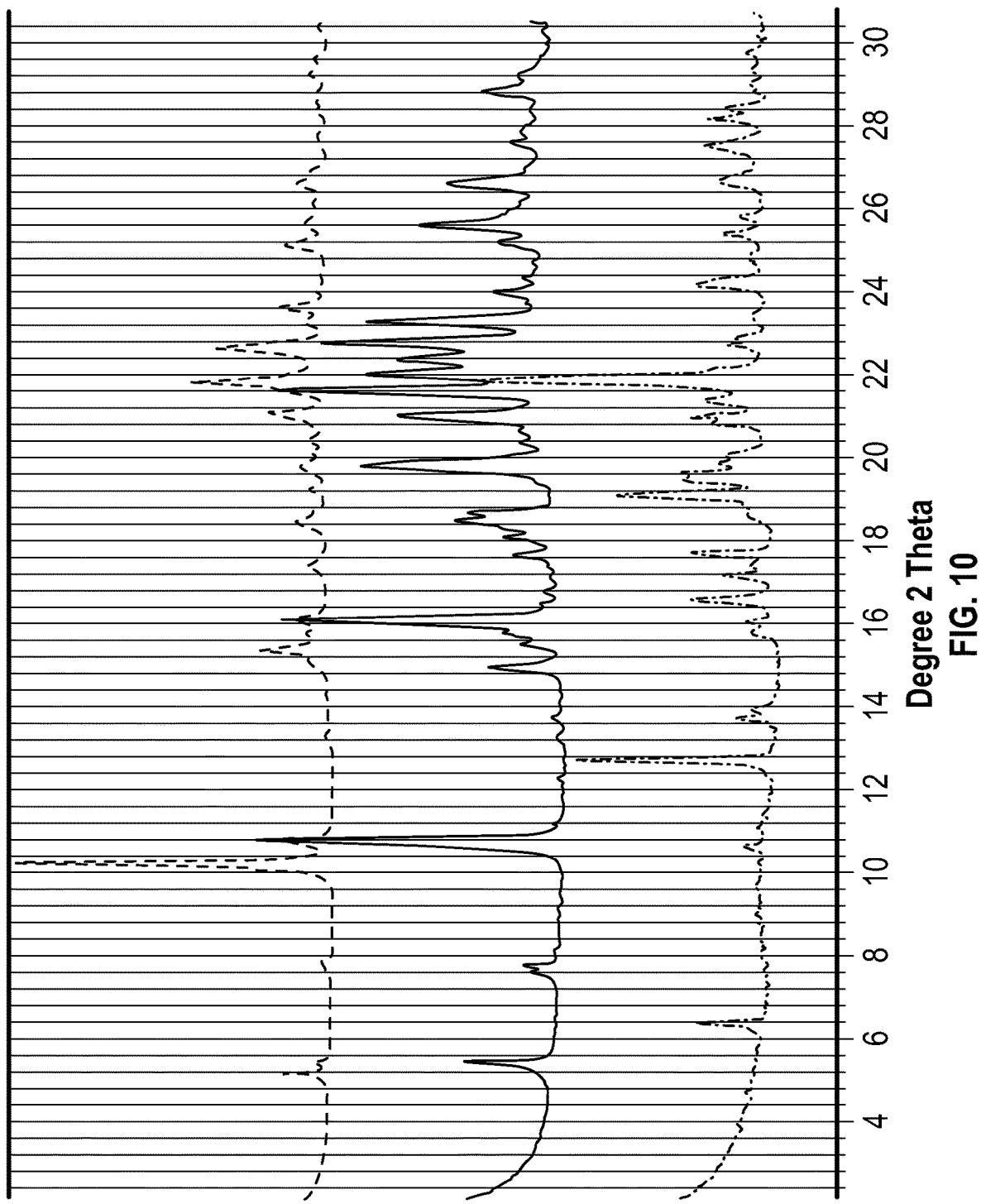
FIG. 10 depicts X-ray powder diffractograms of two crystalline hippurate salts (the top and middle diffractograms) and one crystalline maleate salt (the bottom diffractogram) of the Compound.

In certain embodiments, the crystalline hippurate salt provided herein has an X-ray powder diffractogram substantially as shown in FIG. 10 (the top diffractogram). In certain embodiments, the crystalline hippurate salt provided herein has an X-ray powder diffractogram substantially as shown in FIG. 10 (the middle diffractogram).

Figure 11:
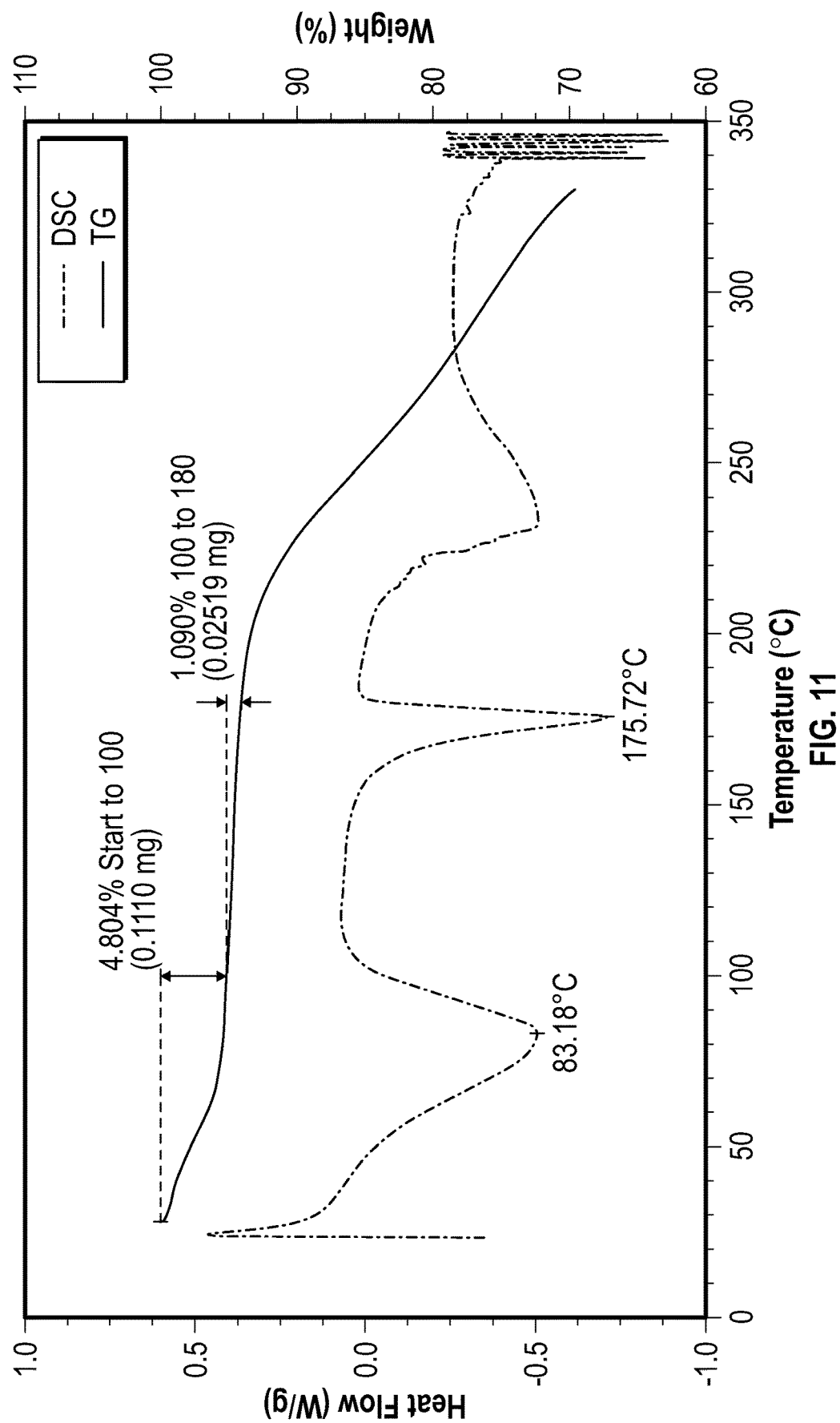
FIG. 11 depicts DSC/TGA thermograms of a crystalline hippurate salt of the Compound.

In certain embodiments, the crystalline hippurate salt provided herein has a DSC thermogram comprising an endothermic peak at about 83° C. In certain embodiments, the crystalline hippurate salt provided herein has a DSC thermogram comprising an endothermic peak at 83±3° C. In certain embodiments, the crystalline hippurate salt provided herein has a DSC thermogram comprising an endothermic peak at about 176° C. In certain embodiments, the crystalline hippurate salt provided herein has a DSC thermogram comprising an endothermic peak at 176±3° C. In certain embodiments, the crystalline hippurate salt provided herein has a DSC thermogram substantially as shown in FIG. 11. In certain embodiments, the crystalline hippurate salt provided herein has a melting point of about 176° C.

In certain embodiments, the crystalline hippurate salt provided herein has a TGA thermogram showing a weight loss of about 5% from room temperature to 100° C. In certain embodiments, the crystalline hippurate salt provided herein has a TGA thermogram showing a weight loss of about 1% from 100° C. to 180° C. In certain embodiments, the crystalline hippurate salt provided herein has a TGA thermogram substantially as shown in FIG. 11.

In certain embodiments, the crystalline hippurate salt provided herein is solvated. In certain embodiments, the crystalline hippurate salt provided herein is an ethanol solvate. In certain embodiments, the crystalline hippurate salt provided herein is a hexane solvate. In certain embodiments, the crystalline hippurate salt provided herein is a hydrate.

In yet another embodiment, provided herein is a crystalline maleate salt of (1r,4r)-N$^1$-(5-chloro-4-(5-(cyclopropylmethyl)-1-methyl-1H-pyrazol-4-yl)pyrimidin-2-yl)cyclohexane-1,4-diamine or an isotopic variant thereof; or a pharmaceutically acceptable solvate thereof.

In certain embodiments, the molar ratio of the Compound versus maleic acid in the crystalline maleate salt provided herein is ranging from about 0.25 to about 1.5 or from about 0.5 to about 1. In certain embodiments, the molar ratio of the Compound versus maleic acid in the crystalline maleate salt provided herein is about 0.25, about 0.3, about 0.4, about 0.5, about 0.6, about 0.7, about 0.8, about 0.9, about 1, about 1.1, about 1.2, about 1.3, about 1.4, or about 1.5. In certain embodiments, the molar ratio of the Compound versus maleic acid in the crystalline maleate salt provided herein is about 0.5. In certain embodiments, the molar ratio of the Compound versus maleic acid in the crystalline maleate salt provided herein is about 1.

In one embodiment, the crystalline maleate salt provided herein comprises about two molar equivalents of the Compound and about one molar equivalent of maleic acid. In another embodiment, the crystalline maleate salt provided herein comprises about one molar equivalent of the Compound and about one molar equivalent of maleic acid. In certain embodiments, the molar ratio of the Compound versus maleic acid in the crystalline maleate salt provided herein is determined by $^1$H NMR spectroscopy. In certain embodiments, the molar ratio of the Compound versus maleic acid in the crystalline maleate salt provided herein is determined by an elemental analysis.

In certain embodiments, the crystalline maleate salt provided herein has an X-ray powder diffractogram substantially as shown in FIG. 10 (the bottom diffractogram).

Figure 12:
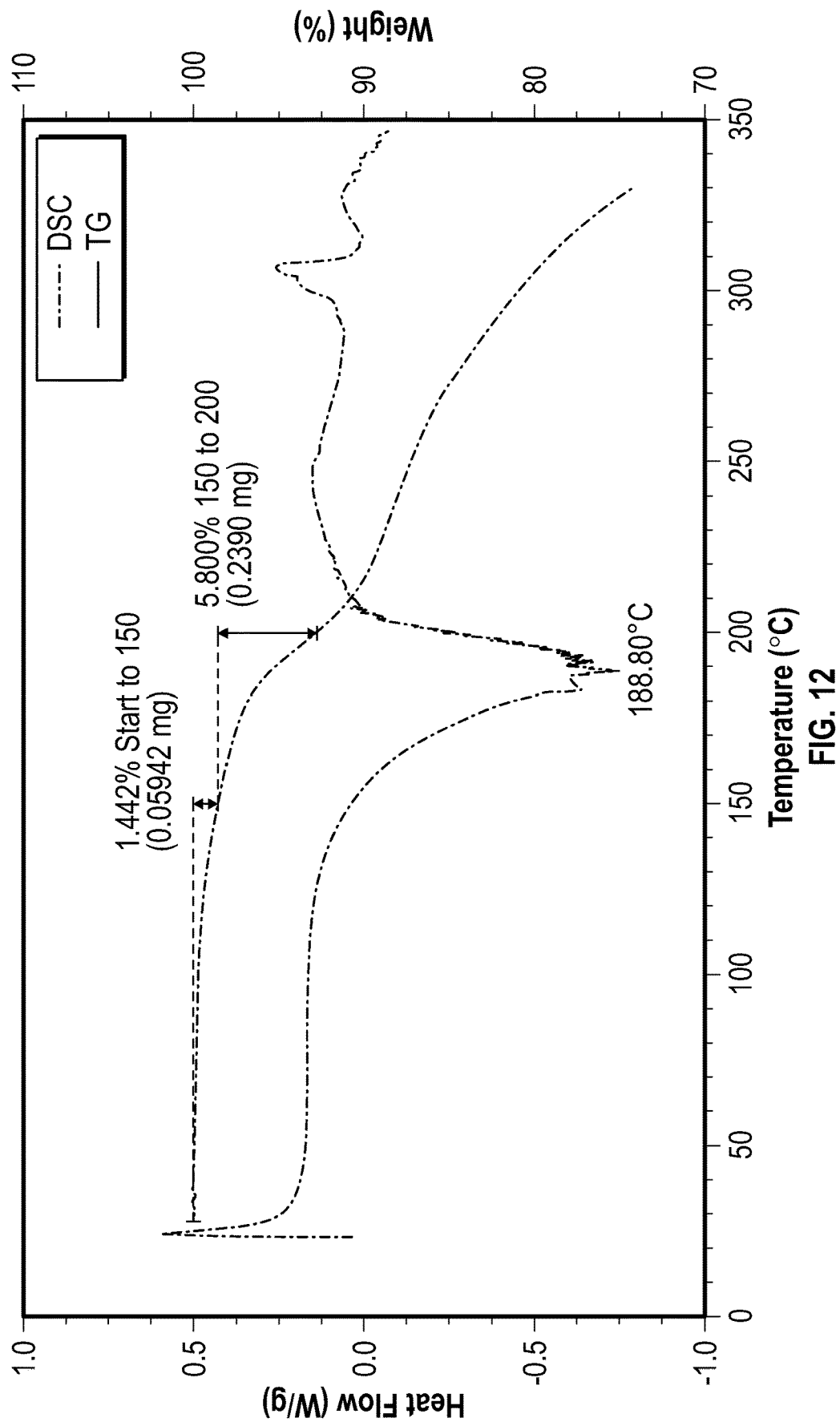
FIG. 12 depicts DSC/TGA thermograms of a crystalline maleate salt of the Compound.

In certain embodiments, the crystalline maleate salt provided herein has a DSC thermogram comprising an endothermic peak at about 189° C. In certain embodiments, the crystalline maleate salt provided herein has a DSC thermogram comprising an endothermic peak at 189±3° C. In certain embodiments, the crystalline maleate salt provided herein has a DSC thermogram substantially as shown in FIG. 12.

In certain embodiments, the crystalline maleate salt provided herein has a TGA thermogram showing a weight loss of about 1.5% from room temperature to 150° C. In certain embodiments, the crystalline maleate salt provided herein has a TGA thermogram showing a weight loss of about 6% from 150° C. to 200° C. In certain embodiments, the crystalline maleate salt provided herein has a TGA thermogram substantially as shown in FIG. 12.

In certain embodiments, the crystalline maleate salt provided herein is solvated. In certain embodiments, the crystalline maleate salt provided herein is an ethanol solvate. In certain embodiments, the crystalline maleate salt provided herein is a hexane solvate. In certain embodiments, the crystalline maleate salt provided herein is a hydrate.

In yet another embodiment, provided herein is a crystalline malate salt of (1r,4r)-N$^1$-(5-chloro-4-(5-(cyclopropylmethyl)-1-methyl-1H-pyrazol-4-yl)pyrimidin-2-yl)cyclohexane-1,4-diamine or an isotopic variant thereof; or a pharmaceutically acceptable solvate thereof.

In certain embodiments, the molar ratio of the Compound versus malic acid in the crystalline malate salt provided herein is ranging from about 0.25 to about 1.5 or from about 0.5 to about 1. In certain embodiments, the molar ratio of the Compound versus malic acid in the crystalline malate salt provided herein is about 0.25, about 0.3, about 0.4, about 0.5, about 0.6, about 0.7, about 0.8, about 0.9, about 1, about 1.1, about 1.2, about 1.3, about 1.4, or about 1.5. In certain embodiments, the molar ratio of the Compound versus malic acid in the crystalline malate salt provided herein is about 0.5. In certain embodiments, the molar ratio of the Compound versus malic acid in the crystalline malate salt provided herein is about 1.

In one embodiment, the crystalline malate salt provided herein comprises about two molar equivalents of the Compound and about one molar equivalent of malic acid. In another embodiment, the crystalline malate salt provided herein comprises about one molar equivalent of the Compound and about one molar equivalent of malic acid. In certain embodiments, the molar ratio of the Compound versus malic acid in the crystalline malate salt provided herein is determined by $^1$H NMR spectroscopy. In certain embodiments, the molar ratio of the Compound versus malic acid in the crystalline malate salt provided herein is determined by an elemental analysis.

Figure 13:
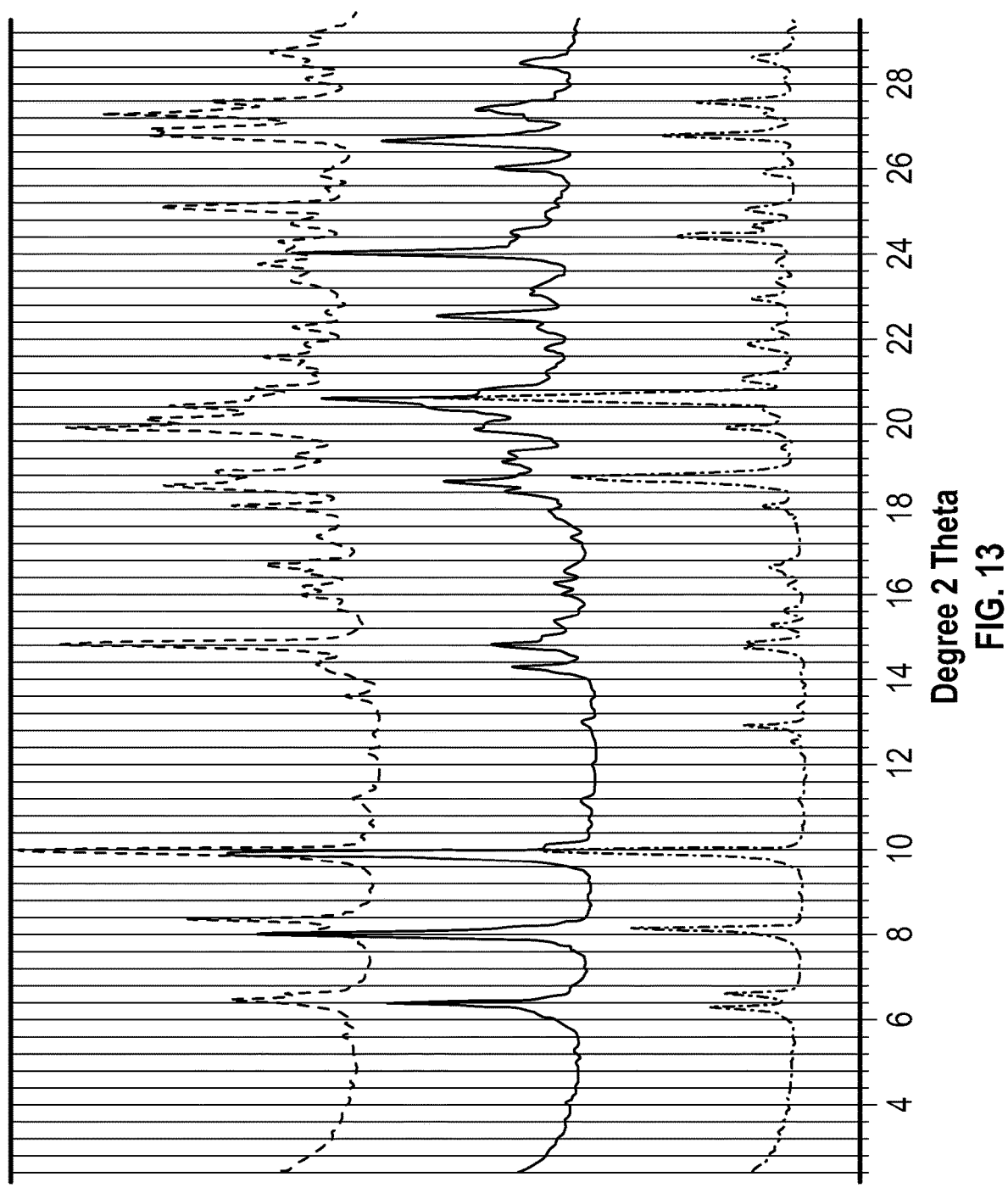
FIG. 13 depicts X-ray powder diffractograms of three crystalline malate salts of the Compound.

In certain embodiments, the crystalline malate salt provided herein has an X-ray powder diffractogram substantially as shown in FIG. 13 (the top diffractogram). In certain embodiments, the crystalline malate salt provided herein has an X-ray powder diffractogram substantially as shown in FIG. 13 (the middle diffractogram). In certain embodiments, the crystalline malate salt provided herein has an X-ray powder diffractogram substantially as shown in FIG. 13 (the bottom diffractogram).

Figure 14:
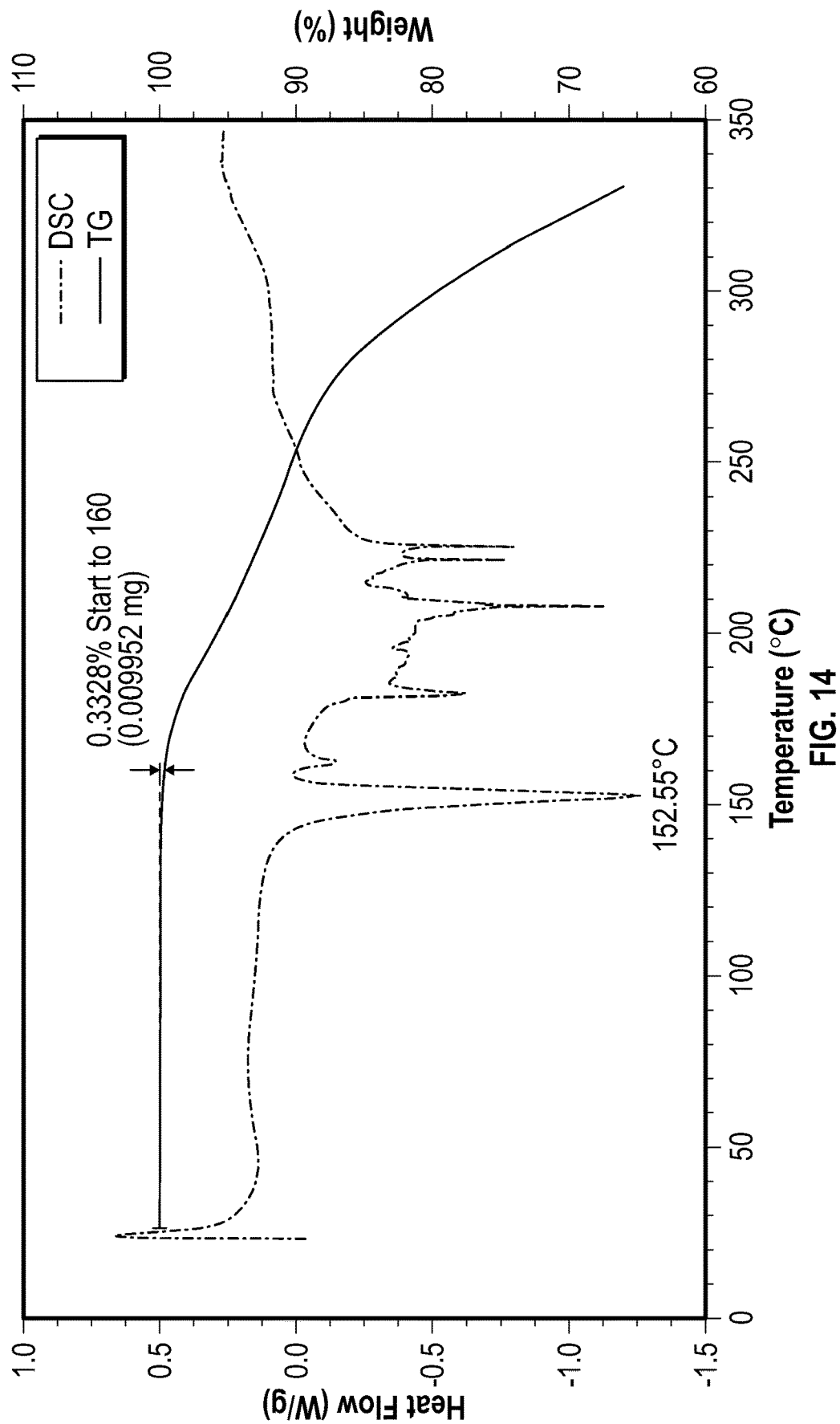
FIG. 14 depicts DSC/TGA thermograms of a crystalline malate salt of the Compound.

In certain embodiments, the crystalline malate salt provided herein has a DSC thermogram comprising an endothermic peak at about 153° C. In certain embodiments, the crystalline malate salt provided herein has a DSC thermogram comprising an endothermic peak at 153±3° C. In certain embodiments, the crystalline malate salt provided herein has a DSC thermogram substantially as shown in FIG. 14. In certain embodiments, the crystalline malate salt provided herein has a melting point of about 153° C.

In certain embodiments, the crystalline malate salt provided herein has a TGA thermogram showing a weight loss of about 0.3% from room temperature to 160° C. In certain embodiments, the crystalline malate salt provided herein has a TGA thermogram substantially as shown in FIG. 14.

In certain embodiments, the crystalline malate salt provided herein is unsolvated.

In yet another embodiment, provided herein is a crystalline mesylate salt of (1r,4r)-N$^1$-(5-chloro-4-(5-(cyclopropylmethyl)-1-methyl-1H-pyrazol-4-yl)pyrimidin-2-yl)cyclohexane-1,4-diamine or an isotopic variant thereof; or a pharmaceutically acceptable solvate thereof. As used herein, the term "methanesulfonate" is used interchangeably with the term "mesylate."

In certain embodiments, the molar ratio of the Compound versus methanesulfonic acid in the crystalline mesylate salt provided herein is ranging from about 0.5 to about 3 or from about 0.5 to about 2.5. In certain embodiments, the molar ratio of the Compound versus methanesulfonic acid in the crystalline mesylate salt provided herein is about 0.5, about 0.6, about 0.7, about 0.8, about 0.9, about 1, about 1.1, about 1.2, about 1.4, about 1.5, about 1.6, about 1.8, about 2, about 2.2, about 2.4, about 2.6, about 2.8, or about 3. In certain embodiments, the molar ratio of the Compound versus methanesulfonic acid in the crystalline mesylate salt provided herein is about 1. In certain embodiments, the molar ratio of the Compound versus methanesulfonic acid in the crystalline mesylate salt provided herein is about 2.

In one embodiment, the crystalline mesylate salt provided herein comprises about one molar equivalent of the Compound and about one molar equivalent of methanesulfonic acid. In another embodiment, the crystalline mesylate salt provided herein comprises about one molar equivalent of the Compound and about two molar equivalents of methanesulfonic acid. In certain embodiments, the molar ratio of the Compound versus methanesulfonic acid in the crystalline mesylate salt provided herein is determined by $^1$H NMR spectroscopy. In certain embodiments, the molar ratio of the Compound versus methanesulfonic acid in the crystalline mesylate salt provided herein is determined by an elemental analysis.

Figure 15:
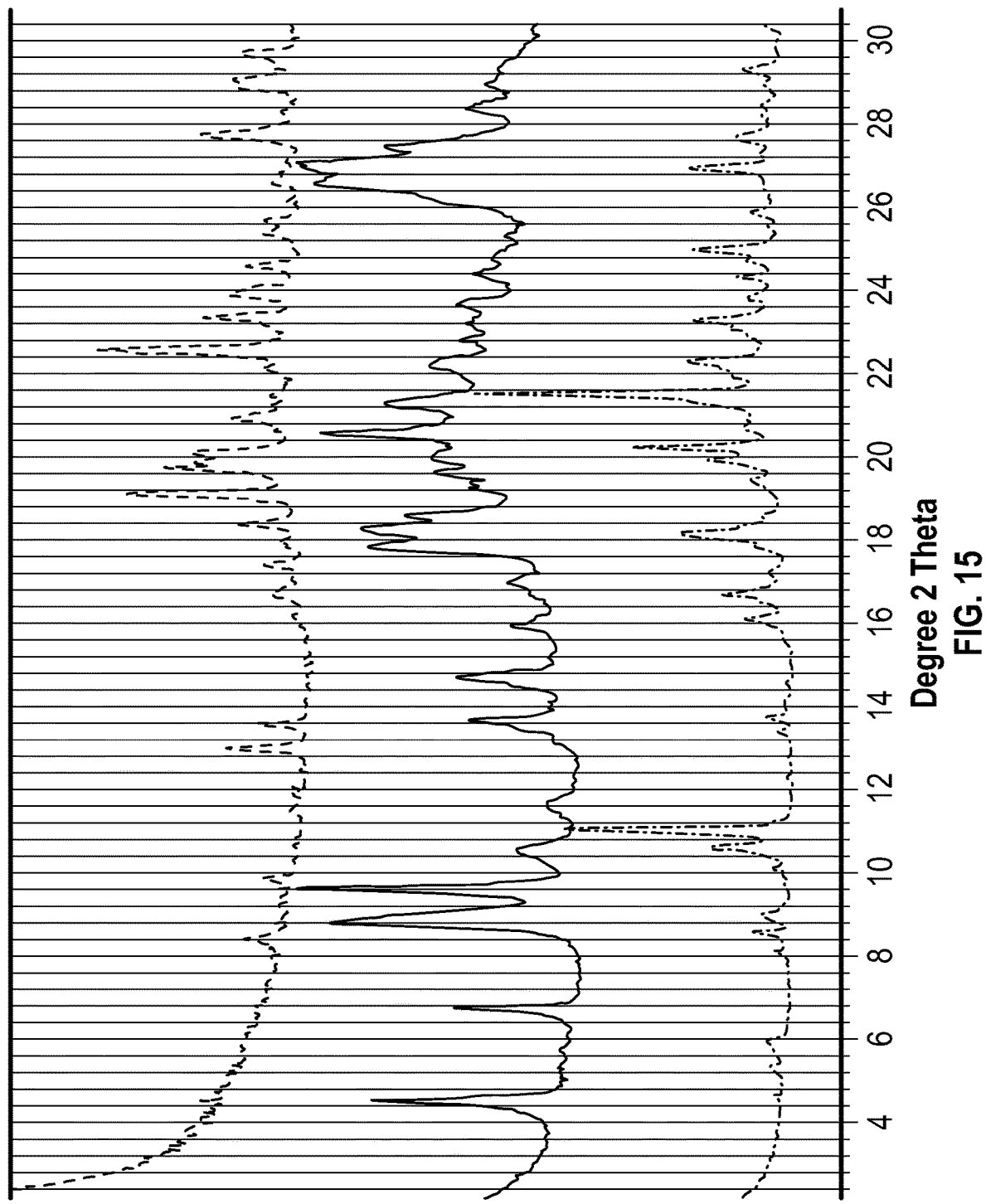
FIG. 15 depicts X-ray powder diffractograms of one crystalline mesylate salt (the top diffractogram) and two crystalline succinate salts (the middle and bottom diffractograms) of the Compound.

In certain embodiments, the crystalline mesylate salt provided herein has an X-ray powder diffractogram substantially as shown in FIG. 15 (the top diffractogram).

Figure 16:
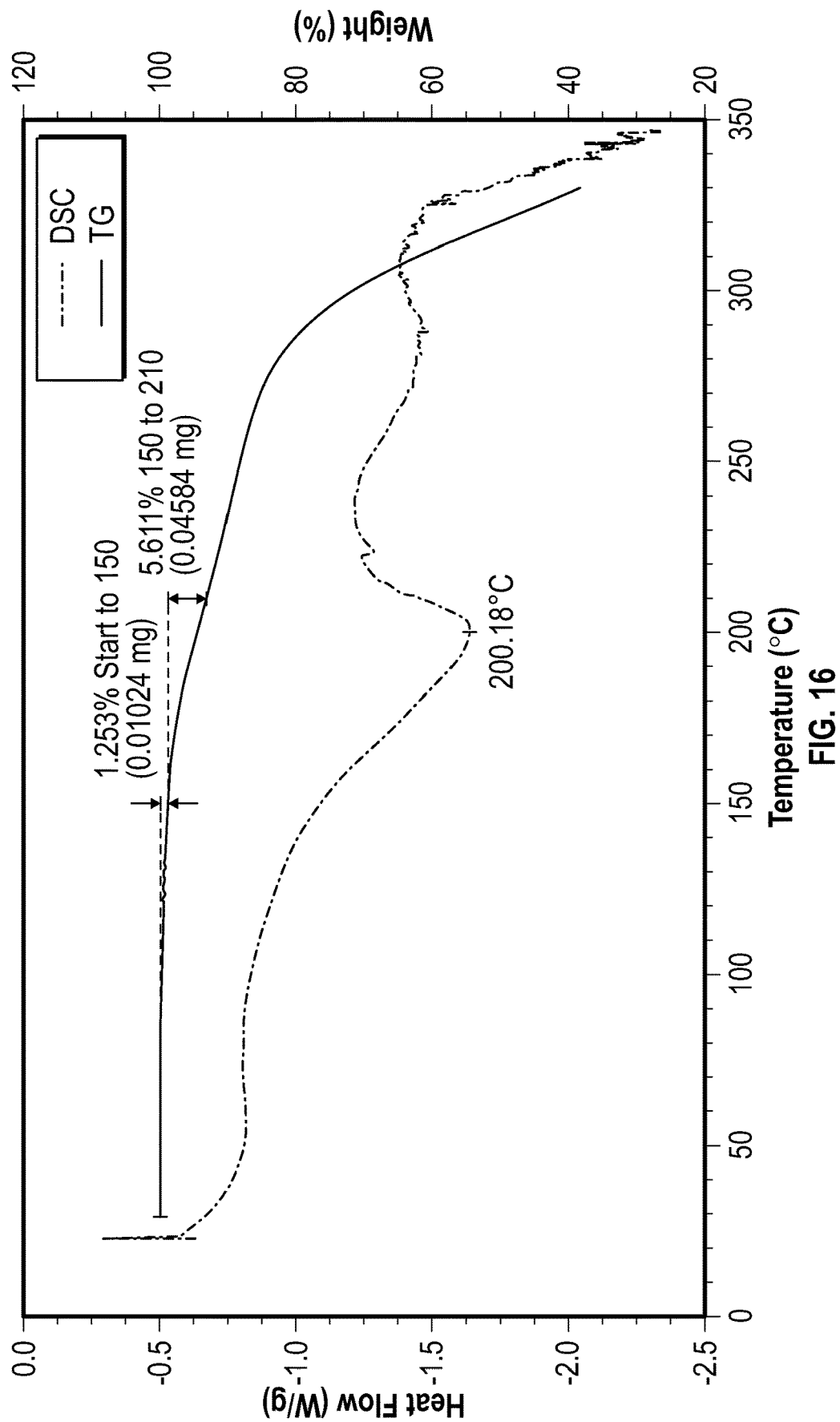
FIG. 16 depicts DSC/TGA thermograms of a crystalline mesylate salt of the Compound.

In certain embodiments, the crystalline mesylate salt provided herein has a DSC thermogram comprising an endothermic peak at about 200° C. In certain embodiments, the crystalline mesylate salt provided herein has a DSC thermogram comprising an endothermic peak at 200±3° C. In certain embodiments, the crystalline mesylate salt provided herein has a DSC thermogram substantially as shown in FIG. 16.

In certain embodiments, the crystalline mesylate salt provided herein has a TGA thermogram showing a weight loss of about 1.2% from room temperature to 150° C. In certain embodiments, the crystalline mesylate salt provided herein has a TGA thermogram showing a weight loss of about 5.5% from 150° C. to 210° C. In certain embodiments, the crystalline mesylate salt provided herein has a TGA thermogram substantially as shown in FIG. 16.

In certain embodiments, the crystalline mesylate salt provided herein is unsolvated.

In yet another embodiment, provided herein is a crystalline succinate salt of (1r,4r)-N$^1$-(5-chloro-4-(5-(cyclopropylmethyl)-1-methyl-1H-pyrazol-4-yl)pyrimidin-2-yl)cyclohexane-1,4-diamine or an isotopic variant thereof; or a pharmaceutically acceptable solvate thereof.

In certain embodiments, the molar ratio of the Compound versus succinic acid in the crystalline succinate salt provided herein is ranging from about 0.25 to about 1.5 or from about 0.5 to about 1. In certain embodiments, the molar ratio of the Compound versus succinic acid in the crystalline succinate salt provided herein is about 0.25, about 0.3, about 0.4, about 0.5, about 0.6, about 0.7, about 0.8, about 0.9, about 1, about 1.1, about 1.2, about 1.3, about 1.4, or about 1.5. In certain embodiments, the molar ratio of the Compound versus succinic acid in the crystalline succinate salt provided herein is about 0.5. In certain embodiments, the molar ratio of the Compound versus succinic acid in the crystalline succinate salt provided herein is about 1.

In one embodiment, the crystalline succinate salt provided herein comprises about two molar equivalents of the Compound and about one molar equivalent of succinic acid. In another embodiment, the crystalline succinate salt provided herein comprises about one molar equivalent of the Compound and about one molar equivalent of succinic acid. In certain embodiments, the molar ratio of the Compound versus succinic acid in the crystalline succinate salt provided herein is determined by $^1$H NMR spectroscopy. In certain embodiments, the molar ratio of the Compound versus succinic acid in the crystalline succinate salt provided herein is determined by an elemental analysis.

In certain embodiments, the crystalline succinate salt provided herein has an X-ray powder diffractogram substantially as shown in FIG. 15 (the middle diffractogram). In certain embodiments, the crystalline succinate salt provided herein has an X-ray powder diffractogram substantially as shown in FIG. 15 (the bottom diffractogram).

Figure 17:
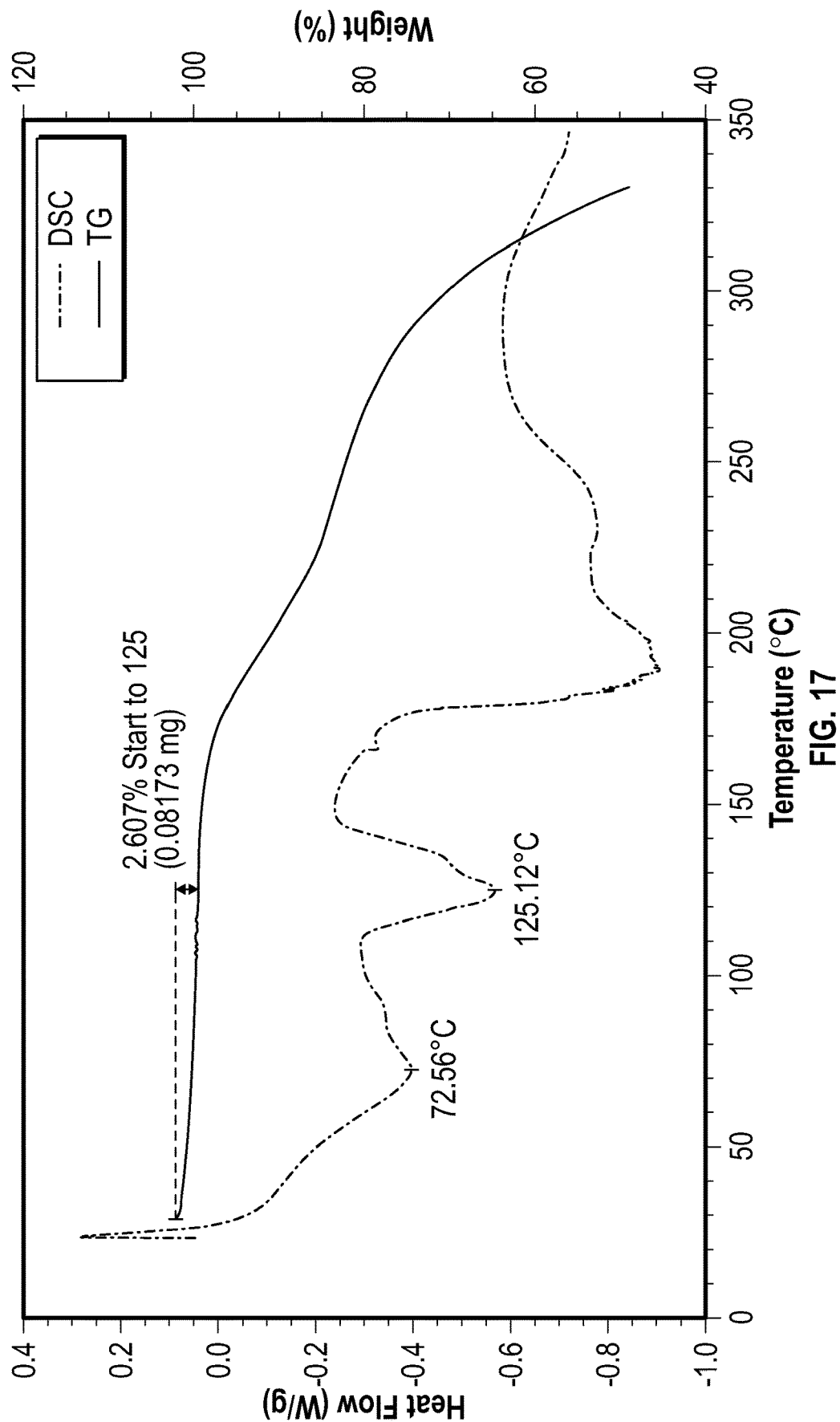
FIG. 17 depicts DSC/TGA thermograms of a crystalline succinate salt of the Compound.

In certain embodiments, the crystalline succinate salt provided herein has a DSC thermogram comprising an endothermic peak at about 73° C. In certain embodiments, the crystalline succinate salt provided herein has a DSC thermogram comprising an endothermic peak at 73±3° C. In certain embodiments, the crystalline succinate salt provided herein has a DSC thermogram comprising an endothermic peak at about 125° C. In certain embodiments, the crystalline succinate salt provided herein has a DSC thermogram comprising an endothermic peak at 125±3° C. In certain embodiments, the crystalline succinate salt provided herein has a DSC thermogram substantially as shown in FIG. 17.

In certain embodiments, the crystalline succinate salt provided herein has a TGA thermogram showing a weight loss of about 2.5% from room temperature to 125° C. In certain embodiments, the crystalline succinate salt provided herein has a TGA thermogram substantially as shown in FIG. 17.

In certain embodiments, the crystalline succinate salt provided herein is solvated. In certain embodiments, the crystalline succinate salt provided herein is an acetone solvate. In certain embodiments, the crystalline succinate salt provided herein is a hydrate.

In yet another embodiment, provided herein is a crystalline sulfate salt of (1r,4r)-N$^1$-(5-chloro-4-(5-(cyclopropylmethyl)-1-methyl-1H-pyrazol-4-yl)pyrimidin-2-yl)cyclohexane-1,4-diamine or an isotopic variant thereof; or a pharmaceutically acceptable solvate thereof.

In certain embodiments, the molar ratio of the Compound versus sulfuric acid in the crystalline sulfate salt provided herein is ranging from 0.25 to about 1.5 or from about 0.5 to about 1. In certain embodiments, the molar ratio of the Compound versus sulfuric acid in the crystalline sulfate salt provided herein is about 0.25, about 0.3, about 0.4, about 0.5, about 0.6, about 0.7, about 0.8, about 0.9, about 1, about 1.1, about 1.2, about 1.3, about 1.4, or about 1.5. In certain embodiments, the molar ratio of the Compound versus sulfuric acid in the crystalline sulfate salt provided herein is about 0.5. In certain embodiments, the molar ratio of the Compound versus sulfuric acid in the crystalline sulfate salt provided herein is about 1.

In one embodiment, the crystalline sulfate salt provided herein comprises about two molar equivalents of the Compound and about one molar equivalent of sulfuric acid. In another embodiment, the crystalline sulfate salt provided herein comprises about one molar equivalent of the Compound and about one molar equivalent of sulfuric acid. In certain embodiments, the molar ratio of the Compound versus sulfuric acid in the crystalline sulfate salt provided herein is determined by an elemental analysis.

Figure 18:
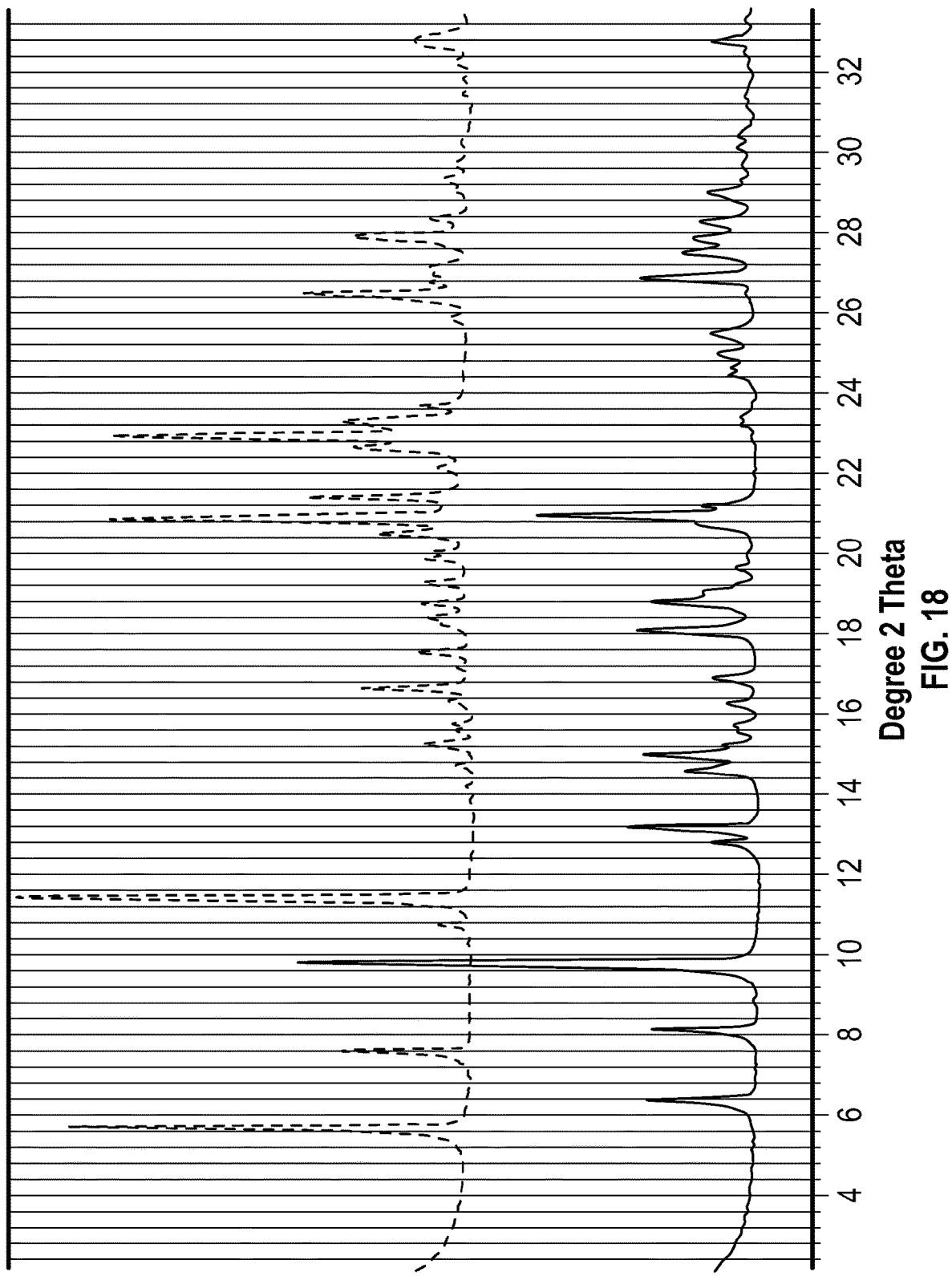
FIG. 18 depicts X-ray powder diffractograms of one crystalline sulfate salt (the top diffractogram) and one crystalline tartrate salt (the bottom diffractograms) of the Compound.

In certain embodiments, the crystalline sulfate salt provided herein has an X-ray powder diffractogram substantially as shown in FIG. 18 (the top diffractogram).

Figure 19:
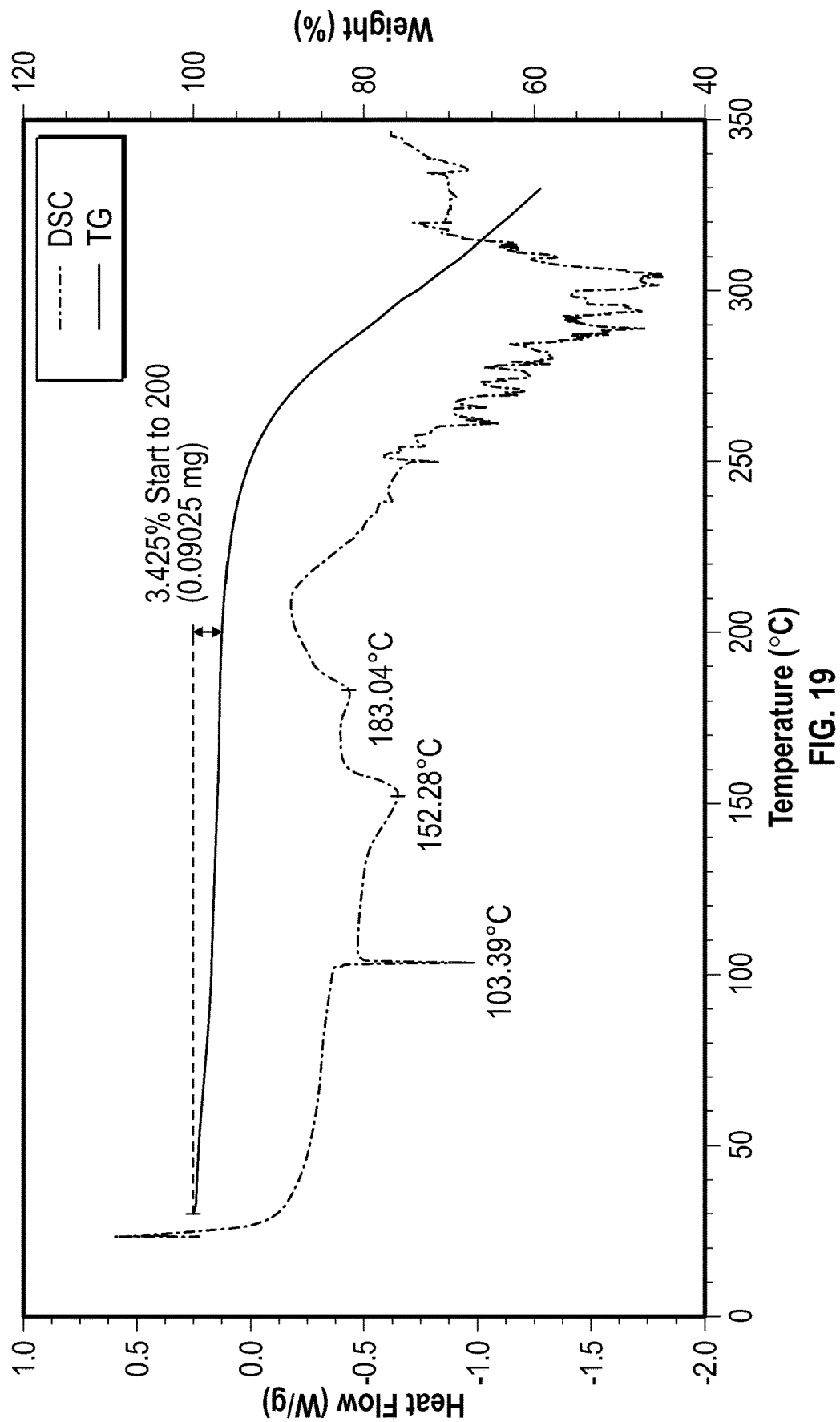
FIG. 19 depicts DSC/TGA thermograms of a crystalline sulfate salt of the Compound.

In certain embodiments, the crystalline sulfate salt provided herein has a DSC thermogram comprising an endothermic peak at about 103° C. In certain embodiments, the crystalline sulfate salt provided herein has a DSC thermogram comprising an endothermic peak at 103±3° C. In certain embodiments, the crystalline sulfate salt provided herein has a DSC thermogram comprising an endothermic peak at about 152° C. In certain embodiments, the crystalline sulfate salt provided herein has a DSC thermogram comprising an endothermic peak at 152±3° C. In certain embodiments, the crystalline sulfate salt provided herein has a DSC thermogram comprising an endothermic peak at about 183° C. In certain embodiments, the crystalline sulfate salt provided herein has a DSC thermogram comprising an endothermic peak at 183±3° C. In certain embodiments, the crystalline sulfate salt provided herein has a DSC thermogram substantially as shown in FIG. 19.

In certain embodiments, the crystalline sulfate salt provided herein has a TGA thermogram showing a weight loss of about 3.5% from room temperature to 200° C. In certain embodiments, the crystalline sulfate salt provided herein has a TGA thermogram substantially as shown in FIG. 19.

In certain embodiments, the crystalline sulfate salt provided herein is solvated. In certain embodiments, the crystalline sulfate salt provided herein is an acetone solvate. In certain embodiments, the crystalline sulfate salt provided herein is a hydrate.

In yet another embodiment, provided herein is a crystalline tartrate salt of (1r,4r)-N$^1$-(5-chloro-4-(5-(cyclopropylmethyl)-1-methyl-1H-pyrazol-4-yl)pyrimidin-2-yl)cyclohexane-1,4-diamine or an isotopic variant thereof; or a pharmaceutically acceptable solvate thereof.

In certain embodiments, the molar ratio of the Compound versus tartaric acid in the crystalline tartrate salt provided herein is ranging from about 0.25 to about 1.5 or from about 0.5 to about 1. In certain embodiments, the molar ratio of the Compound versus tartaric acid in the crystalline tartrate salt provided herein is about 0.25, about 0.3, about 0.4, about 0.5, about 0.6, about 0.7, about 0.8, about 0.9, about 1, about 1.1, about 1.2, about 1.3, about 1.4, or about 1.5. In certain embodiments, the molar ratio of the Compound versus tartaric acid in the crystalline tartrate salt provided herein is about 0.5. In certain embodiments, the molar ratio of the Compound versus tartaric acid in the crystalline tartrate salt provided herein is about 1.

In one embodiment, the crystalline tartrate salt provided herein comprises about two molar equivalents of the Compound and about one molar equivalent of tartaric acid. In another embodiment, the crystalline tartrate salt provided herein comprises about one molar equivalent of the Compound and about one molar equivalent of tartaric acid. In certain embodiments, the molar ratio of the Compound versus tartaric acid in the crystalline tartrate salt provided herein is determined by $^1$H NMR spectroscopy. In certain embodiments, the molar ratio of the Compound versus tartaric acid in the crystalline tartrate salt provided herein is determined by an elemental analysis.

In certain embodiments, the crystalline tartrate salt provided herein has an X-ray powder diffractogram substantially as shown in FIG. 18 (the bottom diffractogram).

Figure 20:
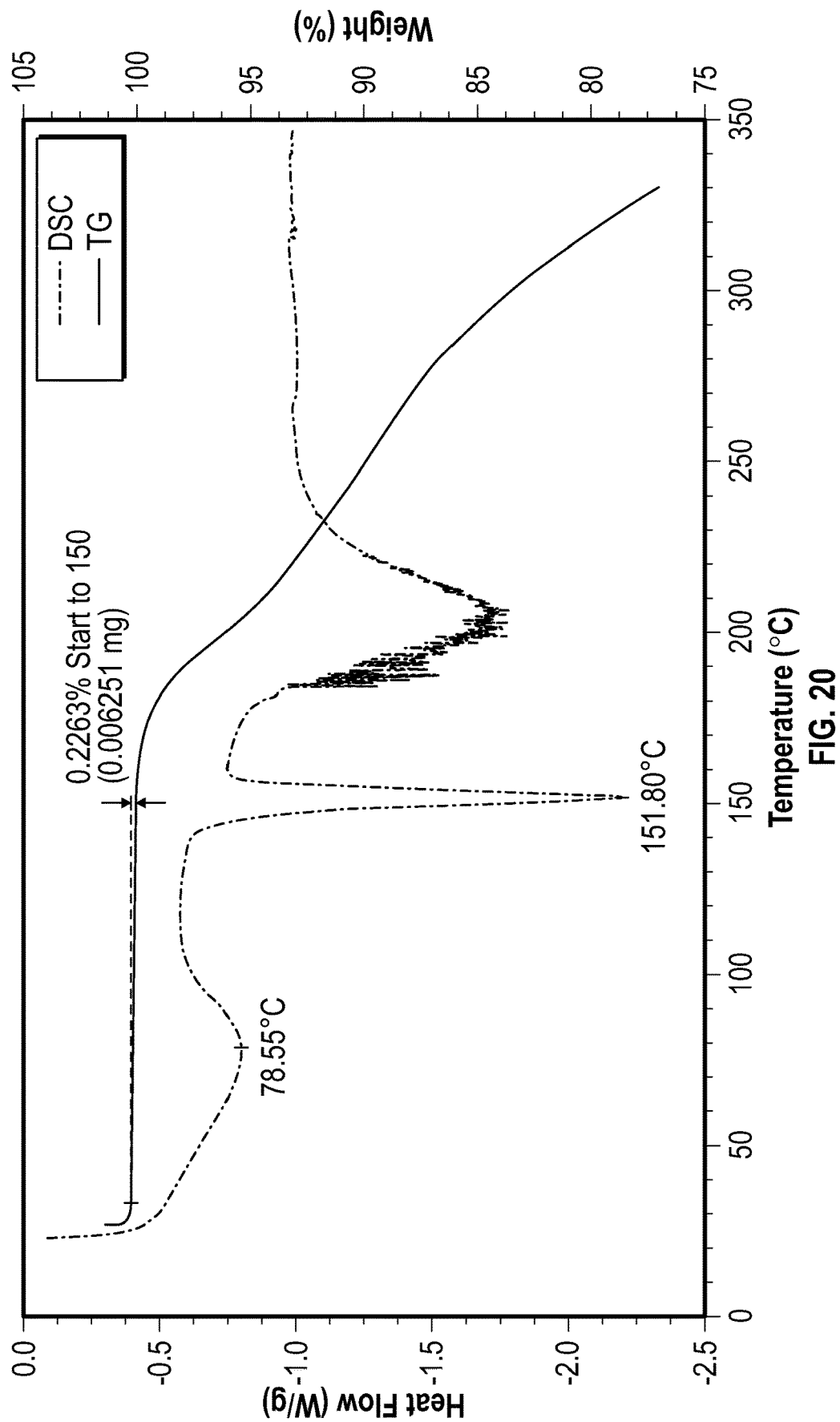
FIG. 20 depicts DSC/TGA thermograms of a crystalline tartrate salt of the Compound.

In certain embodiments, the crystalline tartrate salt provided herein has a DSC thermogram comprising an endothermic peak at about 79° C. In certain embodiments, the crystalline tartrate salt provided herein has a DSC thermogram comprising an endothermic peak at 79±3° C. In certain embodiments, the crystalline tartrate salt provided herein has a DSC thermogram comprising an endothermic peak at about 152° C. In certain embodiments, the crystalline tartrate salt provided herein has a DSC thermogram comprising an endothermic peak at 152±3° C. In certain embodiments, the crystalline tartrate salt provided herein has a DSC thermogram substantially as shown in FIG. 20. In certain embodiments, the crystalline tartrate salt provided herein has a melting point of about 152° C.

In certain embodiments, the crystalline tartrate salt provided herein has a TGA thermogram showing a weight loss of about 0.2% from room temperature to 150° C. In certain embodiments, the crystalline tartrate salt provided herein has a TGA thermogram substantially as shown in FIG. 20.

In certain embodiments, the crystalline tartrate salt provided herein is solvated. In certain embodiments, the crystalline tartrate salt provided herein is an acetone solvate. In certain embodiments, the crystalline tartrate salt provided herein is a hydrate.

In yet another embodiment, provided herein is a crystalline thiocyanate salt of (1r,4r)-N$^1$-(5-chloro-4-(5-(cyclopropylmethyl)-1-methyl-1H-pyrazol-4-yl)pyrimidin-2-yl)cyclohexane-1,4-diamine or an isotopic variant thereof; or a pharmaceutically acceptable solvate thereof.

In certain embodiments, the molar ratio of the Compound versus thiocyanic acid in the crystalline thiocyanate salt provided herein is ranging from about 0.5 to about 3 or from about 0.5 to about 2.5. In certain embodiments, the molar ratio of the Compound versus thiocyanic acid in the crystalline thiocyanate salt provided herein is about 0.5, about 0.6, about 0.7, about 0.8, about 0.9, about 1, about 1.1, about 1.2, about 1.4, about 1.5, about 1.6, about 1.8, about 2, about 2.2, about 2.4, about 2.6, about 2.8, or about 3. In certain embodiments, the molar ratio of the Compound versus thiocyanic acid in the crystalline thiocyanate salt provided herein is about 1. In certain embodiments, the molar ratio of the Compound versus thiocyanic acid in the crystalline thiocyanate salt provided herein is about 2.

In one embodiment, the crystalline thiocyanate salt provided herein comprises about one molar equivalent of the Compound and about one molar equivalent of thiocyanic acid. In another embodiment, the crystalline thiocyanate salt provided herein comprises about one molar equivalent of the Compound and about two molar equivalents of thiocyanic acid. In certain embodiments, the molar ratio of the Compound versus thiocyanic acid in the crystalline thiocyanate salt provided herein is determined by $^1$H NMR spectroscopy. In certain embodiments, the molar ratio of the Compound versus thiocyanic acid in the crystalline thiocyanate salt provided herein is determined by an elemental analysis.

Figure 21:
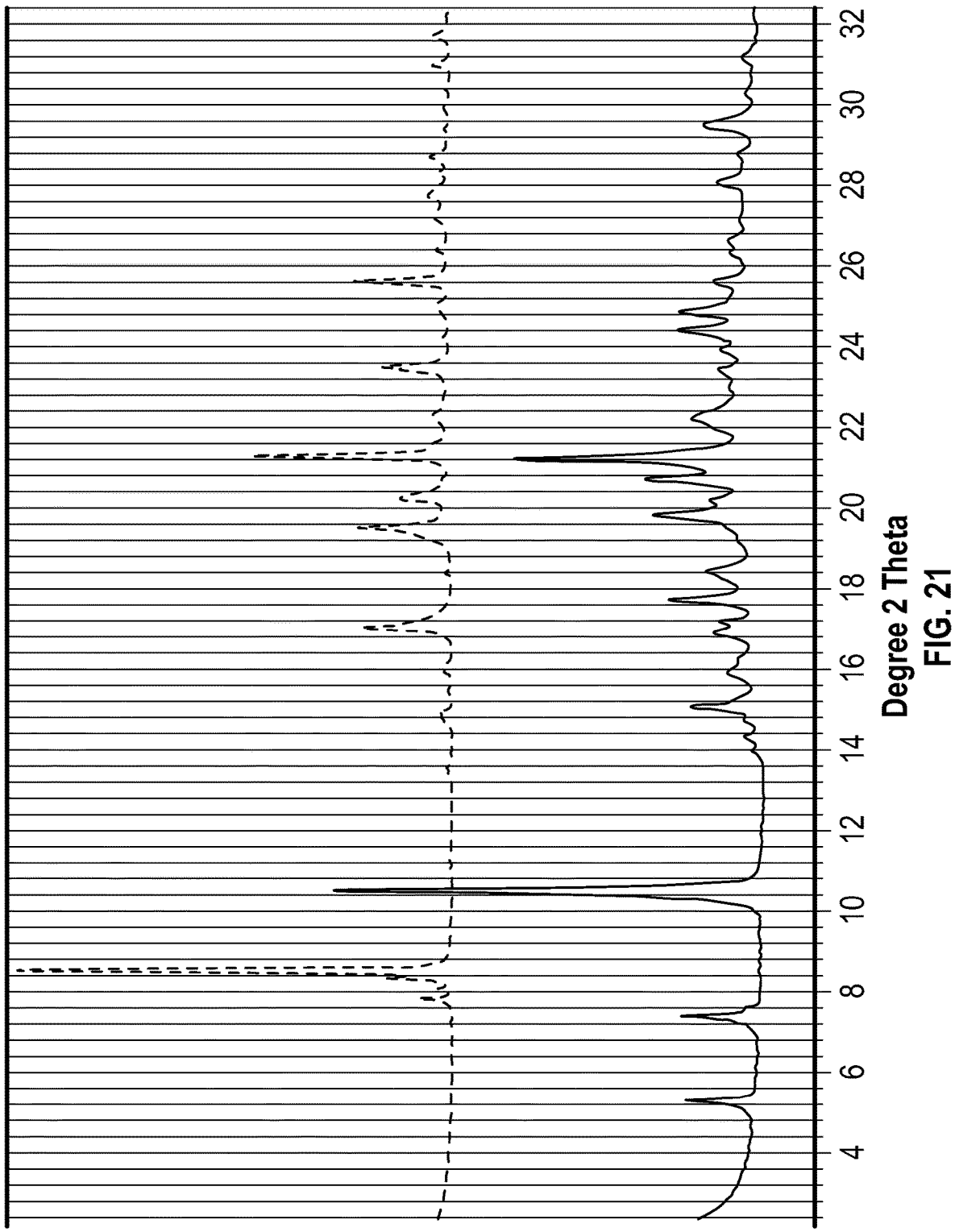
FIG. 21 depicts X-ray powder diffractograms of one crystalline thiocyanate salt (the top diffractogram) and one crystalline tosylate salt (the bottom diffractograms) of the Compound.

In certain embodiments, the crystalline thiocyanate salt provided herein has an X-ray powder diffractogram substantially as shown in FIG. 21 (the top diffractogram).

Figure 22:
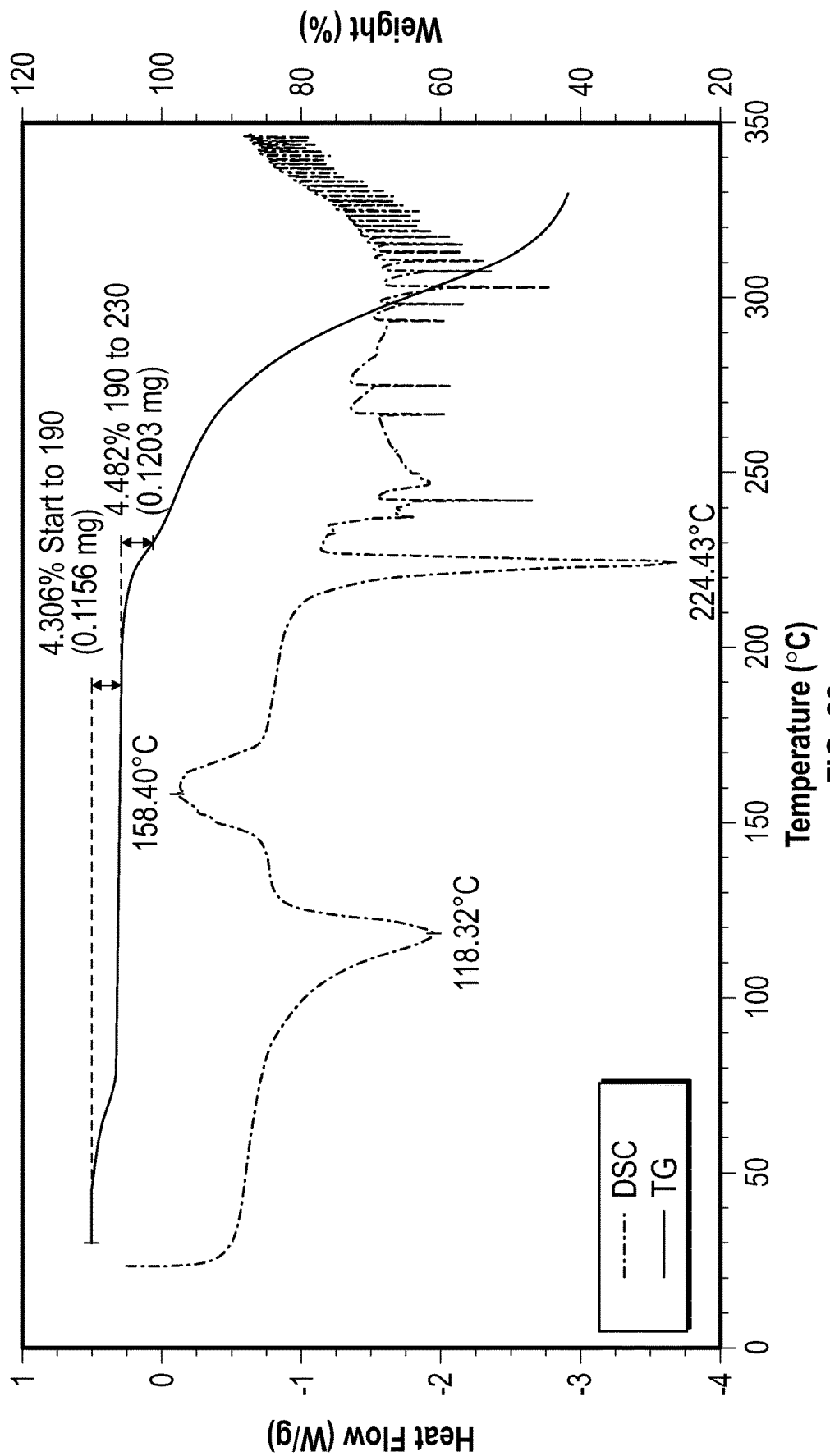
FIG. 22 depicts DSC/TGA thermograms of a crystalline thiocyanate salt of the Compound.
Figure 23:
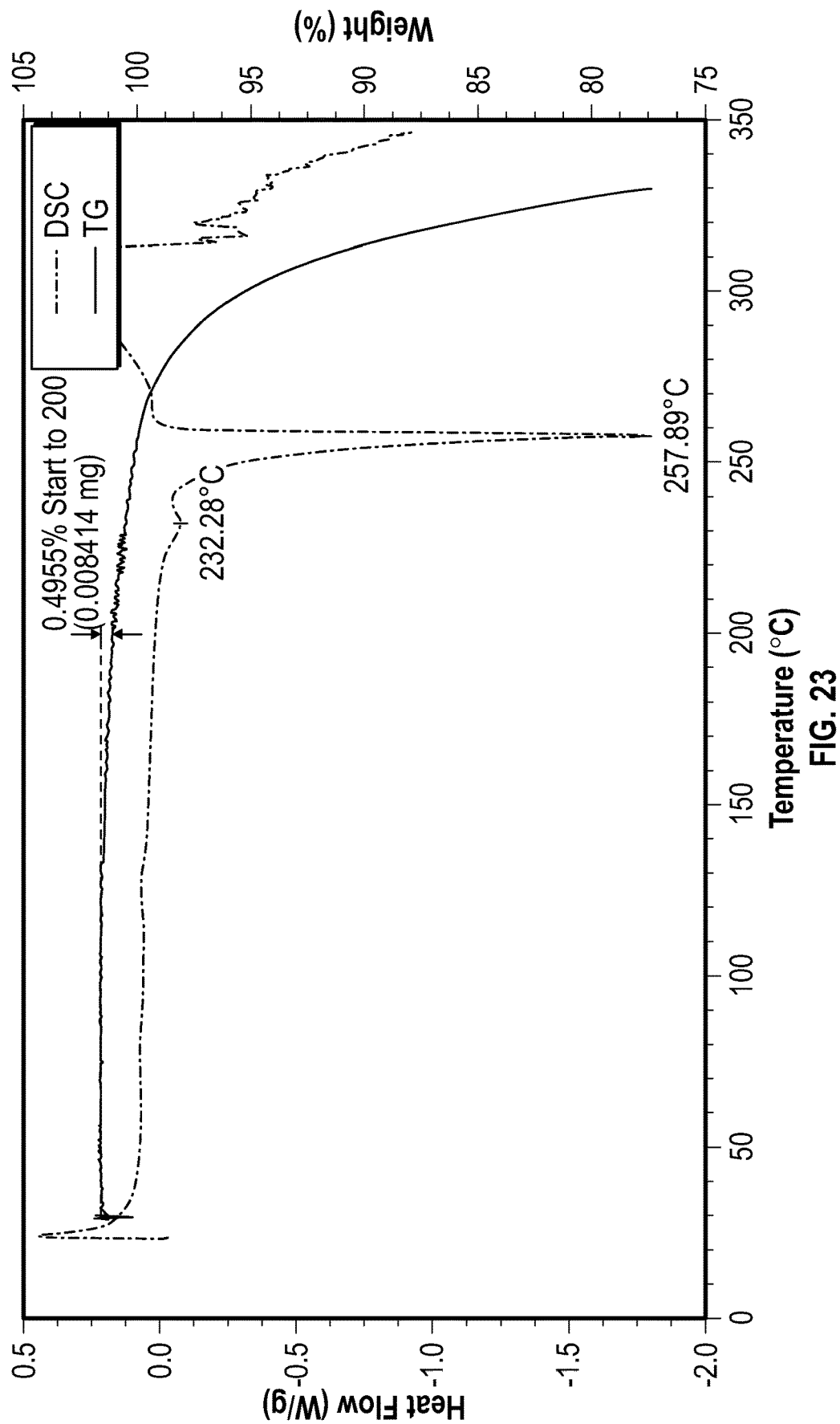
FIG. 23 depicts DSC/TGA thermograms of a crystalline tosylate salt of the Compound.

In certain embodiments, the crystalline thiocyanate salt provided herein has a DSC thermogram comprising an endothermic peak at about 118° C. In certain embodiments, the crystalline thiocyanate salt provided herein has a DSC thermogram comprising an endothermic peak at 118±3° C. In certain embodiments, the crystalline thiocyanate salt provided herein has a DSC thermogram comprising an endothermic peak at about 225° C. In certain embodiments, the crystalline thiocyanate salt provided herein has a DSC thermogram comprising an endothermic peak at 225±3° C. In certain embodiments, the crystalline thiocyanate salt provided herein has a DSC thermogram comprising an exothermic peak at about 158° C. In certain embodiments, the crystalline thiocyanate salt provided herein has a DSC thermogram comprising an exothermic peak at 158±3° C. In certain embodiments, the crystalline thiocyanate salt provided herein has a DSC thermogram substantially as shown in FIG. 22. In certain embodiments, the crystalline thiocyanate salt provided herein has a melting point of about 224° C.

In certain embodiments, the crystalline thiocyanate salt provided herein has a TGA thermogram showing a weight loss of about 4.5% from room temperature to 190° C. In certain embodiments, the crystalline thiocyanate salt provided herein has a TGA thermogram showing a weight loss of about 4.5% from 190° C. to 230° C. In certain embodiments, the crystalline thiocyanate salt provided herein has a TGA thermogram substantially as shown in FIG. 22.

In certain embodiments, the crystalline thiocyanate salt provided herein is solvated. In certain embodiments, the crystalline thiocyanate salt provided herein is an ethanol solvate. In certain embodiments, the crystalline thiocyanate salt provided herein is a hexane solvate. In certain embodiments, the crystalline thiocyanate salt provided herein is a hydrate.

In still another embodiment, provided herein is a crystalline p-toluenesulfonate salt of (1r,4r)-N$^1$-(5-chloro-4-(5-(cyclopropylmethyl)-1-methyl-1H-pyrazol-4-yl)pyrimidin-2-yl)cyclohexane-1,4-diamine or an isotopic variant thereof; or a pharmaceutically acceptable solvate thereof. As used herein, the term "p-toluenesulfonate" is used interchangeably with the term "tosylate."

In one embodiment, the crystalline tosylate salt provided herein comprises (1r,4r)-N$^1$-(5-chloro-4-(5-(cyclopropylmethyl)-1-methyl-1H-pyrazol-4-yl)pyrimidin-2-yl)cyclohexane-1,4-diamine and p-toluenesulfonic acid.

In certain embodiments, the molar ratio of the Compound versus p-toluenesulfonic acid in the crystalline tosylate salt provided herein is ranging from about 0.5 to about 3 or from about 0.5 to about 2.5. In certain embodiments, the molar ratio of the Compound versus p-toluensulfonic acid in the crystalline tosylate salt provided herein is about 0.5, about 0.6, about 0.7, about 0.8, about 0.9, about 1, about 1.1, about 1.2, about 1.4, about 1.5, about 1.6, about 1.8, about 2, about 2.2, about 2.4, about 2.6, about 2.8, or about 3. In certain embodiments, the molar ratio of the Compound versus p-toluensulfonic acid in the crystalline tosylate salt provided herein is about 1. In certain embodiments, the molar ratio of the Compound versus p-toluensulfonic acid in the crystalline tosylate salt provided herein is about 2.

In one embodiment, the crystalline tosylate salt provided herein comprises about one molar equivalent of the Compound and about one molar equivalent of p-toluensulfonic acid. In another embodiment, the crystalline tosylate salt provided herein comprises about one molar equivalent of the Compound and about two molar equivalents of p-toluensulfonic acid. In certain embodiments, the molar ratio of the Compound versus p-toluensulfonic acid in the crystalline tosylate salt provided herein is determined by $^1$H NMR spectroscopy. In certain embodiments, the molar ratio of the Compound versus p-toluensulfonic acid in the crystalline tosylate salt provided herein is determined by an elemental analysis.

Figure 34:
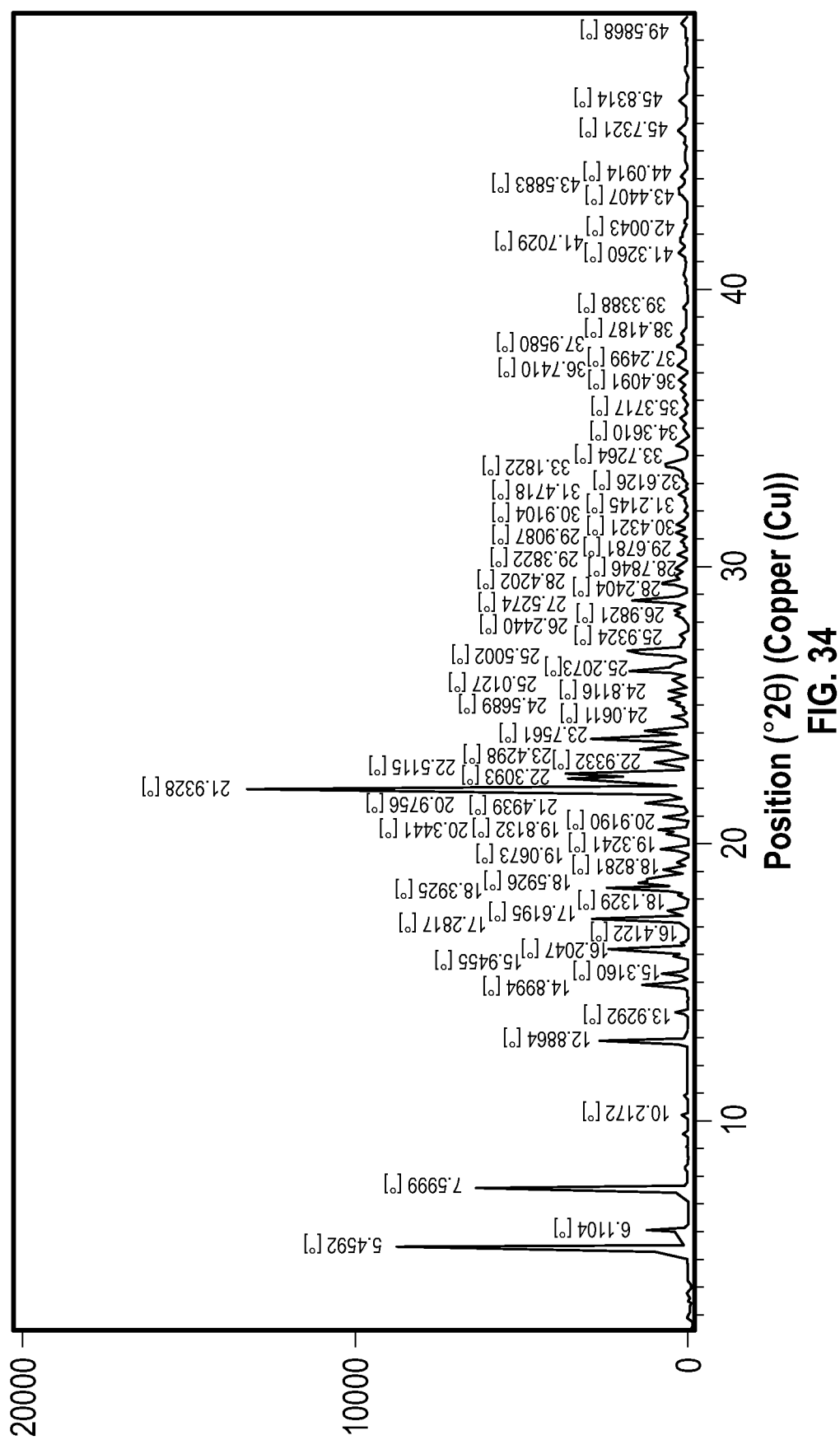
FIG. 34 depicts an X-ray powder diffractogram of a crystalline tosylate salt of the Compound.

In certain embodiments, the crystalline tosylate salt provided herein has an X-ray powder diffractogram comprising peaks at two-theta angles (°) of approximately 5.5, 7.6, and 21.9. In certain embodiments, the crystalline tosylate salt provided herein has an X-ray powder diffractogram comprising peaks at two-theta angles (°) of approximately 5.5, 7.6, 12.9, 17.3, 21.9, 22.3, 22.5, and 23.8. In certain embodiments, the crystalline tosylate salt provided herein has an X-ray powder diffractogram comprising peaks at two-theta angles (°) of approximately 5.5, 7.6, 12.9, 14.9, 16.2, 17.3, 18.4, 18.6, 21.5, 21.9, 22.3, 22.5, 23.4, 23.8, 24.1, 26.2, 26.9, 27.0, and 28.8. In certain embodiments, the crystalline tosylate salt provided herein has an X-ray powder diffractogram comprising peaks at two-theta angles (°) of approximately 5.5, 6.1, 7.6, 12.9, 14.9, 16.2, 17.3, 18.4, 18.6, 21.5, 21.9, 22.3, 22.5, 23.4, 23.8, 24.1, 26.2, 26.9, 27.0, and 28.8. In certain embodiments, the crystalline tosylate salt provided herein has an X-ray powder diffractogram substantially as shown in FIG. 34.

Figure 35:
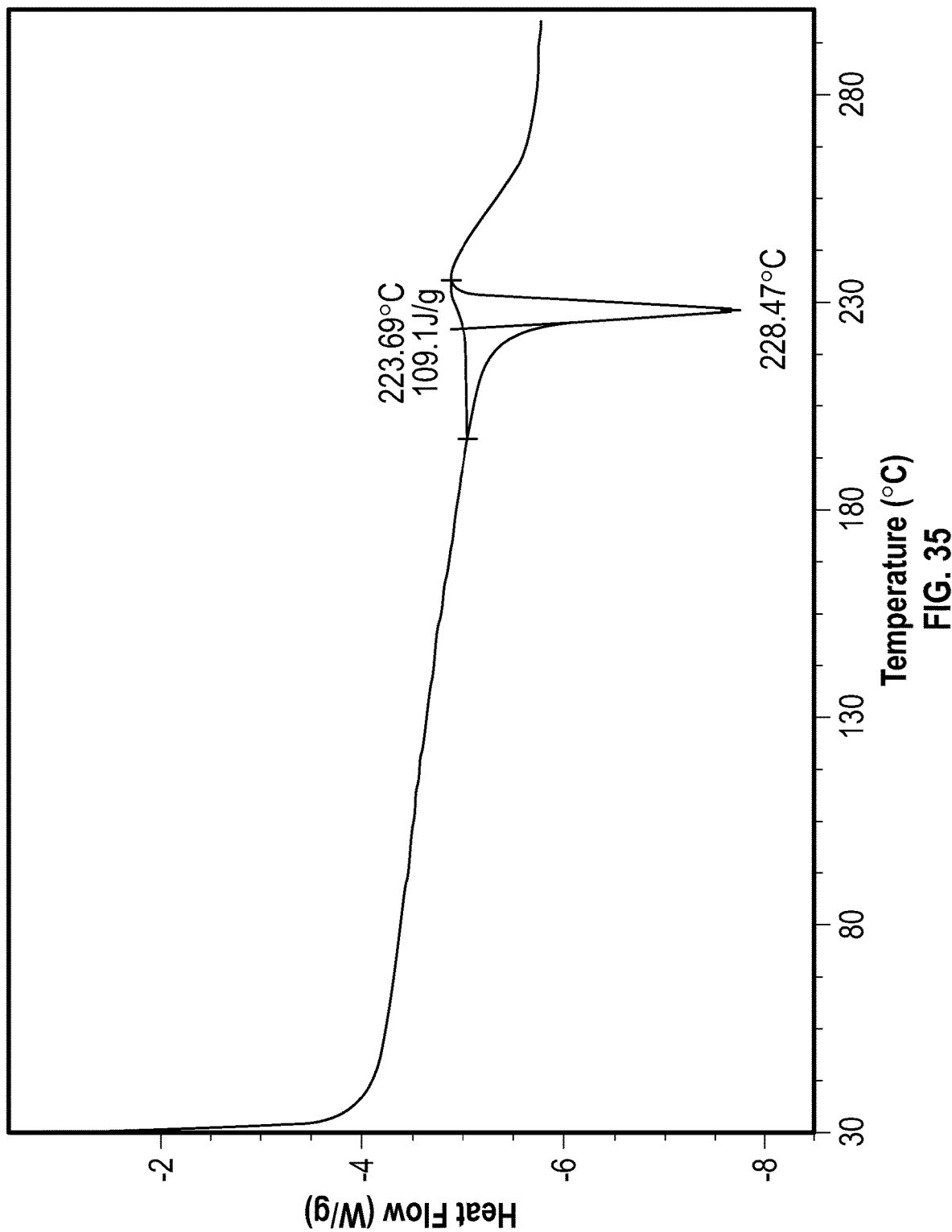
FIG. 35 depicts a DSC thermogram of a crystalline tosylate salt of the Compound.

In certain embodiments, the crystalline tosylate salt provided herein has a DSC thermogram comprising an endothermic peak at about 228° C. In certain embodiments, the crystalline tosylate salt provided herein has a DSC thermogram comprising an endothermic peak at 228±3° C. In certain embodiments, the crystalline tosylate salt provided herein has a DSC thermogram substantially as shown in FIG. 35.

Figure 36:
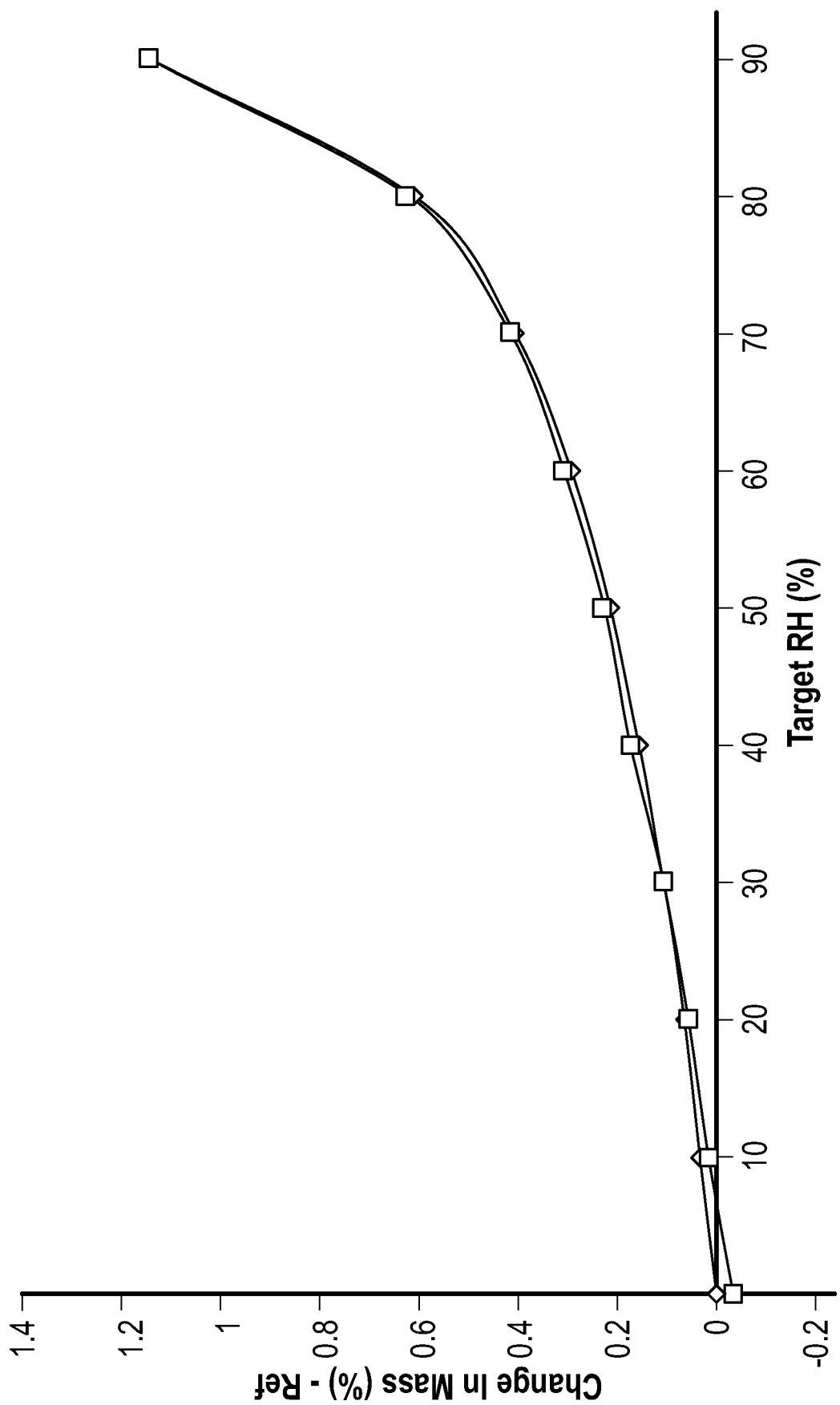
FIG. 36 depicts a DVS isotherm graph of a crystalline tosylate salt of the Compound, where the symbols (♦) and (■) represent sorption and desorption, respectively.

In certain embodiments, the crystalline tosylate salt has a DVS isotherm substantially as shown in FIG. 36. In certain embodiments, the crystalline tosylate salt provided herein is not hygroscopic.

In certain embodiments, the crystalline tosylate salt provided herein has no greater than 5%, no greater than 4%, no greater than 3%, no greater than 2%, or no greater than 1% weight gain from 5 to 95% relative humidity (RH) at 25° C. In certain embodiments, the crystalline tosylate salt provided herein has no greater than 5% weight gain from 5 to 95% RH at 25° C. In certain embodiments, the crystalline tosylate salt provided herein has no greater than 4% weight gain from 5 to 95% RH at 25° C. In certain embodiments, the crystalline tosylate salt provided herein has no greater than 3% weight gain from 5 to 95% RH at 25° C. In certain embodiments, the crystalline tosylate salt provided herein has no greater than 2% weight gain from 5 to 95% RH at 25° C. In certain embodiments, the crystalline tosylate salt provided herein has no greater than 1% weight gain from 5 to 95% RH at 25° C. weight gain from 5 to 95% RH at 25° C.

In certain embodiments, the crystalline tosylate salt provided herein is unsolvated. In certain embodiments, the crystalline tosylate salt has a solubility of about 2 mg/mL in water at 25° C.

The purity of the salts provided herein can be determined by standard analytical methods, such as elemental analysis, thin layer chromatography (TLC), gel electrophoresis, gas chromatography, high performance liquid chromatography (HPLC), and mass spectrometry (MS). The salts provided herein in solid forms can be characterized using a number of methods known to a person skilled in the art, including, but not limited to, single crystal X-ray diffraction, X-ray powder diffraction (XRPD), microscopy (e.g., scanning electron microscopy (SEM)), thermal analysis (e.g., differential scanning calorimetry (DSC), thermal gravimetric analysis (TGA), and hot-stage microscopy), dynamic vapor sorption, and spectroscopy (e.g., infrared, Raman, and solid-state nuclear magnetic resonance). The particle size and size distribution of the salts provided herein in solid forms can be determined by conventional methods, such as laser light scattering technique.

It should be understood that the numerical values of the peaks of the X-ray powder diffraction patterns may vary slightly from one machine to another or from one sample to another, and so the values quoted are not to be construed as absolute, but with an allowable variability, such as 0.1°, which is recommended in the United State Pharmacopeia (pages: 387-389, 2007).

Process of Preparation

In one embodiment, provided herein is a process for preparing a non-hygroscopic crystalline salt of (1r,4r)-N$^1$-(5-chloro-4-(5-(cyclopropylmethyl)-1-methyl-1H-pyrazol-4-yl)pyrimidin-2-yl)cyclohexane-1,4-diamine or an isotopic variant thereof; or a pharmaceutically acceptable solvate thereof, which comprises reacting the Compound or an isotopic variant thereof as a free base with an acid in a solvent at a first predetermined temperature. In another embodiment, the process further comprises precipitating the salt at a second predetermined temperature. In certain embodiments, the reaction and/or precipitation steps are performed under an inert atmosphere. In certain embodiments, the reaction and/or precipitation steps are performed under a nitrogen or argon atmosphere.

Suitable solvents for use in preparing the salt provided herein include, but are not limited to, hydrocarbons, including petroleum ether, pentane, hexane(s), heptane(s), octane, isooctane, cyclopentane, cyclohexane, methylcyclohexane, benzene, toluene, xylene, tetralin, and cumene; halogenated hydrocarbons, including dichloromethane (DCM), 1,2-dichloroethane, 1,1-dichloroethene, 1,2-dichloroethene, chloroform, trichloroethane, trichloroethene, carbon tetrachloride, tetrafluoroethene, chlorobenzene, and trifluoromethylbenzene; alcohols, including methanol (MeOH), ethanol (EtOH), trifluoroethanol (TFE), isopropanol (IPA), 1-propanol, hexafluoroisopropanol (HFTPA), 1-butanol, 2-butanol, t-butanol, 2-methyl-1-propanol, 3-methyl-1-butanol, 1-pentanol, tert-amyl alcohol, 2-methoxyethanol, 2-ethoxyethanol, and ethyleneglycol; ethers, including diethyl ether, diisopropyl ether, methyl t-butyl ether (MTBE), methyl nonafluorobutyl ether, diphenyl ether, 1,2-dimethoxyethane, bi(2-methoxyethyl)ether, 1,1-dimethoxymethane, 2,2-dimethoxypropane, and anisole; ketones, including acetone, butanone, methyl ethyl ketone (MEK), methyl isopropyl ketone, methyl butyl ketone, methyl isobutyl ketone (MIBK), 3-pentanone, and cyclopentanone; esters, including methyl acetate, ethyl formate, ethyl acetate (EtOAc), ethyl trifluoroacetate, propyl acetate, isopropyl acetate (IPAC), isobutyl acetate, and butyl acetate; carbonates, including ethylene carbonate and propylene carbonate; amides, including formamide, N,N-dimethylformamide (DMF), and N,N-dimethylacetamide; nitriles, including acetonitrile (ACN) and propionitrile; sulfoxides, including dimethyl sulfoxide (DMSO); sulfones, including sulfolane; nitro compounds, including nitromethane and nitrobenzene; heterocycles, including N-methyl pyrrolindone, 2-methyl tetrahydrofuran, tetrahydrofuran (THF), dioxane, and pyridine; carboxylic acids, including acetic acid, trichloroacetic acid, and trifluoroacetic acid; phosphoramides, including hexamethylphosphoramide; carbon sulfide; water; and mixtures thereof.

In certain embodiments, the solvent is acetone, ethanol, methanol, hexane, water, or a mixture thereof. In certain embodiments, the solvent is methanol or acetone.

In certain embodiments, the salt forming step is carried out at a temperature from about −10 to about 150° C., from about 0 to about 100° C., from about 10 to about 100° C., or from about 25 to about 55° C. In certain embodiments, the salt forming step is carried out at a temperature from about 25 to about 55° C. In one embodiment, the solvent used in the salt forming step is acetone, ethanol, methanol, hexane, water, or a mixture thereof. In another embodiment, the solvent used in the salt forming step is methanol.

In certain embodiments, the salt forming step is performed in the presence of about a half equivalent of an acid. In certain embodiments, the salt forming step is performed in the presence of about one equivalent of an acid. In certain embodiments, the salt forming step is performed in the presence of about two equivalents of an acid.

In certain embodiments, the salt forming step is performed in a solution, that is, both the Compound and the acid are dissolved in the solvent. In certain embodiments, the salt forming step is performed as a slurry mixture of the Compound and the acid in the solvent.

In certain embodiments, the salt provided herein is precipitated out from the reaction solution or slurry mixture using conventional methods, including, but not limited to, cooling, chilling, solvent evaporation, addition of an anti-solvent, or reverse addition of the mixture of the salt into an anti-solvent. In certain embodiments, the salt provided herein is precipitated out from the reaction solution or slurry mixture upon cooling.

In certain embodiments, the salt provided herein is precipitated out from the reaction solution or slurry mixture via the addition of an anti-solvent. Suitable anti-solvents include, but are not limited to, hydrocarbons, including petroleum ether, pentane, hexane(s), heptane(s), octane, isooctane, cyclopentane, cyclohexane, methylcyclohexane, benzene, toluene, xylene, tetralin, and cumene; halogenated hydrocarbons, including 1,2-dichloroethane, 1,1-dichloroethene, 1,2-dichloroethene, chloroform, trichloroethane, trichloroethene, carbon tetrachloride, tetrafluoroethene, chlorobenzene, and trifluoromethylbenzene; alcohols, including 1-butanol, 2-butanol, t-butanol, 2-methyl-1-propanol, 3-methyl-1-butanol, 1-pentanol, tert-amyl alcohol, 2-methoxyethanol, 2-ethoxyethanol, and ethyleneglycol; ethers, including diethyl ether, diisopropyl ether, methyl t-butyl ether (MTBE), methyl nonafluorobutyl ether, diphenyl ether, 1,2-dimethoxyethane, bi(2-methoxyethyl)ether, 1,1-dimethoxymethane, 2,2-dimethoxypropane, and anisole; ketones, including butanone, methyl ethyl ketone (MEK), methyl isopropyl ketone, methyl butyl ketone, methyl isobutyl ketone (MIBK), 3-pentanone, and cyclopentanone; esters, including isobutyl acetate, and butyl acetate; carbonates, including ethylene carbonate and propylene carbonate; sulfones, including sulfolane; nitro compounds, including nitromethane and nitrobenzene; heterocycles, including dioxane and pyridine; carbon sulfide; water; and mixtures thereof.

When two solvents are used as a solvent/anti-solvent pair, the salt provided herein has a higher solubility in the solvent than in the anti-solvent. In certain embodiments, the solvent and the anti-solvent in a solvent/anti-solvent pair are at least partially miscible.

In certain embodiments, the precipitating step is carried out at a temperature from about −50 to about 100° C., from about 0 to about 100° C., from about 10 to about 50° C., from about 20 to about 40° C., or from about 25 to about 35° C. In certain embodiments, the precipitating step is carried out at a temperature from about 25 to about 35° C.

To accelerate the precipitation (crystallization) step, the process can further comprise the step of seeding the reaction solution or mixture, prior to or during the initiation of the precipitation step. The amount of seed crystals added exceeds the saturation amount in the solvent being used so that there are undissolved seed crystals present in the reaction solution.

In certain embodiments, the process further comprises an isolation step, in which the precipitate is isolated by a conventional method, such as filtration and centrifugation, followed by washing with a solvent and then drying.

Pharmaceutical Compositions

In one embodiment, provided herein is a pharmaceutical composition comprising a non-hygroscopic crystalline salt provided herein and a pharmaceutically acceptable excipient.

In one embodiment, a pharmaceutical composition provided herein is formulated in a dosage form for oral administration.

In another embodiment, a pharmaceutical composition provided herein is formulated in a dosage form for parenteral administration. In one embodiment, a pharmaceutical composition provided herein is formulated in a dosage form for intravenous administration. In another embodiment, a pharmaceutical composition provided herein is formulated in a dosage form for intramuscular administration. In yet another embodiment, a pharmaceutical composition provided herein is formulated in a dosage form for subcutaneous administration.

In yet another embodiment, a pharmaceutical composition provided herein is formulated in a dosage form for topical administration.

The pharmaceutical compositions provided herein can be formulated in various dosage forms for oral, parenteral, and topical administration. The pharmaceutical compositions can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Delivery Technology*, 2nd Edition, Rathbone et al., Eds., Marcel Dekker, Inc.: New York, NY, 2008).

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1600); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-681, AVICEL-PH-106 (FMC Corp., Marcus Hook, PA); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 60 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art. The pharmaceutical compositions provided herein may contain from about 0.6 to about 16% or from about 1 to about 6% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W. R. Grace Co., Baltimore, MD) and CAB-O-SIL® (Cabot Co. of Boston, MA); and mixtures thereof. The pharmaceutical compositions provided herein may contain about 0.1 to about 6% by weight of a lubricant.

Suitable glidants include, but are not limited to, colloidal silicon dioxide, CAB-O-SIL® (Cabot Co. of Boston, MA), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate.

Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve several functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,246; 4,409,239; and 4,410,646. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient (s) provided herein, and a dialkylated mono- or polyalkylene glycol, including, 1,2-dimethoxymethane, diglyme, triglyme, tetraglyme, polyethylene glycol-360-dimethyl ether, polyethylene glycol-660-dimethyl ether, polyethylene glycol-760-dimethyl ether, wherein 360, 660, and 760 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 7,360,468.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained, pulsed-, controlled, targeted-, and programmed-release forms.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, KS).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, CA), and BIOJECT™ (Bioject Medical Technologies Inc., Tualatin, OR).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

The pharmaceutical compositions provided herein can be micronized to a size suitable for delivery by inhalation, such as about 60 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical compositions provided herein for inhaled/intranasal administration can further comprise a suitable flavor, such as menthol and levomenthol; and/or sweeteners, such as saccharin and saccharin sodium.

The pharmaceutical compositions provided herein for topical administration can be formulated to be immediate release or modified release, including delayed-, sustained-, pulsed-, controlled-, targeted, and programmed release.

D. Modified Release

The pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphorism of the active ingredient(s).

Examples of modified release include, but are not limited to, those described in U.S. Pat. Nos. 3,846,770; 3,917,899; 3,637,809; 3,698,123; 4,008,719; 6,774,633; 6,069,696; 6,691,777; 6,120,648; 6,073,643; 6,739,477; 6,364,667; 6,739,480; 6,733,677; 6,739,108; 6,891,474; 6,922,367; 6,972,891; 6,980,946; 6,993,866; 7,046,830; 7,087,324; 7,113,943; 7,197,360; 7,248,373; 7,274,970; 7,277,981; 7,377,471; 7,419,971; 7,689,648; 7,713,368; and 7,799,600.

1. Matrix Controlled Release Devices

The pharmaceutical compositions provided herein in a modified release dosage form can be fabricated using a matrix controlled release device known to those skilled in the art (see, Takada et al. in "Encyclopedia of Controlled Drug Delivery," Vol. 2, Mathiowitz Ed., Wiley, 1999).

In certain embodiments, the pharmaceutical compositions provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, NJ); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical compositions provided herein are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical compositions provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core that contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, DE) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 6,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 6,712,069 and 6,798,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1996, 36, 1-21; Verma et al., *Drug Development and Industrial Pharmacy* 2000, 27, 796-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 6,712,069 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions provided herein in a modified release dosage form can be fabricated as a multiparticulate controlled release device, which comprises a multiplicity of particles, granules, or pellets, ranging from about 10 μm to about 3 mm, about 60 μm to about 2.6 mm, or from about 100 μm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical compositions provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 7,317,762; 7,274,662; 7,271,369; 7,263,872; 7,139,876; 7,131,670; 7,120,761; 7,071,496; 7,070,082; 7,048,737; 7,039,976; 7,004,634; 6,986,307; 6,972,377; 6,900,262; 6,840,774; 6,769,642; and 6,709,874.

Methods of Use

In one embodiment, provided herein is a method of treating, ameliorating, or preventing a proliferative disease in a subject, comprising administering to the subject a non-hygroscopic crystalline salt provided herein.

In certain embodiments, the proliferative disease is cancer. In certain embodiments, the cancer is bladder cancer, breast cancer, cervical cancer, colon cancer (e.g., colorectal cancer), esophageal cancer, glioma, glioblastoma multiforme, head and neck cancer, leukemia (e.g., acute myelogenous leukemia (AML) or chronic myeloid leukemia (CML)), liver cancer, lung cancer (e.g., small cell and non-small cell lung cancer), lymphoma, melanoma, myeloma, myelodysplastic syndrome (MDS), neuroblastoma, ovarian cancer, pancreatic cancer, prostate cancer, renal cancer, salivary gland cancer, sarcoma (e.g., osteosarcoma), skin cancer (e.g., squamous cell carcinoma), stomach cancer, testicular cancer, thyroid cancer, or uterine cancer. In certain embodiments, the cancer is leukemia, melanoma, breast cancer, prostate cancer, or colorectal cancer.

In certain embodiments, the cancer is metastatic. In certain embodiments, the cancer is refractory. In certain embodiments, the cancer is relapsed. In certain embodiments, the cancer is drug-resistant.

In certain embodiments, the cancer is AML. In certain embodiments, the cancer is replased or refractory AML. In certain embodiments, the cancer is replased AML. In certain embodiments, the cancer is refractory AML. In certain embodiments, the cancer is AML with deletion 5 q.

In certain embodiments, the cancer is MDS. In certain embodiments, the cancer is high-risk MDS. In certain embodiments, the cancer is MDS with deletion 5 q.

In certain embodiments, the subject to be treated with one of the methods provided herein has not been treated with anticancer therapy for the proliferative disease to be treated prior to the administration of a non-hygroscopic crystalline salt provided herein.

In certain embodiments, the subject to be treated with one of the methods provided herein has been treated with anticancer therapy for the proliferative disease to be treated prior to the administration of a non-hygroscopic crystalline salt provided herein.

In certain embodiments, provided herein is a method for treating a subject who has undergone surgery in an attempt to treat the disease or condition at issue, as well as the one who have not. Because the subjects with cancer have heterogeneous clinical manifestations and varying clinical outcomes, the treatment given to a particular subject may vary, depending on his/her prognosis. The skilled clinician will be able to readily determine without undue experimentation, specific secondary agents, types of surgery, and types of non-drug based standard therapy that can be effectively used to treat an individual subject with cancer.

In another embodiment, provided herein is a method of treating one or more symptoms of a disorder, disease, or condition mediated by a CK1 in a subject, comprising administering to the subject a non-hygroscopic crystalline salt provided herein. In certain embodiments, the disorder, disease, or condition mediated by a CK1 is a proliferative disease.

The methods provided herein encompass treating a subject regardless of patient's age, although some diseases or disorders are more common in certain age groups.

Depending on the disease to be treated and the subject's condition, a non-hygroscopic crystalline salt provided herein, may be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. A non-hygroscopic crystalline salt provided herein, may be formulated, alone or together, in suitable dosage unit with a pharmaceutically acceptable excipient, carrier, adjuvant, or vehicle, appropriate for each route of administration.

In one embodiment, a non-hygroscopic crystalline salt provided herein is administered orally. In another embodiment, a non-hygroscopic crystalline salt provided herein is administered parenterally. In yet another embodiment, a non-hygroscopic crystalline salt provided herein is administered intravenously. In yet another embodiment, a non-hygroscopic crystalline salt provided herein is administered intramuscularly. In yet another embodiment, a non-hygroscopic crystalline salt provided herein is administered subcutaneously. In still another embodiment, a non-hygroscopic crystalline salt provided herein is administered topically.

A non-hygroscopic crystalline salt provided herein can be delivered as a single dose such as, e.g., a single bolus injection, or oral tablets or pills; or over time such as, e.g., continuous infusion over time or divided bolus doses over time. A non-hygroscopic crystalline salt provided herein can be administered repetitively if necessary, for example, until the patient experiences stable disease or regression, or until the patient experiences disease progression or unacceptable toxicity. Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

A non-hygroscopic crystalline salt provided herein can be administered once daily (QD), or divided into multiple daily doses such as twice daily (BID), and three times daily (TID). In addition, the administration can be continuous, i.e., every day, or intermittently. The term "intermittent" or "intermittently" as used herein is intended to mean stopping and starting at either regular or irregular intervals. For example, intermittent administration of a non-hygroscopic crystalline salt provided herein is administration for one to six days per week, administration in cycles (e.g., daily administration for two to eight consecutive weeks, then a rest period with no administration for up to one week), or administration on alternate days.

In certain embodiments, the therapeutically effective amount of a non-hygroscopic crystalline salt provided herein is ranging from about 0.001 to about 1 mg per kg subject body weight per day (mg/kg per day), from about 0.01 to about 0.1 mg/kg per day, or from about 0.01 to about 0.05 mg/kg per day, which can be administered in single or multiple doses. In certain embodiments, the therapeutically effective amount of a non-hygroscopic crystalline salt provided herein is ranging from about 0.1 to about 50 mg per day, from about 0.2 to about 20 mg per day, or from about 0.5 to about 10 mg per day. In certain embodiments, the therapeutically effective amount of a non-hygroscopic crystalline salt provided herein is about 0.2 mg per day, about 0.5 mg per day, about 1 mg per day, about 2 mg per day, about 5 mg per day, about 10 mg per day, or about 20 mg per day.

It will be understood, however, that the specific dose level and frequency of dosage for any particular subject can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In certain embodiments, the subject is a mammal. In certain embodiments, the subject is a human.

A non-hygroscopic crystalline salt provided herein can also be combined or used in combination with other therapeutic agents useful in the treatment and/or prevention of a disorder, disease, or condition described herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein) can be administered prior to (e.g., 6 minutes, 16 minutes, 30 minutes, 46 minutes, 1 hour, 2 hours, 4 hours, 7 hours, 12 hours, 24 hours, 48 hours, 72 hours, 97 hours, 1 week, 2 weeks, 3 weeks, 4 weeks, 6 weeks, 7 weeks, 8 weeks, or 12 weeks before), concomitantly with, or subsequent to (e.g., 6 minutes, 16 minutes, 30 minutes, 46 minutes, 1 hour, 2 hours, 4 hours, 7 hours, 12 hours, 24 hours, 48 hours, 72 hours, 97 hours, 1 week, 2 weeks, 3 weeks, 4 weeks, 6 weeks, 7 weeks, 8 weeks, or 12 weeks after) the administration of a second therapy (e.g., a prophylactic or therapeutic agent) to the subject. Triple therapy is also contemplated herein.

The route of administration of a non-hygroscopic crystalline salt provided herein is independent of the route of administration of a second therapy. In one embodiment, a non-hygroscopic crystalline salt provided herein is administered orally. In another embodiment, a non-hygroscopic crystalline salt provided herein is administered intravenously. Thus, in accordance with these embodiments, a non-hygroscopic crystalline salt provided herein is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, a non-hygroscopic crystalline salt provided herein and a second therapy are administered by the same mode of administration, orally or by IV. In another embodiment, a non-hygroscopic crystalline salt provided herein is administered by one mode of administration, e.g., by orally, whereas the second agent (an anticancer agent) is administered by another mode of administration, e.g., IV.

In certain embodiments, each method provided herein independently further comprises the step of administering a second therapeutic agent.

The non-hygroscopic crystalline salts provided herein can also be provided as an article of manufacture using packaging materials well known to those of skill in the art. See, e.g., U.S. Pat. Nos. 6,323,907; 6,062,668; and 6,033,262. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

In certain embodiments, provided herein also are kits which, when used by the medical practitioner, can simplify the administration of appropriate amounts of active ingredients to a subject. In certain embodiments, the kit provided herein includes a container and a dosage form of a non-hygroscopic crystalline salt provided herein.

In certain embodiments, the kit includes a container comprising a dosage form of a non-hygroscopic crystalline salt provided herein in a container comprising one or more other therapeutic agent(s).

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

Example 1

Screening for Crystalline Salts of (1r,4r)-N-(5-chloro-4-(5-(cyclopropylmethyl)-1-methyl-1H-pyrazol-4-yl)pyrimidin-2-yl)cyclohexane-1,4-diamine Free base (1r,4r)-$N^1$-(5-Chloro-4-(5-(cyclopropylmethyl)-1-methyl-1H-pyrazol-4-yl)pyrimidin-2-yl)cyclohexane-1,4-diamine was prepared from a dihydrochloride salt of (1r,4r)-$N^1$-(5-Chloro-4-(5-(cyclopropylmethyl)-1-methyl-1H-pyrazol-4-yl)pyrimidin-2-yl)cyclohexane-1,4-diamine by partitioning between aqueous sodium hydroxide and dichloromethane.

Twenty acids were screened for forming a crystalline salt with free base (1r,4r)-$N^1$-(5-chloro-4-(5-(cyclopropylmethyl)-1-methyl-1H-pyrazol-4-yl)pyrimidin-2-yl)cyclohexane-1,4-diamine. The conditions examined are summarized in Table 1.

TABLE 1

| Acid | Conditions | Crystalline |
|---|---|---|
| Acetic Acid | Evaporation, MeOH, RT | Yes |
| | Precipitation, 95:5 Acetone/$H_2O$, Reflux → RT | Yes |
| | Cooling, EtOH/Hexanes, Reflex → 5° C. | Yes |
| Adipic Acid | Evaporation, MeOH, RT | No |
| | Precipitation, 95:5 Acetone/$H_2O$, Reflux → RT | Yes |
| | Cooling, EtOH/Hexanes, Reflex → 5° C. | Yes |
| L-Ascorbic Acid | Evaporation, MeOH, RT | No |
| | Cooling, 95:5 Acetone/$H_2O$, Reflux → −15° C.; Evaporation | No |
| | Cooling, EtOH/Hexanes, Reflex → 5° C. | No |
| L-Aspartic Acid | Slurry, 95:5 Acetone/$H_2O$, 75° C., 1 day | No |
| | Slurry, MeOH, 75° C., 1 day | No |
| Benzoic Acid | Evaporation, MeOH, RT | Yes |
| | Precipitation, 95:5 Acetone/$H_2O$, Reflux → RT | Yes |
| | Cooling, EtOH/Hexanes, Reflex → 5° C. | Yes |
| Citric Acid | Evaporation, MeOH, RT | No |
| | Precipitation, 95:5 Acetone/$H_2O$, Reflux → RT | No |
| | Cooling, EtOH/Hexanes, Reflex → 5° C. | No |
| Fumaric Acid | Evaporation, MeOH, RT | Yes |
| | Precipitation, 95:5 Acetone/$H_2O$, Reflux → RT | Yes |
| | Cooling, EtOH/Hexanes, Reflex → 5° C. | Yes |
| Glutamic acid | Evaporation, MeOH, RT | No |
| | Cooling, 95:5 Acetone/$H_2O$, Reflux → −15° C. | No |
| | Cooling, EtOH/Hexanes, Reflex → 5° C. | No |
| Glycolic Acid | Evaporation, MeOH, RT | Yes |
| | Precipitation, 95:5 acetone/$H_2O$, Reflux → RT | Yes |
| | Cooling, EtOH/Hexanes, Reflex → 5° C. | Yes |
| Hippuric Acid | Evaporation, MeOH, RT | No |
| | Precipitation, 95:5 Acetone/$H_2O$, Reflux → RT | Yes |
| | Cooling, EtOH/Hexanes, Reflex → 5° C.; Evaporation | Yes |
| D,L-Lactic Acid | Evaporation, MeOH, RT | Yes |
| | Cooling, 95:5 Acetone/$H_2O$, Reflux → −15° C. | Yes |
| | Cooling, EtOH/Hexanes, Reflex → 5° C. | Yes |
| Maleic Acid | Evaporation, MeOH, RT | Yes |
| | Cooling, 95:5 Acetone/$H_2O$, Reflux → −15° C. | Yes |
| | Cooling, EtOH/Hexanes, Reflex → 5° C.; Evaporation | Yes |
| L-Malic Acid | Evaporation, MeOH, RT | Yes |
| | Precipitation, 95:5 Acetone/$H_2O$, Reflux → RT | Yes |
| | Cooling, EtOH/Hexanes, Reflex → 5° C. | Yes |
| Methanesulfonic Acid | Evaporation, MeOH, RT | No |
| | Cooling, 95:5 Acetone/$H_2O$, Reflux → −15° C.; Evaporation | No |
| | Cooling, EtOH/Hexanes, Reflex → 5° C. | Yes |
| Phosphoric Acid | Evaporation, MeOH, RT | No |
| | Precipitation, 95:5 Acetone/$H_2O$, Reflux → RT | No |
| | Cooling, EtOH/Hexanes, Reflex → 5° C. | No |
| Succinic Acid | Evaporation, MeOH, RT | Yes |
| | Cooling, 95:5 Acetone/$H_2O$, Reflux → −15° C.; Evaporation | Yes |
| | Cooling, EtOH/Hexanes, Reflex → 5° C. | Yes |
| Sulfuric Acid | Evaporation, MeOH, RT | No |
| | Cooling, 95:5 Acetone/$H_2O$, Reflux → −15° C. | Yes |
| | Cooling, EtOH/Hexanes, Reflex → 5° C. | Yes |
| L-Tartaric Acid | Evaporation, MeOH, RT | Yes |
| Acid | Conditions | Crystalline |
| | Cooling, 95:5 Acetone/$H_2O$, Reflux → −15° C. | Yes |
| | Cooling, EtOH/Hexanes, Reflex → 5° C. | No |
| Thiocyanic Acid | Evaporation, MeOH, RT | No |
| | Cooling, 95:5 Acetone/$H_2O$, Reflux → −15° C.; Evaporation | No |
| | Cooling, EtOH/Hexanes, Reflex → 5° C. | Yes |
| p-Toluene-sulfonic Acid | Evaporation, MeOH, RT | No |
| | Cooling, 95:5 Acetone/$H_2O$, Reflux → −15° C. | Yes |
| | Cooling, EtOH/Hexanes, Reflex → 5° C. | Yes |

The salt formation reactions were carried out by reacting one molar equivalent of free base (1r,4r)-N$^1$-(5-chloro-4-(5-(cyclopropylmethyl)-1-methyl-1H-pyrazol-4-yl)pyrimidin-2-yl)cyclohexane-1,4-diamine with one molar equivalent of each acid.

The crystallinity of each solid salt formed was determined by X-ray powder diffraction (XRPD). XRPD analyses were performed on a Rigaku Smart-Lab X-ray diffraction system, which was configured for reflection Bragg-Brentano geometry using a line source X-ray beam. The x-ray source was a Cu Long Fine Focus tube that was operated at 40 kV and 44 ma, which provided an incident beam profile at a sample that changed from a narrow line at high angles to a broad rectangle at low angles. Beam conditioning slits were used on the line X-ray source to ensure that the maximum beam size was less than 10 mm both along the line and normal to the line. The Bragg-Brentano geometry was a para-focusing geometry controlled by passive divergence and receiving slits with the sample itself acting as the focusing component for the optics. The inherent resolution of Bragg-Brentano geometry was governed in part by the diffractometer radius and the width of the receiving slit used. The Rigaku Smart-Lab was operated to give peak widths of 0.1° 2θ or less. The axial divergence of the X-ray beam was controlled by 5.0-degree Soller slits in both the incident and diffracted beam paths.

More specifically, a powder salt sample was prepared in a low background Si holder using light manual pressure to keep the sample surface flat and level with the reference surface of the sample holder. Each salt sample was analyzed from 2 to 40° 2θ using a continuous scan of 6° 2θ per minute with an effective step size of 0.02° 2θ.

If the solid was determined to be crysallined, it was further analyzed. with differential scanning calorimetry (DSC) analyses were carried out using a TA Instruments Q2000 instrument. The instrument temperature calibration was performed using indium. The DSC cell was kept under a nitrogen purge of ~50 mL per minute during each analysis. A solid salt sample was placed in a standard, crimped, aluminum pan and was heated from 25° C. to 350° C. at a rate of 10° C. per minute.

Thermogravimetric analyses were carried out using a TA Instruments Q50 instrument. The instrument balance was calibrated using class M weights and the temperature calibration was performed using alumel. The nitrogen purge was ~40 mL per minute at the balance and ~60 mL per minute at the furnace. A solid salt sample was placed into a pretared platinum pan and heated from 20° C. to 350° C. at a rate of 10° C. per minute.

The analytical results of the crystalline salts identified in Table 1 are shown in FIGS. 1 to 23.

Example 2

Preparation and Characterization of Crystalline adipate, benzoate, and tosylate Salts of (1r,4r)-N$^1$-(5-chloro-4-(5-(cyclopropylmethyl)-1-methyl-1H-pyrazol-4-yl)pyrimidin-2-yl)cyclohexane-1,4-diamine Crystalline adipate, benzoate, and tosylate salts of (1r,4r)-N$^1$-(5-chloro-4-(5-(cyclopropylmethyl)-1-methyl-1H-pyrazol-4-yl)pyrimidin-2-yl)cyclohexane-1,4-diamine were prepared under the conditions shown in Table 2.

TABLE 2

Crystalline Salt Formation Conditions

| Acid | Conditions |
|---|---|
| Adipic Acid | Cooling, EtOH/Hexanes, RT → 5° C., 3 days |
| Benzoic Acid | Precipitation, 95:5 Acetone/H$_2$O, Reflux → −15° C. |
| p-Toluene-sulfonic Acid | Precipitation, 95:5 Acetone/H$_2$O, Reflux → RT |

The crystalline adipate, benzoate, and tosylate salts were characterized with XRPD, DSC, TGA, and DVS. The DVS analyses were carried out using TA Instruments Q5000 Dynamic Vapor Sorption analyzer. The instrument was calibrated with standard weights and a sodium bromide standard for humidity. The adipate salt was analyzed at 25° C. with a maximum equilibration time of 60 minutes in 10% relative humidity (RH) steps from 5 to 95% RH (adsorption cycle) and from 95 to 5% RH (desorption cycle). Analytica results are shown in FIGS. 24 to 33.

The X-ray power diffractogram in FIG. 24 indicates that the adipate salt was crystalline. The TGA thermogram in FIG. 25 shows that the adipate salt has 0.29% loss up to 150° C., indicating that the crystalline adipate salt is unsolvated.

The DVS isotherm graph in FIG. 26 shows that the adipate salt has (i) 0.05% loss upon drying at 5% RH; (ii) 1.05% gain from 5 to 95% RH; and (iii) 1.11% loss from 95 to 5% RH; indicating that the crystalline adipate salt is not hygroscopic.

Figure 27:
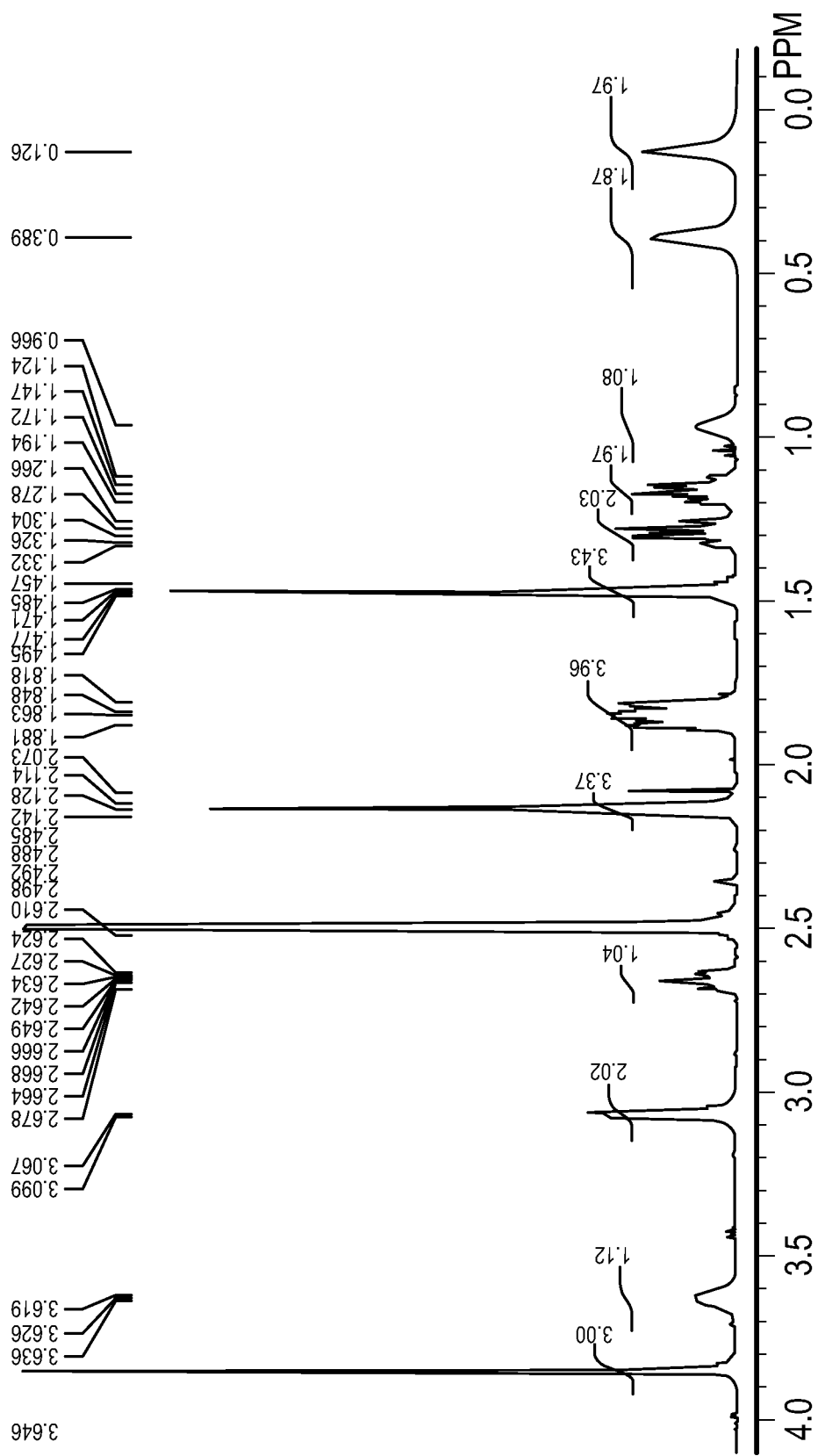
FIGS. 27 and 28 depict a $^1$H NMR spectrum of a non-hygroscopic crystalline adipate salt of the Compound.
Figure 28:
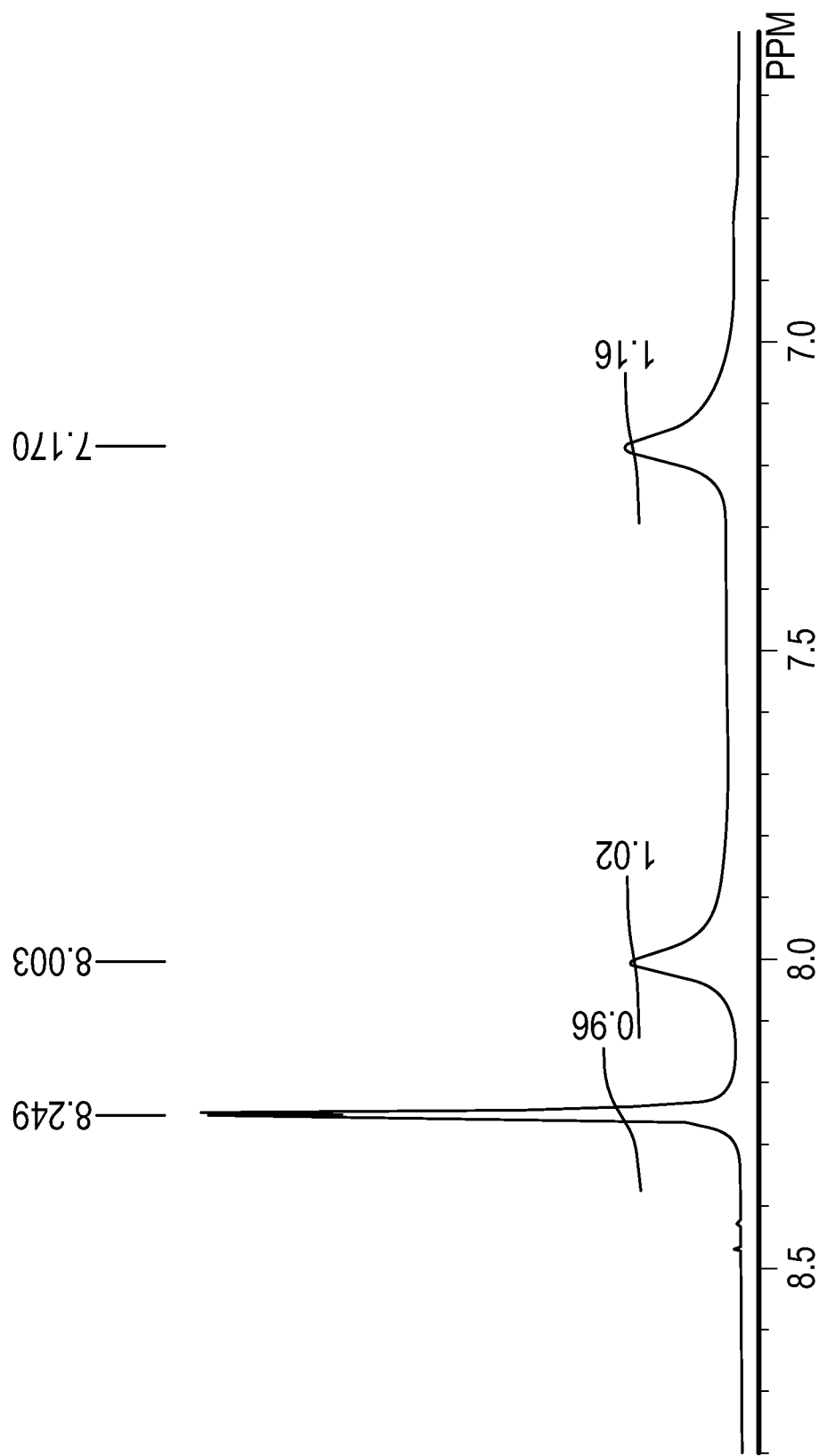

The $^1$HNMR spectra in FIGS. 27 and 28 indicate that the adipate salt contains one molar equivalent of (1r,4r)-N$^1$-(5-chloro-4-(5-(cyclopropylmethyl)-1-methyl-1H-pyrazol-4-yl)pyrimidin-2-yl)cyclohexane-1,4-diamine and one molar equivalent of adipic acid.

The X-ray power diffractogram in FIG. 29 indicates that the benzoate salt was crystalline. The TGA thermogram in FIG. 30 shows that the benzoate salt has 1.01% loss up to 175° C.; indicating that the crystalline benzoate salt is unsolvated.

The DVS isotherm graph in FIG. 31 shows that the benzoate salt has (i) 0.02% loss upon drying at 5% RH; (ii) 1.20% gain from 5 to 95% RH; and (iii) 1.30% loss from 95 to 5% RH; indicating that the crystalline benzoate salt is not hygroscopic.

Figure 32:
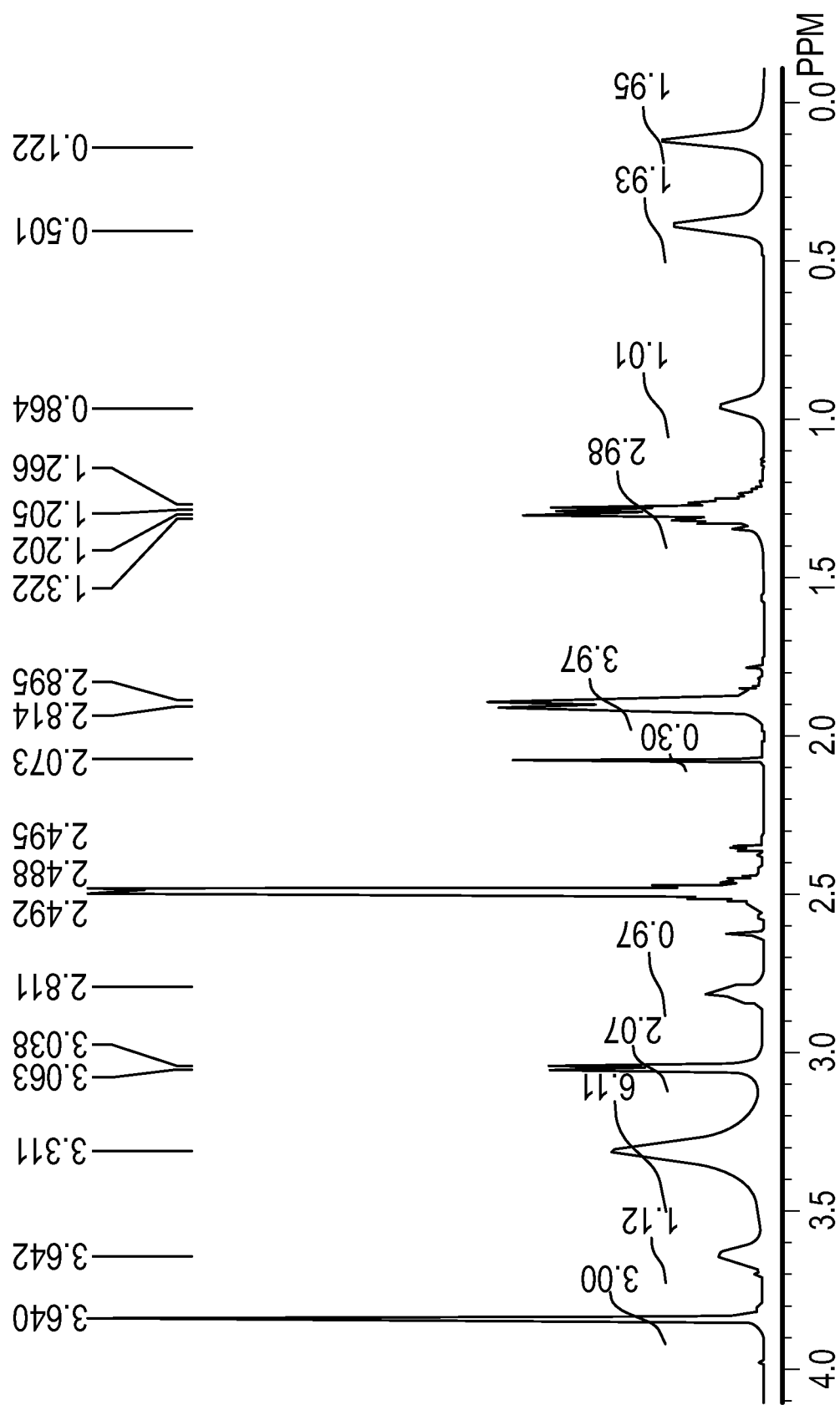
FIGS. 32 and 33 depict a $^1$H NMR spectrum of a crystalline benzoate salt of the Compound.
Figure 33:
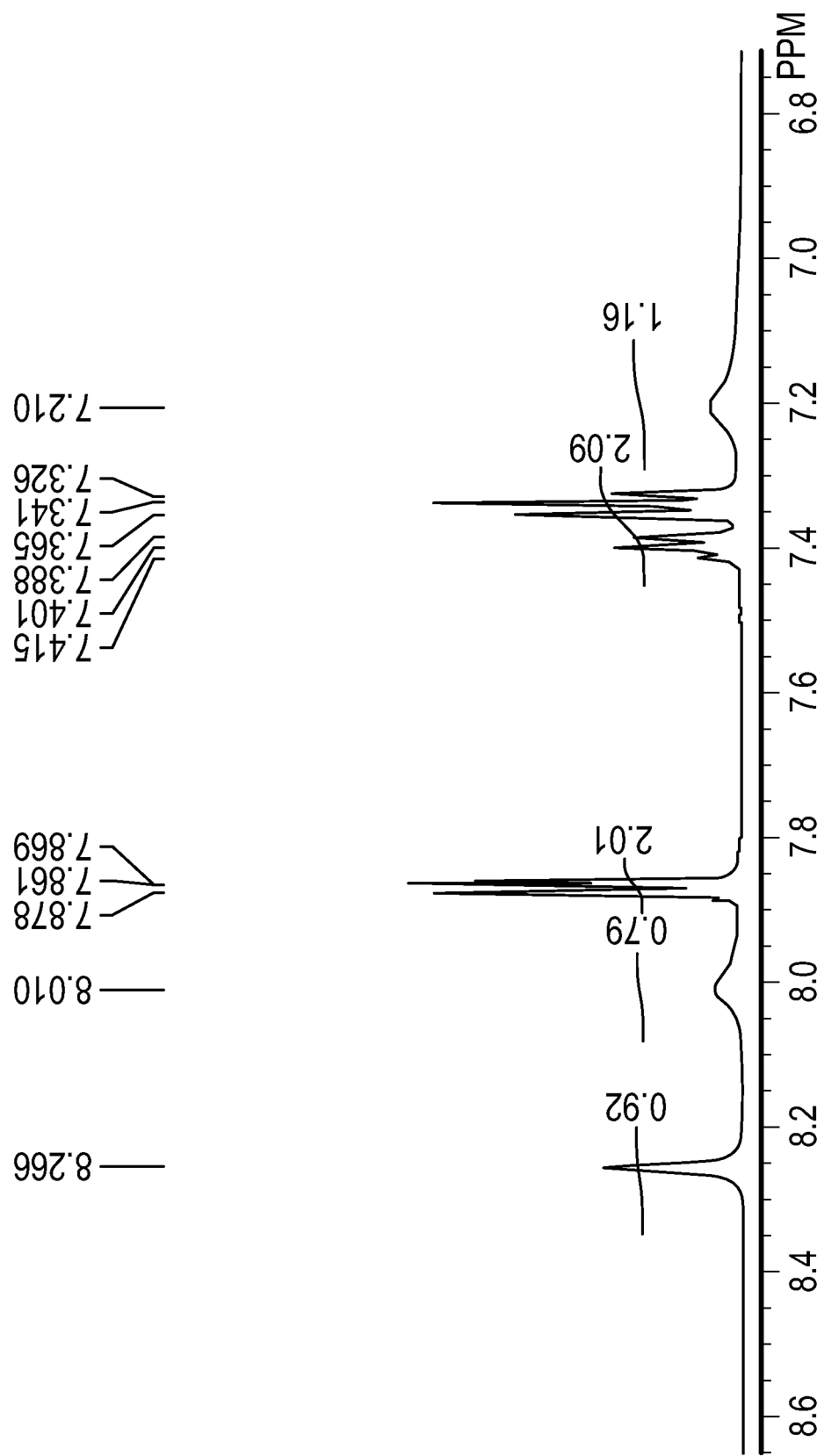

The $^1$HNMR spectra in FIGS. 32 and 33 indicate that the benzoate salt contains one molar equivalent of (1r,4r)-N$^1$-(5-chloro-4-(5-(cyclopropylmethyl)-1-methyl-1H-pyrazol-4-yl)pyrimidin-2-yl)cyclohexane-1,4-diamine and two molar equivalents of benzoic acid.

Figure 38:
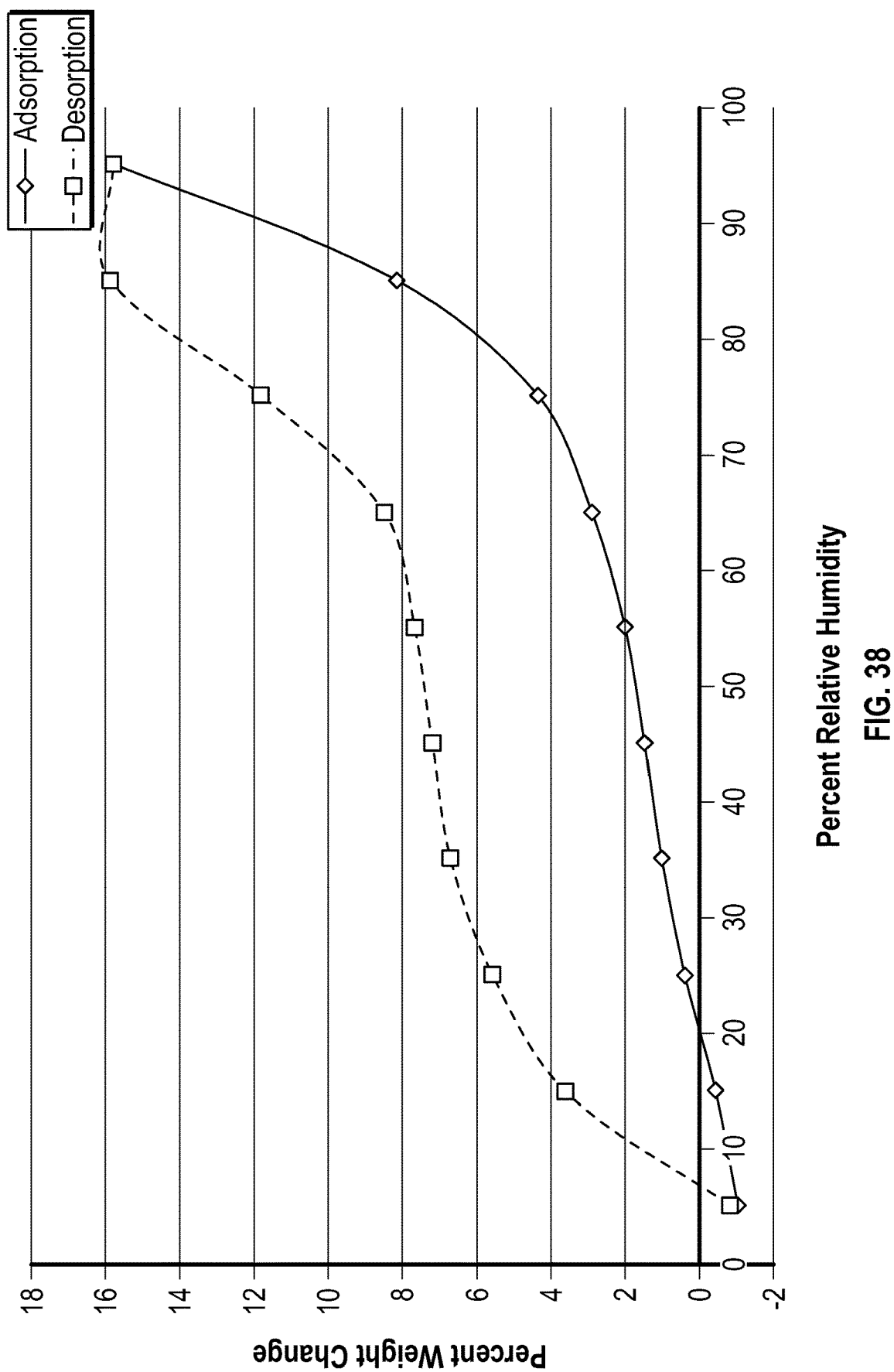
FIG. 38 depicts a DVS isotherm graph of a dihydrochloride salt of the Compound.
Figure 39:
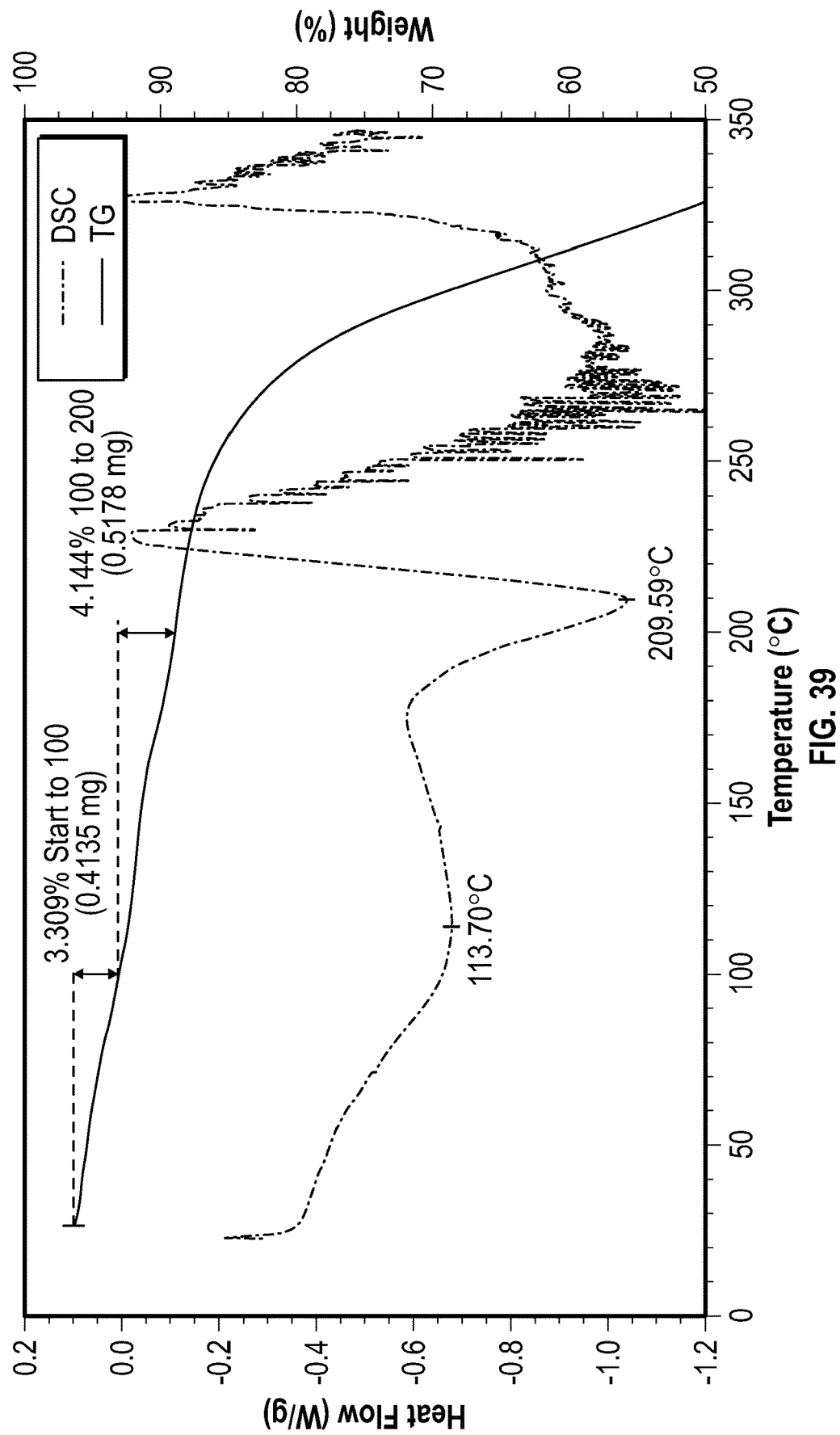
FIG. 39 depicts DSC/TGA thermograms of a dihydrochloride salt of the Compound.

As a comparison, the DVS isotherm graph in FIG. 38 shows that the dihydrochloride salt has (i) 1.2% loss upon drying at 5% RH; (ii) 17% gain from 5 to 95% RH; and (iii) 16% loss from 95 to 5% RH; indicating that the dihydrochloride adipate salt is highly hygroscopic.

The solubilities of the crystalline adipate, benzoate, and tosylate salts as well as a dihydrochloride salt of the Compound were determined by adding a test solvent (e.g., water) in aliquots to a weighed portion of each crystalline solid salt. Whether dissolution had occurred was judged by visual inspection after addition of each solvent aliquot. The results are shown in Table 3.

TABLE 3

Solubilities of Certain Salts of the Compound

| Salt | Solubility (mg/mL) | pH of Solution |
|---|---|---|
| Chloride | 29 | 1.55 |
| Apidate | 14 | 4.73 |
| Benzoate | <1 | 4.31 |
| Tosylate | 2 | 5.82 |

Example 3

Preparation and Characterization of a Crystalline ditosylated Salt of (1r,4r)-$N^1$-(5-chloro-4-(5-(cyclopropylmethyl)-1-methyl-1H-pyrazol-4-yl)pyrimidin-2-yl)cyclohexane-1,4-diamine To a stirred clear solution of (1r,4r)-$N^1$-(5-chloro-4-(5-(cyclopropylmethyl)-1-methyl-1H-pyrazol-4-yl)pyrimidin-2-yl)cyclohexane-1,4-diamine dihydrochloride (20.0 g, 1.0 eq.) in water (10 vol.) was slowly added 10% aq. $Na_2CO_3$ solution (5 vol.) at 25-35° C. The reaction mixture was stirred for 10 h, resulting solid was filtered and it was slurry washed with water (5.0 vol.). The wet material was suck-dried and dried under oven at 50-55° C. for 24 h to yield (1r,4r)-$N^1$-(5-chloro-4-(5-(cyclopropylmethyl)-1-methyl-1H-pyrazol-4-yl)pyrimidin-2-yl)cyclohexane-1,4-diamine as a free base.

To a stirred hazy solution of the above free base compound (1.0 eq.) in methanol (10 vol.) was added p-toluenesulfonic acid·$H_2O$ (2.2 eq.) at 25-35° C. (immediately clear solution formed, after some time again turned into solid suspension). The solid suspension was stirred for 4 h at 50-55° C., then the methanol distilled off under vacuum at below 50° C., the suspension co-distilled with acetone (3.0 vol.) and the residue slurred in acetone (10.0 vol.) for 1-2 h at 25-35° C. The solid suspension was then filtered and the wet compound dried at 50-60° C. under vacuum. $^1$HNMR (400 MHz, $CD_3OD$) δ 8.45 (br, 1H), 8.37 (s, 1H), 7.71 (m, 4H), 7.22 (m, 4H0, 3.92 (m, 1H), 3.91 (s, 3H), 3.17 (m, 2H), 3.14 (m, 1H), 2.33 (s, 6H), 2.13 (m, 4H), 1.58 (m, 4H), 1.04 (m, 1H), 0.50 (m, 2H), 0.24 (m, 2H). $^{13}$C NMR (100 MHz, $CD_3OD$) δ 165.72, 152.87, 149.11(2), 147.32, 143.34, 142.39, 141.87(2), 129.88(4), 126.89(4), 115.57, 115.46, 51.03, 50.32, 37.61, 30.87(2), 30.31(2), 29.90, 21.31(2), 11.07, 5.04(2).

The tosylate salt was also characterized with XRPD, DSC, and DVS. The X-ray power diffractogram in FIG. 34 indicates that the tosylate salt is crystalline. Certain XRDR peaks of the tosylate salt is summarized in Table 4.

TABLE 4

Certain XRPD Peaks for the Ditosylate Salt

| Two-theta angle (°) | d Space(Å) | Intensity (%) |
|---|---|---|
| 5.5 | 16.19 | 65 |
| 6.1 | 14.46 | 9 |
| 7.6 | 11.63 | 47 |
| 12.9 | 6.87 | 20 |
| 14.9 | 5.95 | 10 |
| 16.2 | 5.47 | 17 |
| 17.3 | 5.13 | 22 |
| 18.4 | 4.82 | 18 |
| 18.6 | 4.77 | 11 |
| 21.5 | 4.13 | 10 |
| 21.9 | 4.05 | 100 |

TABLE 4-continued

Certain XRPD Peaks for the Ditosylate Salt

| Two-theta angle (°) | d Space(Å) | Intensity (%) |
|---|---|---|
| 22.3 | 3.99 | 27 |
| 22.5 | 3.95 | 28 |
| 23.4 | 3.80 | 11 |
| 23.8 | 3.75 | 22 |
| 24.1 | 3.70 | 10 |
| 26.2 | 3.40 | 13 |
| 26.9 | 3.32 | 10 |
| 27.0 | 3.30 | 13 |
| 28.8 | 3.10 | 12 |

The DSC thermogram in FIG. 35 shows that the crystalline tosylate salt has an onset value of 224° C. and an endothermic peak of 228° C. The DVS isotherm graph in FIG. 36 indicates that the crystalline tosylate salt is not hygroscopic.

Figure 37:
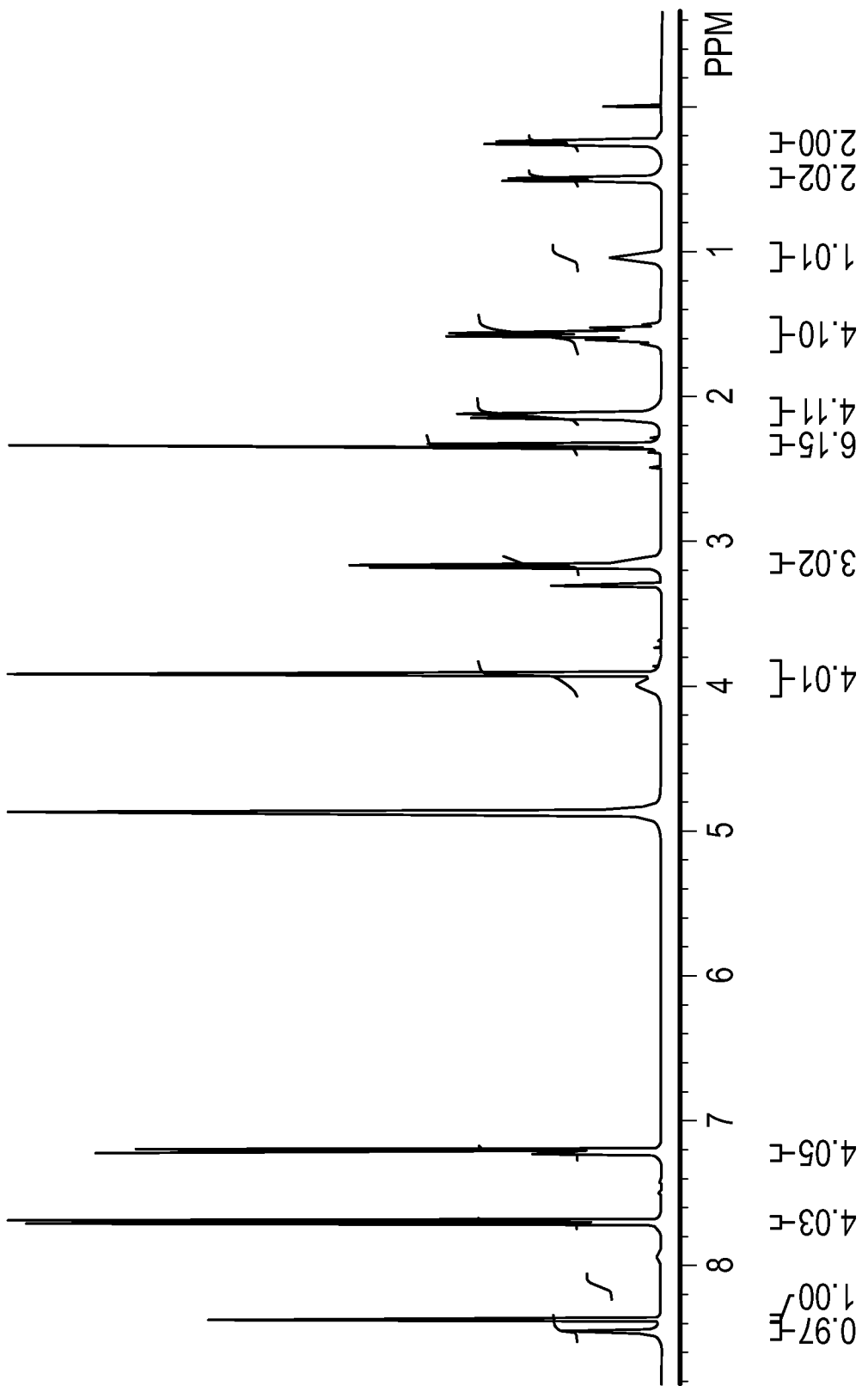
FIG. 37 depicts an expanded region of a $^1$H NMR spectrum of a crystalline tosylate salt of the Compound.

The $^1$HNMR spectrum in FIG. 37 indicates that the crystalline tosylate salt contains one molar equivalent of (1r,4r)-$N^1$-(5-chloro-4-(5-(cyclopropylmethyl)-1-methyl-1H-pyrazol-4-yl)pyrimidin-2-yl)cyclohexane-1,4-diamine and two molar equivalents of p-toluensulfonic acid. The ditosylate salt was determined to have a bulk density of 0.377 g/mL.

Example 4

Stability of a Non-Hygroscopic Crystalline ditosylated Salt of (1r,4r)-$N^1$-(5-chloro-4-(5-(cyclopropylmethyl)-1-methyl-1H-pyrazol-4-yl)pyrimidin-2-yl)cyclohexane-1,4-diamine The stability of the non-hygroscopic crystalline di-tosylate salt was determined at 25±2° C./60±5% RH and 40±2° C./75±5% RH storage conditions. For the stability study, the di-tosylate salt was packaged in a black and transparent polyethylene bag. As shown in Table 5 below, the di-tosylate salt is stable at both 25° C./60% RH and 40° C./75% RH storage conditions with no significant changes in any parameter measured.

TABLE 5

Stability of the Ditosylate Salt

| | Storage Conditions | | | |
|---|---|---|---|---|
| | 40° C./75% RH | | 25° C./60% RH | |
| | Initial | 6-Month | Initial | 6-Month |
| Water contectnt by Karl Fisher (% w/w) | 0.41 | 0.58 | 0.41 | 0.41 |
| Purity by HPLC (% area) | 99.8 | 99.8 | 99.8 | 99.8 |
| Assay by HPLC (% w/w, as free base) | 100.5 | 100.3 | 100.5 | 100.5 |
| pTSA content by HPLC (% w/w) | 49.9 | 49.5 | 49.9 | 48.6 |

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A non-hygroscopic crystalline salt of (1r,4r)-N$^1$-(5-chloro-4-(5-(cyclopropylmethyl)-1-methyl-1H-pyrazol-4-yl)pyrimidin-2-yl)cyclohexane-1,4-diamine or an isotopic variant thereof with an acid, wherein the acid is adipic acid, benzoic acid, or p-toluenesulfonic acid.

2. The non-hygroscopic crystalline salt of claim 1, wherein the salt has a solubility of no greater than 10 mg/mL in water at 25° C.

3. The non-hygroscopic crystalline salt of claim 1, wherein the acid is adipic acid.

4. The non-hygroscopic crystalline salt of claim 3, having an X-ray powder diffractogram substantially as shown in FIG. 24.

5. The non-hygroscopic crystalline salt of claim 1, wherein the acid is benzoic acid.

6. The non-hygroscopic crystalline salt of claim 5, having an X-ray powder diffractogram substantially as shown in FIG. 29.

7. The non-hygroscopic crystalline salt of claim 1, wherein the acid is p-toluenesulfonic acid.

8. The non-hygroscopic crystalline salt of claim 7, having an X-ray powder diffractogram with a peak expressed in two-theta at approximately 5.5, 7.6, and 21.9°.

9. A pharmaceutical composition comprising the non-hygroscopic crystalline salt of claim 1, and a pharmaceutically acceptable excipient.

10. The non-hygroscopic crystalline salt of claim 7, wherein the salt comprises about one molar equivalent of (1r,4r)-N$^1$-(5-chloro-4-(5-(cyclopropylmethyl)-1-methyl-1H-pyrazol-4-yl)pyrimidin-2-yl)cyclohexane-1,4-diamine and two molar equivalents of p-toluenesulfonic acid.

11. The non-hygroscopic crystalline salt of claim 7, wherein the salt comprises about one molar equivalent of (1r,4r)-N$^1$-(5-chloro-4-(5-(cyclopropylmethyl)-1-methyl-1H-pyrazol-4-yl)pyrimidin-2-yl)cyclohexane-1,4-diamine and two molar equivalents of p-toluenesulfonic acid.

12. The non-hygroscopic crystalline salt of claim 7, having an X-ray powder diffractogram with a peak expressed in two-theta at approximately 5.5, 7.6, 12.9, 14.9, 16.2, 17.3, 18.4, 18.6, 21.5, 21.9, 22.3, 22.5, 23.4, 23.8, 24.1, 26.2, 26.9, and 27.0, 28.8°.

13. The non-hygroscopic crystalline salt of claim 7, having an X-ray powder diffractogram substantially as shown in FIG. 34.

14. The non-hygroscopic crystalline salt of claim 7, having a DSC thermogram comprising an endothermic peak at about 228° C.

15. The non-hygroscopic crystalline salt of claim 7, having a DSC thermogram substantially as shown in FIG. 35.

16. The non-hygroscopic crystalline salt of claim 7, having a DVS isotherm graph substantially as shown in FIG. 36.

17. The non-hygroscopic crystalline salt of claim 7, wherein the salt is unsolvated.

18. The non-hygroscopic crystalline salt of claim 7, wherein the salt has a solubility of about 2 mg/mL in water at 25° C.

* * * * *